US012441760B2

(12) United States Patent
Barlos et al.

(10) Patent No.: US 12,441,760 B2
(45) **Date of Patent: *Oct. 14, 2025**

(54) AMINO DIACIDS CONTAINING PEPTIDE MODIFIERS

(71) Applicant: CHEMICAL & BIOPHARMACEUTICAL LABORATORIES OF PATRAS S.A., Patras (GR)

(72) Inventors: Kleomenis Barlos, Patras (GR); Dimitrios Gatos, Patras (GR); Kostas K. Barlos, Patras (GR); Zoi Vasileiou, Patras (GR)

(73) Assignee: CHEMICAL & BIOPHARMACEUTICAL LABORATORIES OF PATRAS S.A., Patras (GR)

( * ) Notice: Subject to any disclaimer, the term of this patent is extended or adjusted under 35 U.S.C. 154(b) by 0 days.

This patent is subject to a terminal disclaimer.

(21) Appl. No.: 18/189,057

(22) Filed: Mar. 23, 2023

(65) Prior Publication Data

US 2024/0002433 A1 Jan. 4, 2024

Related U.S. Application Data

(60) Continuation of application No. 16/195,145, filed on Nov. 19, 2018, now Pat. No. 11,634,455, which is a (Continued)

(30) Foreign Application Priority Data

Aug. 29, 2013 (GB) ..................................... 1315335

(51) Int. Cl.

| | |
|---|---|
| ***C07K 1/04*** | (2006.01) |
| ***A61K 47/54*** | (2017.01) |
| ***C07C 269/04*** | (2006.01) |
| ***C07C 269/06*** | (2006.01) |
| ***C07C 271/02*** | (2006.01) |
| ***C07C 323/60*** | (2006.01) |
| ***C07K 1/107*** | (2006.01) |

(Continued)

(52) U.S. Cl.

CPC .......... *C07K 1/1075* (2013.01); *A61K 47/542* (2017.08); *C07C 269/04* (2013.01); *C07C 269/06* (2013.01); *C07C 271/02* (2013.01); *C07C 323/60* (2013.01); *C07K 1/04* (2013.01); *C07K 1/1077* (2013.01); *C07K 14/00* (2013.01); *C07K 14/4703* (2013.01); *C07K 14/473* (2013.01); *C07K 14/505* (2013.01); *C07K 14/575* (2013.01); *C07K 14/57509* (2013.01); *C07K 14/605* (2013.01); *C07K 14/62* (2013.01); *C07K 14/635* (2013.01); *C07K 14/695* (2013.01); *A61K 38/00* (2013.01); *C07C 2603/18* (2017.05)

(58) Field of Classification Search

CPC ...... C07K 1/1075; C07K 1/04; C07K 1/1077; C07K 14/00; C07K 14/4703; C07K 14/473; C07K 14/505; C07K 14/575; C07K 14/57509; C07K 14/605; C07K 14/62; C07K 14/635; C07K 14/695; C07K 1/107; A61K 47/542; A61K 38/00; A61K 47/62; C07C 269/04; C07C 269/06; C07C 271/02; C07C 323/60; C07C 2603/18; C07C 233/47; C07C 235/12; C07C 237/22; C07C 271/16; C07C 271/22; C07C 323/52; A61P 43/00

See application file for complete search history.

(56) References Cited

U.S. PATENT DOCUMENTS 7,691,968 B2 4/2010 Evans et al.
7,893,017 B2 2/2011 Lau et al.

(Continued)

FOREIGN PATENT DOCUMENTS

CN 102584944 A 7/2012
CN 102875665 A 1/2013

(Continued)

OTHER PUBLICATIONS

Agnihotri et al., "Structure—Activity Relationships in Nucleotide Oligomerization Domain 1 (Nod1) Agonistic y-Glutamyldiaminopimelic Acid Derivatives", *Journal of Medicinal Chemistry* 24:1190-1510 (2011).

(Continued)

*Primary Examiner* — Sudhakar Katakam
(74) *Attorney, Agent, or Firm* — Lathrop GPM LLP; Brian C. Trinque

(57) ABSTRACT

The present invention relates to peptide modifier compounds of Formula (1), or a salt thereof, wherein: a is an integer from 1 to 10, more preferably from 1 to 3; b is an integer from 0 to 7; Z is a terminal group and Y is a bivalent group. Further aspects of the invention relate to intermediates in the preparation of compounds of Formula (1), and the use of compounds of Formula (1) in the synthesis of peptide derivatives.

Formula 1

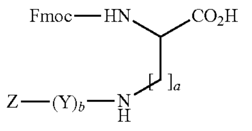

8 Claims, No Drawings

Specification includes a Sequence Listing.

Related U.S. Application Data division of application No. 14/914,374, filed as application No. PCT/IB2014/064123 on Aug. 28, 2014, now abandoned.

(51) Int. Cl.

| | |
|---|---|
| ***C07K 14/00*** | (2006.01) |
| ***C07K 14/47*** | (2006.01) |
| ***C07K 14/505*** | (2006.01) |
| ***C07K 14/575*** | (2006.01) |
| ***C07K 14/605*** | (2006.01) |
| ***C07K 14/62*** | (2006.01) |
| ***C07K 14/635*** | (2006.01) |
| ***C07K 14/695*** | (2006.01) |
| *A61K 38/00* | (2006.01) |

(56) References Cited

U.S. PATENT DOCUMENTS

| | | | |
|---|---|---|---|
| 11,634,455 B2 * | 4/2023 | Barlos .................. | A61K 47/542 514/3.8 |
| 2002/0127577 A1 | 9/2002 | Eichler et al. | |
| 2003/0002006 A1 | 1/2003 | Freeman et al. | |
| 2005/0014681 A1 | 1/2005 | Minamitake et al. | |
| 2005/0124548 A1 | 6/2005 | Henkin et al. | |
| 2007/0111940 A1 | 5/2007 | Larsen et al. | |
| 2010/0197891 A1 | 8/2010 | Giraud et al. | |
| 2010/0239509 A1 | 9/2010 | Chodorowski-Kimmes et al. | |
| 2011/0213131 A1 | 9/2011 | Christensen et al. | |
| 2013/0035285 A1 | 2/2013 | Lau et al. | |
| 2013/0157929 A1 | 6/2013 | Riber et al. | |
| 2015/0073173 A1 | 3/2015 | Puentener | |

FOREIGN PATENT DOCUMENTS

| | | | |
|---|---|---|---|
| CN | 103214568 | A | 7/2013 |
| CN | 103242200 | A | 8/2013 |
| CN | 104271227 | A | 1/2015 |
| EP | 2 664 374 | A1 | 11/2013 |
| JP | 2008-502313 | A | 1/2008 |
| JP | 2011-515358 | A | 5/2011 |
| JP | 2012-507487 | A | 3/2013 |
| KR | 10-2008-0033120 | A | 4/2008 |
| WO | WO 1998/008871 | A1 | 3/1998 |
| WO | WO 1999/064574 | A1 | 12/1999 |
| WO | WO 2001/004156 | A1 | 1/2001 |
| WO | WO 2001/036003 | A2 | 5/2001 |
| WO | WO 2004/062553 | A2 | 7/2004 |
| WO | WO 2004/062601 | A2 | 7/2004 |
| WO | WO 2005/012347 | A2 | 2/2005 |
| WO | WO 2005/072061 | A2 | 8/2005 |
| WO | WO 2005/082404 | A2 | 9/2005 |
| WO | WO 2006/097537 | A2 | 9/2006 |
| WO | WO 2007/127473 | A2 | 11/2007 |
| WO | WO 2009/022006 | A1 | 2/2009 |
| WO | WO 2009/051397 | A2 | 4/2009 |
| WO | WO 2009/114776 | A2 | 9/2009 |
| WO | WO 2009/115469 | A1 | 9/2009 |
| WO | WO 2010/052144 | A2 | 5/2010 |
| WO | WO 2010/070251 | A1 | 6/2010 |
| WO | WO 2010/112942 | A1 | 10/2010 |
| WO | WO 2011/006497 | A1 | 1/2011 |
| WO | WO 2011/045232 | A2 | 4/2011 |
| WO | WO 2011/075393 | A2 | 6/2011 |
| WO | WO 2011/089255 | A1 | 7/2011 |
| WO | WO 2011/117415 | A1 | 9/2011 |
| WO | WO 2011/117416 | A1 | 9/2011 |
| WO | WO 2011/160633 | A1 | 12/2011 |
| WO | WO 2012/006391 | A2 | 1/2012 |
| WO | WO 2012/050227 | A1 | 4/2012 |
| WO | WO 2012/083046 | A2 | 6/2012 |
| WO | WO 2012/088268 | A2 | 6/2012 |
| WO | WO 2013/037266 | A1 | 3/2013 |
| WO | WO 2013/086785 | A1 | 6/2013 |
| WO | WO 2013/092703 | A2 | 6/2013 |
| WO | WO 2013/171135 | A1 | 11/2013 |

OTHER PUBLICATIONS

Baldwin et al., "Synthesis of nonproteinogenic amino acids Part 3: Conversion of glutamic acid into γ,6-Unsaturated α-amino acids", *Tetrahedron* 45(5):1465-1474 (1989).

Berge et al., "Pharmaceutical Salts," *Journal of Pharmaceutical Sciences* 66(1):1-19 (1977).

Bernatowicz et al., "1 H-Pyrazole-1-carboxamidine Hydrochloride: An Attractive Reagent for Guanylation of Amines and Its Application to Peptide Synthesis", *The Journal of Organic Chemistry* 57(8):2497-2502 (1992).

Chan et al., "Fmoc Solid Phase Peptide Synthesis—A Practical Approach", Oxford University Press, 26 pages (2000).

Dyroy et al., Thia Fatty Acids with the Sulfur Atom in Even or Odd Positions Have Opposite Effects on Fatty Acid Catabolism', *Lipids* 41(2):169-177 (2006).

European Examination Report from EP Application No. 14792591.1 dated Nov. 7, 2018, 10 pages.

Friedler et al., "Modulation of Binding of DNA to the C-Terminal Domain of p53 by Acetylation", *Structure* 13:629-636 (2005).

GELACS web-page describing buserelin, https://web.archive.org/web/20080627150045/http://gelacs.com/generic-peptide/buserelin.htm, available Jun. 27, 2008.

Gennaro, Remington's Pharmaceutical Sciences, $17^{th}$ Edition, Mack Publishing Company, 9 pages (1985).

Greene et al., "Protective Groups in Organic Synthesis", John Wiley & Sons, Inc., Second Edition, pp. 1-142 (1991).

Gregersen et al., "Gas Chromatographic Mass Spectrometric Identification of N-Dicarboxylmonoglycines", *Biomedical Mass Spectrometry* 5(1):80-83 (1978).

He et al., "Thiosuccinyl Peptides as Sirt5-Specific Inhibitors", *Journal of the American Chemical Society* 134(4):1922-1925 (2012).

Horwell, "The 'peptoid' approach to the design of non-peptide, small molecule agonists and antagonists of neuropeptides," *Trends in Biotechnology* 13(4):132-134 (1995).

Huhtiniemi et al., "Nε-Modified lysine containing inhibitors for SIRT1 and SIRT2", *Bioorganic & Medicinal Chemistry* 18(15):5616-5625 (2010).

International Search Report with Written Opinion corresponding to International Patent Application No. PCT/IB2014/064123, mailed Jun. 8, 2015, 21 pages.

Isidro-Llobet et al., "Amino Acid-Protecting Groups," *Chemical Reviews* 109(6):2455-2504 (2009).

Japan Oil Chemists' Society, An oil recovery study manual—lipid and the surfactant, The Handbook of Oil Chemistry, 4th Edition, Maruzen, Tokyo (Japan) 2001, p. 12.

Japanese International Search Report from Japanese Patent Application No. 2018-210606 dated Aug. 21, 2019.

Kanazawa et al., "Contribution of Each Amino Acid Residue in Polymyxin $B_3$ to Antimicrobial and Lipopolysaccharide Binding Activity", Chemical & Pharmaceutical Bulletin, 2009, 57(3):240-244 (2009).

Katayama et al., "Pyruvoyl, a novel amino protecting group on the solid phase peptide synthesis and the peptide condensation reaction", *Tetrahedron Letters* 50(7):818-821 (2009).

Kristensen et al., "[$^{125}$I], [$^{127}$I]-and [$^{14}$C]-Labelling of the GLP-1-(7-37) derivative NN2211", *Journal of Labelled Compounds and Radiopharmaceuticals* 46(6):499-510 (2003).

Machon et al., "On-Bead Screening of a Combinatorial Fumaric Acid Derived Peptide Library Yields Antiplasmodial Cysteine Protease Inhibitors with Unusual Peptide Sequences", *Journal of Medicinal Chemistry* 52:5662-5672 (2009).

Mecinovic et al., "2-Oxoglutarate analogue inhibitors of prolyl hydroxylase domain 2", *Bioorganic & Medicinal Chemistry Letters* 19(21):6192-6195 (2009).

Merck Use Information Sheet, Catalogue No. 852042, Product Name: Fmoc-Lys(Ac)-OH Novabiochem®, Merck (2003). [Last Accessed Jun. 10, 2015].

(56) References Cited

OTHER PUBLICATIONS

Mergler et al., "The Bachem practice of SPPS", Bachem sales literature (2005).
Mourtas et al., "Resin-bound mercapto acids: synthesis and application", *Tetrahedron Letters* 43:3419-3421 (2002).
Novabiochem Peptides Synthesis catalogue 2002/2003, Novabiochem 2003, p. 34.
Observation by Third Parties for European Patent Application No. 20167381.1 dated Aug. 1, 2022.
Observation by Third Parties for European Patent Application No. 20167381.1 dated Mar. 10, 2023.
Ombrone et al., "Quantitative liquid chromatography coupled with tandem mass spectrometry analysis of urinary acylglycines: Application to the diagnosis of inborn errors of metabolism", *Analytical Biochemistry* 417(1):122-128 (2011).
Peng et al., "The First Identification of Lysine Malonylation Substrates and Its Regulatory Enzyme", *Molecular & Cellular Proteomics* 10(12):M111.012658, doi:10.1074/mcp.M111.012658 (2011).
Qin et al "On-resin cyclization and antimicrobial activity of Laterocidin and its analogues", *Tetrahedron Letters* 51(9):1257-1261 (2010).
Ragusa et al., "Novel Enantioselective Receptors for N-Protected Glutamate and Aspartate", *Chemistry—A European Journal* 11(19):5674-5688 (2005).
Simon et al., "Peptoids: A modular approach to drug discovery," *PNAS USA* 89(20):9367-9371 (1992).
Van Ameijde et al., "A convenient preparation of several N-linked glycoamino acid building blocks for efficient solid-phase synthesis of glycopeptides", Journal of the Chemical Society, Perkin Transactions 1:1042-1049 (2002).
VOTO Basic Biochemistry, 1st Edition, Tokyo Kagaku Dojin, Nobuo Tamiya, P152 (2000).
Wade et al., Handbook of Pharmaceutical Excipients, Second Edition, American Pharmaceutical Association Washington, The Pharmaceutical Press London, 2 pages (1994).
Zhang et al., "Structural Requirements for a Lipoamino Acid in Modulating the Anticonvulsant Activities of Systemically Active Galanin Analogues", Journal of Medicinal Chemistry 52(5):1310-1316 (2009).

* cited by examiner

SEQUENCE LISTING

```
Sequence total quantity: 58
SEQ ID NO: 1            moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 1
FVNQHLCGSH LVEALYLVCG ERGFFYTPKE                                   30

SEQ ID NO: 2            moltype = AA  length = 31
FEATURE                 Location/Qualifiers
REGION                  1..31
                        note = Description of Artificial Sequence: Synthetic
                         polypeptide
source                  1..31
                        mol_type = protein
                        organism = synthetic construct
SEQUENCE: 2
HAEGTFTSDV SSYLEGQAAK EFIAWLVKGR G                                 31

SEQ ID NO: 3            moltype = AA  length = 28
```

-continued

```
FEATURE                Location/Qualifiers
REGION                 1..28
                       note = Description of Artificial Sequence: Synthetic peptide
source                 1..28
                       mol_type = protein
                       organism = synthetic construct
SEQUENCE: 3
APPRLICDSR VLERYLLEAK EAENITTG                                      28

SEQ ID NO: 4           moltype = AA  length = 32
FEATURE                Location/Qualifiers
REGION                 1..32
                       note = Description of Artificial Sequence: Synthetic
                        polypeptide
source                 1..32
                       mol_type = protein
                       organism = synthetic construct
SEQUENCE: 4
HAEGTFTSDV SSYLEGQAAK EEFIAWLVRG RG                                 32

SEQ ID NO: 5           moltype = AA  length = 28
FEATURE                Location/Qualifiers
REGION                 1..28
                       note = Description of Artificial Sequence: Synthetic peptide
source                 1..28
                       mol_type = protein
                       organism = synthetic construct
SEQUENCE: 5
APPRLICDSR VLERYLLEAK EAENITTG                                      28

SEQ ID NO: 6           moltype = AA  length = 53
FEATURE                Location/Qualifiers
REGION                 1..53
                       note = Description of Artificial Sequence: Synthetic
                        polypeptide
source                 1..53
                       mol_type = protein
                       organism = synthetic construct
SEQUENCE: 6
AQKDAISPPD AASAAPLRTI TADTFRKLFR VYSNFLRGKL KLYTGEACRT GDR          53

SEQ ID NO: 7           moltype = AA  length = 39
FEATURE                Location/Qualifiers
REGION                 1..39
                       note = Description of Artificial Sequence: Synthetic
                        polypeptide
source                 1..39
                       mol_type = protein
                       organism = synthetic construct
SEQUENCE: 7
SYSMEHFRWG KPVGKKRRPV KVYPNGAEDE LAEAFPLEF                          39

SEQ ID NO: 8           moltype = AA  length = 34
FEATURE                Location/Qualifiers
REGION                 1..34
                       note = Description of Artificial Sequence: Synthetic
                        polypeptide
source                 1..34
                       mol_type = protein
                       organism = synthetic construct
SEQUENCE: 8
SVSEIQLMHN LGKHLNSMER VEWLRKKLQD VHNF                               34

SEQ ID NO: 9           moltype = AA  length = 39
FEATURE                Location/Qualifiers
REGION                 1..39
                       note = Description of Artificial Sequence: Synthetic
                        polypeptide
source                 1..39
                       mol_type = protein
                       organism = synthetic construct
SEQUENCE: 9
HGEGTFTSDL SKQMEEEAVR LFIEWLKNGG PSSGAPPPS                          39

SEQ ID NO: 10          moltype = AA  length = 21
FEATURE                Location/Qualifiers
REGION                 1..21
                       note = Description of Artificial Sequence: Synthetic peptide
source                 1..21
```

```
                        mol_type = protein
                        organism = synthetic construct
SEQUENCE: 10
MEVGWYRSPF SRVVHLYRNG K                                        21

SEQ ID NO: 11           moltype = AA  length = 41
FEATURE                 Location/Qualifiers
REGION                  1..41
                        note = Description of Artificial Sequence: Synthetic
                         polypeptide
source                  1..41
                        mol_type = protein
                        organism = synthetic construct
SEQUENCE: 11
SEEPPISLDL TFHLLREVLE MARAEQLAQQ AHSNRKLMEI I                  41

SEQ ID NO: 12           moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 12
YPIKPEAPGE DASPEELNRY YASLRHYLNL VTRQRY                        36

SEQ ID NO: 13           moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 13
YTSLIHSLIE ESQNQQEKNE QELLELDKWA SLWNWF                        36

SEQ ID NO: 14           moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 14
FVNQHLCGSH LVEALYLVCG ERGFFYTPKE                               30

SEQ ID NO: 15           moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 15
FVNQHLCGSH LVEALYLVCG ERGFFYTPKE                               30

SEQ ID NO: 16           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 16
EFIAWLVKGR G                                                   11

SEQ ID NO: 17           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 17
KEFIAWLVRG RG                                                  12
```

```
SEQ ID NO: 18          moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 18
QAAKEFIAWL VKGRG                                                  15

SEQ ID NO: 19          moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 19
TFTSDVSSYL EG                                                     12

SEQ ID NO: 20          moltype = AA  length = 4
FEATURE                Location/Qualifiers
REGION                 1..4
                       note = Description of Artificial Sequence: Synthetic peptide
source                 1..4
                       mol_type = protein
                       organism = synthetic construct
SEQUENCE: 20
HAEG                                                              4

SEQ ID NO: 21          moltype = AA  length = 31
FEATURE                Location/Qualifiers
REGION                 1..31
                       note = Description of Artificial Sequence: Synthetic
                        polypeptide
source                 1..31
                       mol_type = protein
                       organism = synthetic construct
SEQUENCE: 21
HAEGTFTSDV SSYLEGQAAK EFIAWLVKGR G                                31

SEQ ID NO: 22          moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 22
TFTSDVSSYL EG                                                     12

SEQ ID NO: 23          moltype = AA  length = 4
FEATURE                Location/Qualifiers
REGION                 1..4
                       note = Description of Artificial Sequence: Synthetic peptide
source                 1..4
                       mol_type = protein
                       organism = synthetic construct
SEQUENCE: 23
HAEG                                                              4

SEQ ID NO: 24          moltype = AA  length = 28
FEATURE                Location/Qualifiers
REGION                 1..28
                       note = Description of Artificial Sequence: Synthetic peptide
source                 1..28
                       mol_type = protein
                       organism = synthetic construct
SEQUENCE: 24
APPRLICDSR VLERYLLEAK EAENITTG                                    28

SEQ ID NO: 25          moltype = AA  length = 28
FEATURE                Location/Qualifiers
REGION                 1..28
                       note = Description of Artificial Sequence: Synthetic peptide
source                 1..28
                       mol_type = protein
                       organism = synthetic construct
```

```
SEQUENCE: 25
APPRLICDSR VLERYLLEAK EAENITTG                                      28

SEQ ID NO: 26           moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 26
APPRLICDSR VLERYLLEAK EAENITTG                                      28

SEQ ID NO: 27           moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 27
HAEGTFTSDV SSYLEGQAAK EEFIAWLVRG RG                                 32

SEQ ID NO: 28           moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 28
HAEGTFTSDV SSYLEGQAAK EEFIAWLVRG RG                                 32

SEQ ID NO: 29           moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 29
HAEGTFTSDV SSYLEGQAAK EEFIAWLVRG RG                                 32

SEQ ID NO: 30           moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 30
HAEGTFTSDV SSYLEGQAAK EEFIAWLVRG RG                                 32

SEQ ID NO: 31           moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 31
APPRLICDSR VLERYLLEAK EAENITTG                                      28

SEQ ID NO: 32           moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 32
APPRLICDSR VLERYLLEAK EAENITTG                                      28

SEQ ID NO: 33           moltype = AA  length = 28
FEATURE                 Location/Qualifiers
```

```
REGION                 1..28
                       note = Description of Artificial Sequence: Synthetic peptide
source                 1..28
                       mol_type = protein
                       organism = synthetic construct
SEQUENCE: 33
APPRLICDSR VLERYLLEAK EAENITTG                                   28

SEQ ID NO: 34          moltype = AA  length = 53
FEATURE                Location/Qualifiers
REGION                 1..53
                       note = Description of Artificial Sequence: Synthetic
                        polypeptide
source                 1..53
                       mol_type = protein
                       organism = synthetic construct
SEQUENCE: 34
AQKDAISPPD AASAAPLRTI TADTFRKLFR VYSNFLRGKL KLYTGEACRT GDR         53

SEQ ID NO: 35          moltype = AA  length = 53
FEATURE                Location/Qualifiers
REGION                 1..53
                       note = Description of Artificial Sequence: Synthetic
                        polypeptide
source                 1..53
                       mol_type = protein
                       organism = synthetic construct
SEQUENCE: 35
AQKDAISPPD AASAAPLRTI TADTFRKLFR VYSNFLRGKL KLYTGEACRT GDR         53

SEQ ID NO: 36          moltype = AA  length = 39
FEATURE                Location/Qualifiers
REGION                 1..39
                       note = Description of Artificial Sequence: Synthetic
                        polypeptide
source                 1..39
                       mol_type = protein
                       organism = synthetic construct
SEQUENCE: 36
SYSMEHFRWG KPVGKKRRPV KVYPNGAEDE LAEAFPLEF                         39

SEQ ID NO: 37          moltype = AA  length = 34
FEATURE                Location/Qualifiers
REGION                 1..34
                       note = Description of Artificial Sequence: Synthetic
                        polypeptide
source                 1..34
                       mol_type = protein
                       organism = synthetic construct
SEQUENCE: 37
SVSEIQLMHN LGKHLNSMER VEWLRKKLQD VHNF                              34

SEQ ID NO: 38          moltype = AA  length = 39
FEATURE                Location/Qualifiers
REGION                 1..39
                       note = Description of Artificial Sequence: Synthetic
                        polypeptide
source                 1..39
                       mol_type = protein
                       organism = synthetic construct
SEQUENCE: 38
HGEGTFTSDL SKQMEEEAVR LFIEWLKNGG PSSGAPPPS                         39

SEQ ID NO: 39          moltype = AA  length = 21
FEATURE                Location/Qualifiers
REGION                 1..21
                       note = Description of Artificial Sequence: Synthetic peptide
source                 1..21
                       mol_type = protein
                       organism = synthetic construct
SEQUENCE: 39
MEVGWYRSPF SRVVHLYRNG K                                            21

SEQ ID NO: 40          moltype = AA  length = 41
FEATURE                Location/Qualifiers
REGION                 1..41
                       note = Description of Artificial Sequence: Synthetic
                        polypeptide
source                 1..41
```

```
                        mol_type = protein
                        organism = synthetic construct
SEQUENCE: 40
SEEPPISLDL TFHLLREVLE MARAEQLAQQ AHSNRKLMEI I                       41

SEQ ID NO: 41           moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 41
YPIKPEAPGE DASPEELNRY YASLRHYLNL VTRQRY                             36

SEQ ID NO: 42           moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 42
YTSLIHSLIE ESQNQQEKNE QELLELDKWA SLWNWF                             36

SEQ ID NO: 43           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 43
YTSLIHSLIE ESQNQQ                                                   16

SEQ ID NO: 44           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 44
EKNEQELLEL                                                          10

SEQ ID NO: 45           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 45
DKWASLWNWF                                                          10

SEQ ID NO: 46           moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 46
FVNQHLCGSH LVEALYLVCG ERGFFYTPKE                                    30

SEQ ID NO: 47           moltype = AA  length = 31
FEATURE                 Location/Qualifiers
REGION                  1..31
                        note = Description of Artificial Sequence: Synthetic
                         polypeptide
source                  1..31
                        mol_type = protein
                        organism = synthetic construct
SEQUENCE: 47
HAEGTFTSDV SSYLEGQAAK EFIAWLVKGR G                                  31
```

-continued

```
SEQ ID NO: 48           moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 48
APPRLICDSR VLERYLLEAK EAENITTG                                    28

SEQ ID NO: 49           moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 49
HAEGTFTSDV SSYLEGQAAK EEFIAWLVRG RG                               32

SEQ ID NO: 50           moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 50
APPRLICDSR VLERYLLEAK EAENITTG                                    28

SEQ ID NO: 51           moltype = AA  length = 53
FEATURE                 Location/Qualifiers
REGION                  1..53
                        note = Description of Artificial Sequence: Synthetic
                         polypeptide
source                  1..53
                        mol_type = protein
                        organism = synthetic construct
SEQUENCE: 51
AQKDAISPPD AASAAPLRTI TADTFRKLFR VYSNFLRGKL KLYTGEACRT GDR        53

SEQ ID NO: 52           moltype = AA  length = 39
FEATURE                 Location/Qualifiers
REGION                  1..39
                        note = Description of Artificial Sequence: Synthetic
                         polypeptide
source                  1..39
                        mol_type = protein
                        organism = synthetic construct
SEQUENCE: 52
SYSMEHFRWG KPVGKKRRPV KVYPNGAEDE LAEAFPLEF                        39

SEQ ID NO: 53           moltype = AA  length = 34
FEATURE                 Location/Qualifiers
REGION                  1..34
                        note = Description of Artificial Sequence: Synthetic
                         polypeptide
source                  1..34
                        mol_type = protein
                        organism = synthetic construct
SEQUENCE: 53
SVSEIQLMHN LGKHLNSMER VEWLRKKLQD VHNF                             34

SEQ ID NO: 54           moltype = AA  length = 39
FEATURE                 Location/Qualifiers
REGION                  1..39
                        note = Description of Artificial Sequence: Synthetic
                         polypeptide
source                  1..39
                        mol_type = protein
                        organism = synthetic construct
SEQUENCE: 54
HGEGTFTSDL SKQMEEEAVR LFIEWLKNGG PSSGAPPPS                        39

SEQ ID NO: 55           moltype = AA  length = 21
FEATURE                 Location/Qualifiers
REGION                  1..21
                        note = Description of Artificial Sequence: Synthetic peptide
```

-continued

```
source                 1..21
                       mol_type = protein
                       organism = synthetic construct
SEQUENCE: 55
MEVGWYRSPF SRVVHLYRNG K                                          21

SEQ ID NO: 56          moltype = AA  length = 41
FEATURE                Location/Qualifiers
REGION                 1..41
                       note = Description of Artificial Sequence: Synthetic
                        polypeptide
source                 1..41
                       mol_type = protein
                       organism = synthetic construct
SEQUENCE: 56
SEEPPISLDL TFHLLREVLE MARAEQLAQQ AHSNRKLMEI I                    41

SEQ ID NO: 57          moltype = AA  length = 36
FEATURE                Location/Qualifiers
REGION                 1..36
                       note = Description of Artificial Sequence: Synthetic
                        polypeptide
source                 1..36
                       mol_type = protein
                       organism = synthetic construct
SEQUENCE: 57
YPIKPEAPGE DASPEELNRY YASLRHYLNL VTRQRY                          36

SEQ ID NO: 58          moltype = AA  length = 36
FEATURE                Location/Qualifiers
REGION                 1..36
                       note = Description of Artificial Sequence: Synthetic
                        polypeptide
source                 1..36
                       mol_type = protein
                       organism = synthetic construct
SEQUENCE: 58
YTSLIHSLIE ESQNQQEKNE QELLELDKWA SLWNWF                          36
```

AMINO DIACIDS CONTAINING PEPTIDE MODIFIERS

RELATED APPLICATIONS

This application is a Continuation of U.S. patent application Ser. No. 16/195,145, filed Nov. 19, 2018, which application is a Divisional of U.S. patent application Ser. No. 14/914,374, filed Feb. 25, 2016, now abandoned, which is a 35 U.S.C. § 371 filing of International Application No. PCT/IB2014/064123, filed Aug. 28, 2014, which claims priority to Great Britain Patent Application No. 1315335.8, filed Aug. 29, 2013. The entire contents of these applications are incorporated herein by reference in their entireties.

SEQUENCE LISTING

The instant application contains a Sequence Listing which has been submitted electronically in XML format and is hereby incorporated by reference in its entirety. Said XML copy, created on Mar. 22, 2023, is named 740917_DYT-015USDIVCON.xml and is about 74.7 kilobytes in size.

The present invention relates to peptide modifiers with applications in the synthesis of modified peptide derivatives.

BACKGROUND OF THE INVENTION

Peptides are widely used as pharmaceuticals and their application is expected to increase in future. They can be produced by recombinant DNA technology or by conventional chemical synthesis.

Native peptides or analogues thereof generally have a high clearance, which is problematic if a prolonged period of biological activity is desired.

Pharmaceutical peptides which have a high clearance include, for example, ACTH, angiotensin, calcitonin, insulin, glucagon-like peptide-1, glucagon-like peptide-2, insulin like growth factor-1, insulin-like growth factor-2, growth hormone releasing factor, thrombopoietin, erythropoietin, hypothalamic releasing factors, prolactin, PTH and related peptides, endorphins, enkephalins and other opioids, vasopressin, oxytocin, fuzeon, and the like. In many cases it is possible to modify the release properties and the biological activity of peptides by modifying the peptide chain or the amino acid side chains of the peptides. Modifications are often introduced on the side chains of lysine, glutamic acid, aspartic acid cysteine, the amino terminal and the carboxyl terminal functions.

Amino acid side chain or amino terminus modifications are usually performed after the synthesis of the linear peptide by selective deprotection of the distinct amino acid side chain and adding the modification reagent, followed by the steps of peptide deprotection and purification. By way of example, modification of insulin, GLP-1 and chlorotoxin is carried out after the completion of the synthesis of the linear peptide. In many cases the modifiers are diacid derivatives such as glutamic acid, aspartic acid etc. and the modified function is an amino function which can be a side chain amino function of a diamino acid or the N-terminal function of the peptide.

The peptide modifiers can be of any kind, including peptides, amino acids such as glutamic acid and its derivatives, cysteine and its derivatives, and complex molecules such as sugars, polyethylene glycols, lipophilic acids, lipophilic hydrocarbons, chromophores for diagnostic reasons and antigens for raising antibodies and developing vaccines. As the complexity of the modifiers increase, so does their synthesis.

Amino diacids have proved to be suitable linkers between peptides and peptide modifiers. Representative examples are the insulin degludec, and the modified insulin like peptides Liraglutide and Semaglutide, where glutamic acid bound on the side chain of a lysine with its gamma-carboxyl function is used as a linker of the peptide with lipophilic groups. Such modifications are advantageous because the remaining free alpha-carboxyl function increases the water solubility of the modified peptide. Usually the peptide modification is performed post-synthetically. In addition, the modification can be introduced after the assembly of the peptide chain on a suitable resin, the selective removal of the side chain amino protecting group of a diamino acid contained in the peptide sequence (such as lysine) followed by on-resin introduction of the modifying agent.

The present invention seeks to provide new peptide modifiers and methods for the preparation thereof. The peptide modifiers of the invention have applications in the synthesis of peptide derivatives, particularly those for use in therapy.

STATEMENT OF INVENTION

Aspects of the invention are set forth in the accompanying claims.

In a first aspect, the invention relates to a compound of Formula 1, or a salt thereof, Formula 1

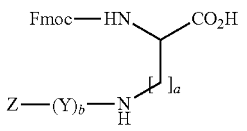

wherein:

a is an integer from 1 to 10, more preferably from 1 to 4, or 1 to 3;

b is an integer from 0 to 7;

Z is a terminal group selected from:

(a) a group of Formula 2

Formula 2

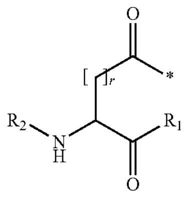

where * denotes the point of attachment to Y;

r is an integer from 1 to 12, more preferably from 2 to 6;

$R_1$ is $NH_2$ or $OR_3$, where $R_3$ is selected from H, alkyl, aryl and aralkyl;

$R_2$ is H or Pr, where Pr is an amino protecting group, preferably Fmoc;

(b) a group of Formula 4 or Formula 5,

Formula 4

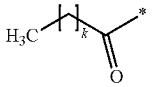

Formula 5

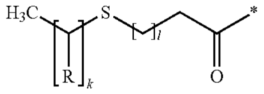

where * denotes the point of attachment to Y; and k and l are each independently an integer from 0 to 25;

(c) a group of Formula 6, 7, 8, or 37

Formula 6

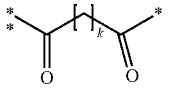

Formula 7

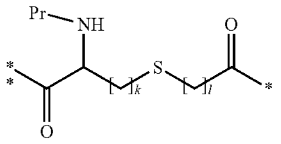

Formula 8

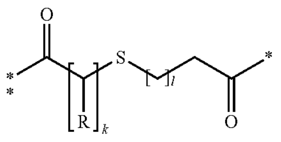

Formula 9

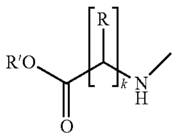

Formula 37

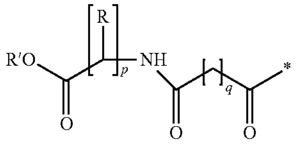

where * denotes the point of attachment to Y;

** indicates a bond to a group selected from OH, OR, NRR' and Formula 9;

Pr is an amino protecting group;

k and l are each independently an integer from 0 to 25; and

R and R' are each independently selected from H, alkyl and aralkyl;

(d) a group of Formula 10,

Formula 10

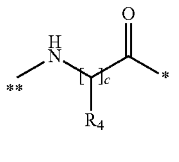

where * denotes the point of attachment to Y;

$R_4$ is the side chain of a natural or unnatural amino acid;

c is an integer from 1 to 12; and

** indicates a bond to a group selected from OH, OR, NRR' and Formula 9; and (e) a group of Formula 11 or Formula 12, Formula 11

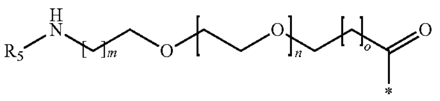

Formula 12

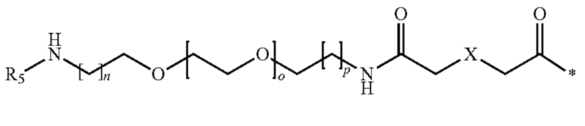

where * denotes the point of attachment to Y;

X is absent, or is selected from $CH_2$, O, S and NR, where R is H, alkyl or aralkyl;

m, n, o, p are each independently an integer from 1 to 25; and $R^5$ is H or Pr, where Pr is an amino protecting group, preferably selected from Fmoc, Boc and Trt;

each Y is independently a bivalent group selected from:

(a) a group of Formula 2'

Formula 2'

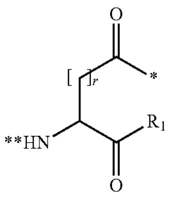

where * denotes the point of attachment (to the NH group of Formula 1);

** indicates a bond to a group Z as defined above or another group Y;

r is an integer from 1 to 12, more preferably from 2 to 6; and $R_1$ is $NH_2$ or $OR_3$, where $R_3$ is selected from H, alkyl, aryl and aralkyl;

(b) a group of Formula 6', 7' or 8',

Formula 6'

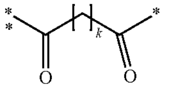

Formula 7'

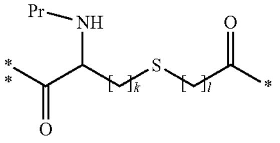

Formula 8'

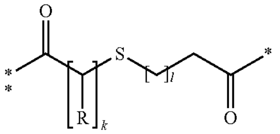

where * denotes the point of attachment (to the NH group of Formula 1);

** indicates a bond to a group Z as defined above or another group Y;

k and l are each independently an integer from 1 to 25;

Pr is an amino protecting group; and

R is selected from H, alkyl and aralkyl;

(c) a group of Formula 10',

Formula 10'

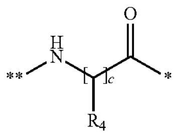

where $R_4$ is the side chain of a natural or unnatural amino acid side chain;

c is an integer from 1 to 12;

* denotes the point of attachment (to the NH group of Formula 1); and

** indicates a bond to a group Z as defined above or another group Y; and (d) a group of Formula 11' or Formula 12', Formula 11'

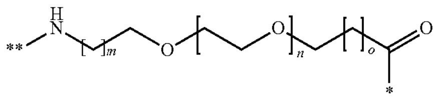

Formula 12'

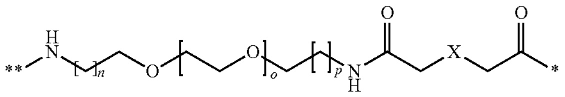

where * denotes the point of attachment (to the NH group of Formula 1);

** denotes a bond to a group Z as defined above or another group Y;

X is absent, or is selected from $CH_2$, O, S and NR, where R is H, alkyl or aralkyl;

and m, n, o, p are each independently an integer from 1 to 25.

A second aspect of the invention relates to a resin conjugate of Formula 18

Formula 18

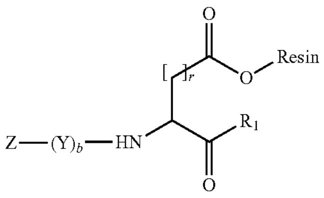

wherein $R_1$ is $NH_2$ or $OR_3$, where $R_3$ is selected from H, alkyl, aryl and aralkyl r is an integer from 1 to 12, more preferably from 2 to 6;

Resin is an acid sensitive resin which allow the cleavage of compounds from the resin selectively in the presence of groups of the $^{t}$Bu-type;

b is an integer from 0 to 7;

Z is a terminal group selected from:

(a) a group of Formula 2

Formula 2

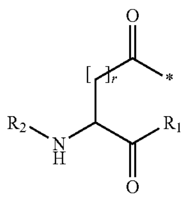

where * denotes the point of attachment to Y;

r is an integer from 1 to 12, more preferably from 2 to 6;

$R_1$ is $NH_2$ or $OR_3$, where $R_3$ is selected from H, alkyl, aryl and aralkyl;

$R_2$ is H or Pr, where Pr is an amino protecting group, preferably Fmoc;

(b) a group of Formula 4 or Formula 5,

Formula 4

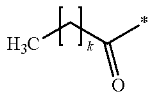

Formula 5

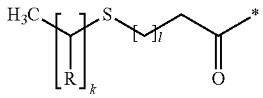

where * denotes the point of attachment to Y; and k and l are each independently an integer from 0 to 25;

(c) a group of Formula 6, 7, 8 or 37,

Formula 6

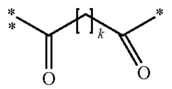

Formula 7

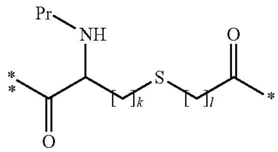

Formula 8

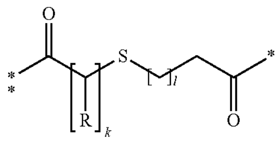

Formula 9

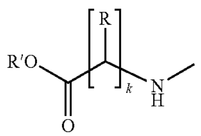

-continued

Formula 37

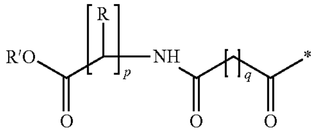

where * denotes the point of attachment to Y;

** indicates a bond to a group selected from OH, OR, NRR' and Formula 9;

Pr is an amino protecting group;

k and l are each independently an integer from 0 to 25; and

R and R' are each independently selected from H, alkyl and aralkyl;

(d) a group of Formula 10,

Formula 10

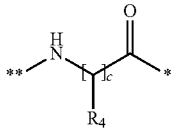

where * denotes the point of attachment to Y;

$R_4$ is the side chain of a natural or unnatural amino acid; and c is an integer from 1 to 12; and

** indicates a bond to a group selected from OH, OR, NRR' and Formula 9;

(e) a group of Formula 11 or Formula 12,

Formula 11

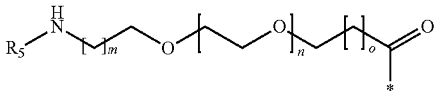

Formula 12

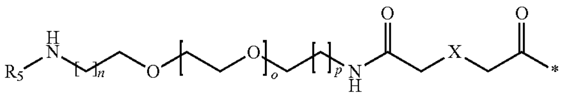

where * denotes the point of attachment to Y;

X is absent, or is selected from $CH_2$, O, S and NR, where R is H, alkyl or aralkyl;

m, n, o, p are each independently an integer from 1 to 25; and $R^5$ is H or Pr, where Pr is an amino protecting group, preferably selected from Fmoc, Boc and Trt;

each Y is independently a bivalent group selected from:

(a) a group of Formula 2'

Formula 2'

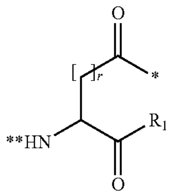

where * denotes the point of attachment (to the NH group of Formula 1);

** indicates a bond to a group Z as defined above or another group Y;

r is an integer from 1 to 12, more preferably from 2 to 6; and $R_1$ is $NH_2$ or $OR_3$, where $R_3$ is selected from H, alkyl, aryl and aralkyl;

(b) a group of Formula 6', 7' or 8',

Formula 6'

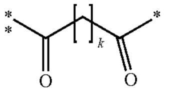

Formula 7'

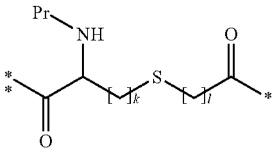

Formula 8'

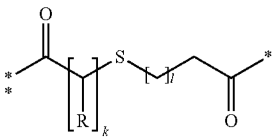

where * denotes the point of attachment (to the NH group of Formula 1);

** indicates a bond to a group Z as defined above or another group Y;

k and l are each independently an integer from 1 to 25;

Pr is an amino protecting group; and

R is selected from H, alkyl and aralkyl;

(c) a group of Formula 10',

Formula 10'

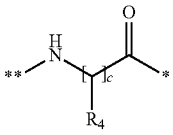

where $R_4$ is the side chain of a natural or unnatural amino acid side chain;

c is an integer from 1 to 12;

* denotes the point of attachment (to the NH group of Formula 1); and

** indicates a bond to a group Z as defined above or another group Y; and (d) a group of Formula 11' or Formula 12', Formula 11'

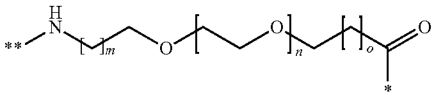

-continued

Formula 12'

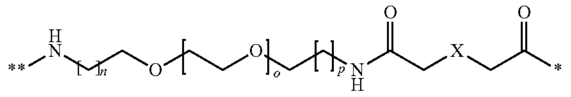

where * denotes the point of attachment (to the NH group of Formula 1);

** denotes a bond to a group Z as defined above or another group Y;

X is absent, or is selected from $CH_2$, O, S and NR, where R is H, alkyl or aralkyl;

and m, n, o, p are each independently an integer from 1 to 25.

A third aspect of the invention relates to a compound (intermediate) of formula:

$Z—(Y)_b—OH$ wherein:

b is an integer from 0 to 7;

Z is a terminal group selected from:

(a) a group of Formula 2

Formula 2

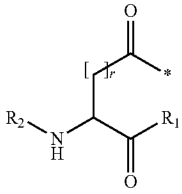

where * denotes the point of attachment to Y;

r is an integer from 1 to 12, more preferably from 2 to 6;

$R_1$ is $NH_2$ or $OR_3$, where $R_3$ is selected from H, alkyl, aryl and aralkyl;

$R_2$ is H or Pr, where Pr is an amino protecting group, preferably Fmoc;

(b) a group of Formula 4 or Formula 5,

Formula 4

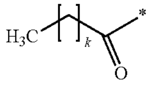

Formula 5

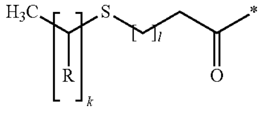

where * denotes the point of attachment to Y; and k and l are each independently an integer from 0 to 25;

(c) a group of Formula 6, 7, 8 or 37

Formula 6

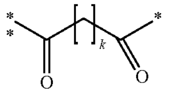

-continued

Formula 7

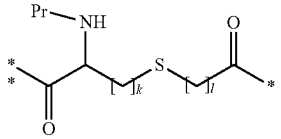

Formula 8

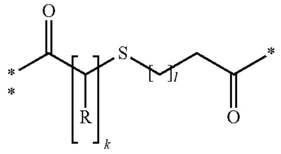

Formula 9

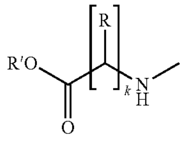

Formula 37

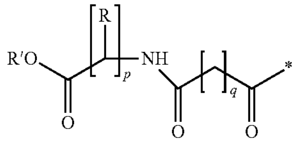

where * denotes the point of attachment to Y;

** indicates a bond to a group selected from OH, OR, NRR' and Formula 9;

Pr is an amino protecting group;

k and l are each independently an integer from 0 to 25;

p is an integer from 1 to 20;

q is an integer from 5 to 20; and

R and R' are each independently selected from H, alkyl and aralkyl;

(d) a group of Formula 10,

Formula 10

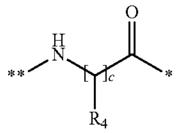

where * denotes the point of attachment to Y;

$R_4$ is the side chain of a natural or unnatural amino acid;

c is an integer from 1 to 12; and

** indicates a bond to a group selected from OH, OR, NRR' and Formula 9; and (e) a group of Formula 11 or Formula 12, Formula 11

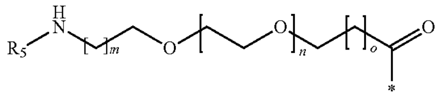

Formula 12

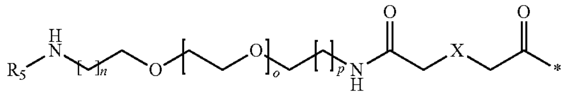

where * denotes the point of attachment to Y;

X is absent, or is selected from $CH_2$, O, S and NR, where R is H, alkyl or aralkyl;

m, n, o, p are each independently an integer from 1 to 25; and $R^5$ is H or Pr, where Pr is an amino protecting group, preferably selected from Fmoc, Boc and Trt;

each Y is independently a bivalent group selected from:

(a) a group of Formula 2'

Formula 2'

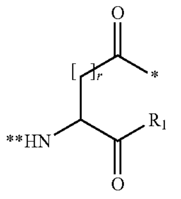

where * denotes the point of attachment (to the OH group);

** indicates a bond to a group Z as defined above or another group Y;

r is an integer from 1 to 12, more preferably from 2 to 6; and $R_1$ is $NH_2$ or $OR_3$, where $R_3$ is selected from H, alkyl, aryl and aralkyl;

(b) a group of Formula 6', 7' or 8',

Formula 6'

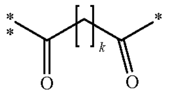

Formula 7'

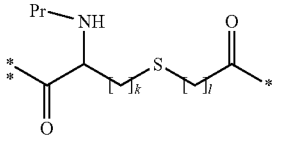

Formula 8'

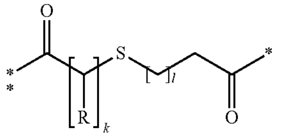

where * denotes the point of attachment (to the OH group);

** indicates a bond to a group Z as defined above or another group Y;

k and l are each independently an integer from 1 to 25;

Pr is an amino protecting group; and

R is selected from H, alkyl and aralkyl;

(c) a group of Formula 10',

Formula 10'

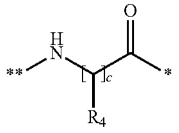

where $R_4$ is the side chain of a natural or unnatural amino acid side chain;

c is an integer from 1 to 12;

* denotes the point of attachment (to the OH group); and

** indicates a bond to a group Z as defined above or another group Y; and (d) a group of Formula 11' or Formula 12', Formula 11'

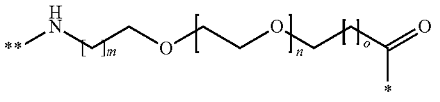

Formula 12'

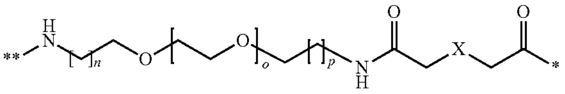

where * denotes the point of attachment (to the OH group);

** denotes a bond to a group Z as defined above or another group Y;

X is absent, or is selected from $CH_2$, O, S and NR, where R is H, alkyl or aralkyl;

and m, n, o, p are each independently an integer from 1 to 25.

Further aspects of the invention relate to processes for the preparation of compounds of Formula 1, and the use of compounds of Formula 1 and intermediates thereof in the preparation of peptide derivatives.

For example, another aspect of the invention relates to the use of a compound as described above in the preparation of a peptide, or a fragment thereof, or a variant thereof.

Another aspect of the invention relates to the use of a resin conjugate as described above in the preparation of a peptide, or a fragment thereof, or a variant thereof.

Another aspect relates to a method of preparing a peptide, or a fragment thereof, or a variant thereof, which comprises using a process according to the invention.

A further aspect of the invention relates to a peptide, or a fragment thereof, or a variant thereof, wherein at least one amino acid residue in said peptide or fragment thereof is modified by side chain attachment of a peptide modifier derived from Z—$(Y)_b$—OH.

Thus, in another aspect, the invention relates to a peptide of Formula 38, or a fragment or variant thereof, Formula 38

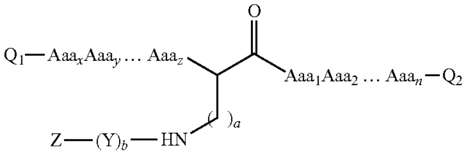

wherein:

a, b, Z and Y are as defined above;

$Q_1$ and $Q_2$ are each independently a terminal group; and $Aaa_xAaa_y \ldots Aaa_z$ and $Aaa_1Aaa_2 \ldots Aaa_n$ are each independently a natural or synthetic peptide comprising 1 to 100 natural or unnatural amino acid residues, each of which is optionally protected.

Another aspect of the invention relates to a peptide, or a fragment thereof, or a variant thereof, as described herein for use in medicine, or for use as a medicament.

Another aspect of the invention relates to a pharmaceutical composition comprising a peptide, or a fragment thereof, or a variant thereof, as described herein admixed with a pharmaceutically acceptable excipient, diluent or carrier.

DETAILED DESCRIPTION

As used herein, the term "alkyl" includes both saturated straight chain and branched alkyl groups which may be substituted (mono- or poly-) or unsubstituted. Preferably, the alkyl group is a $C_{1-20}$ alkyl group, more preferably a $C_{1-15}$, more preferably still a $C_{1-12}$ alkyl group, more preferably still, a $C_{1-6}$ alkyl group, more preferably a $C_{1-3}$ alkyl group. Particularly preferred alkyl groups include, for example, methyl, ethyl, propyl, isopropyl, butyl, isobutyl, tert-butyl, pentyl and hexyl. Suitable substituents include, for example, one or more groups selected from OH, O-alkyl, halogen, $NH_2$, NH-alkyl, N-(alkyl)$_2$, $CF_3$, $NO_2$, CN, COO-alkyl, COOH, $CONH_2$, CO—NH-alkyl, CO—N(alkyl)$_2$, $SO_2$-alkyl, $SO_2NH_2$ and $SO_2$—NH-alkyl.

As used herein, the term "aryl" refers to a $C_{612}$ aromatic group which may be substituted (mono- or poly-) or unsubstituted. Typical examples include phenyl and naphthyl etc. Suitable substituents include, for example, one or more groups selected from OH, O-alkyl, halogen, $NH_2$, NH-alkyl, N-(alkyl)$_2$, $CF_3$, $NO_2$, CN, COO-alkyl, COOH, $CONH_2$, CO—NH-alkyl, CO—N(alkyl)$_2$, $SO_2$-alkyl, $SO_2NH_2$ and $SO_2$—NH-alkyl.

The term "aralkyl" is used as a conjunction of the terms alkyl and aryl as given above.

In all aspects of the present invention described herein, the invention includes, where appropriate all enantiomers and tautomers of the compounds of the invention. The man skilled in the art will recognise compounds that possess optical properties (one or more chiral carbon atoms) or tautomeric characteristics. The corresponding enantiomers and/or tautomers may be isolated/prepared by methods known in the art.

Some of the compounds of the invention may exist as stereoisomers and/or geometric isomers—e.g. they may possess one or more asymmetric and/or geometric centers and so may exist in two or more stereoisomeric and/or geometric forms. The present invention contemplates the use of all the individual stereoisomers and geometric isomers of those compounds, and mixtures thereof. The terms used in the claims encompass these forms.

The present invention also includes all suitable isotopic variations of the compounds or pharmaceutically acceptable salts thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Natural amino acids include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

As used herein, the term "non-natural amino acid" includes alpha and alpha-disubstituted amino acids, N-alkyl amino acids, lactic acid, halide derivatives of natural amino acids such as trifluorotyrosine, p-Cl-phenylalanine, p-F-phenylalanine, p-Br-phenylalanine, p-$NO_2$-phenylalanine, phenylglycine, sarcosine, penicillamine, D-2-methyltryptophan, phosphoserine, phosphothreonine, phosphotyrosine, p-I-phenylalanine, L-allyl-glycine, B1-alanine, β-aspartic acid, β-cyclohexylalanine, citrulline, homoserine, homocysteine, pyroglutamic acid, L-α-amino butyric acid, L-γ-amino butyric acid, L-α-amino isobutyric acid, α-cyclohexylglycine, diaminobutyric acid, diaminopimelic acid, N-ε-dinitrophenyl-lysine, L-1-naphthylalanine, L-2-naphthylalanine, 3-(2-pyridyl)-L-alanine, 3-(3-pyridyl)-L-alanine, 3-(4-pyridyl)-L-alanine, N-ε-methyl-lysine, N,N-ε-dimethyl-lysine, N,N,N-ε-trimethyl-lysine, 3-mercaptopropionic acid, L-ε-amino caproic acid, 7-amino heptanoic acid, 6-amino hexanoic acid L-methionine sulfone, ornithine, L-norleucine, L-norvaline, p-nitro-L-phenylalanine, L-hydroxyproline, γ-glutamic acid, γ-amino butyric acid L-thioproline, methyl derivatives of phenylalanine (Phe) such as 4-methyl-Phe, pentamethyl-Phe, L-Phe (4-amino), L-Tyr (methyl), L-Phe (4-isopropyl), L-Tic (1,2,3,4-tetrahydroisoquinoline-3-carboxyl acid), L-diaminopropionic acid and L-Phe (4-benzyl).

The compounds of the present invention may comprise amino acids in the L or D form, i.e. one or more residues, preferably all the residues may be in the L or D form.

Suitable protecting groups for amino acids will be familiar to the person skilled in the art (see for example, Chem. Rev. 2009, 109, 2455-2504). These protecting groups can be separated into three groups, as follows:

N-terminal protecting groups

C-terminal protecting groups side chain protecting groups

Suitable amino protecting groups are described in "Fmoc Solid Phase Peptide Synthesis—A Practical Approach" W. C. Chan & P. D. White. Oxford University Press, 2000, reprinted 2004.

Suitable hydroxy protecting groups are described in Green T., "Protective Groups in Organic Synthesis", Chapter 1, J. Wiley & Sons, Inc., 1991, 10-142.

Purified, individual amino acids are reacted with these protecting groups prior to synthesis and then selectively removed during specific steps of peptide synthesis.

In the context of the present invention, the term "peptide fragment" refers to an amino acid sequence (or variant thereof) derived from a full length protein. Preferably, the peptide fragment has one or more amino acid residues deleted from the full length protein.

Preferably, the peptide fragment has 1, 2, 3, 4, 5, 6, 7, 8, 9, or 10 amino acid residues deleted from the full length protein. In another preferred embodiment, the peptide fragment comprises at least 50%, at least 60%, at least 70%, at least 80%, at least 90% or at least 95% of the full length sequence.

As used herein, the term "variant" includes any variation wherein; (a) one or more amino acid residues are replaced by a naturally or non-naturally occurring amino acid residue (b) the order of two or more amino acid residues is reversed, (c) both (a) and (b) are present together, (d) a spacer group is present between any two amino acid residues, (e) one or more amino acid residues are in peptoid form, (f) the (N—C—C) backbone of one or more amino acid residues of the peptide has been modified, or any of (a)-(f) in combination. Preferably, the variants arise from one of (a), (b) or (c).

More preferably, one or two amino acids residues are substituted by one or more other amino acid residues. Even more preferably, one amino acid residue is substituted by another amino acid residue. Preferably, the substitution is homologous.

Homologous substitution (substitution and replacement are both used herein to mean the interchange of an existing amino acid residue, with an alternative residue) may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyridylalanine, thienylalanine, naphthylalanine and phenylglycine, a more detailed list of which appears below. More than one amino acid residue may be modified at a time.

As used herein, amino acids are classified according to the following classes;

basic; H, K, R acidic; D, E non-polar; A, F, G, I, L, M, P, V, W polar; C, N, Q, S, T, Y, (using the internationally accepted single letter amino acid notation) and homologous and non-homologous substitution is defined using these classes. Thus, homologous substitution is used to refer to substitution from within the same class, whereas non-homologous substitution refers to substitution from a different class or by an unnatural amino acid.

Suitable spacer groups that may be inserted between any two amino acid residues of the carrier moiety include alkyl groups such as methyl, ethyl or propyl groups in addition to amino acid spacers such as glycine or β-alanine residues. A further form of variation, type (e), involving the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134. Type (f) modification may occur by methods such as those described in International Application PCT/GB99/01855.

It is preferable for amino acid variation, preferably of type (a) or (b), to occur independently at any position. As mentioned above more than one homologous or non-homologous substitution may occur simultaneously. Further variation may occur by virtue of reversing the sequence of a number of amino acid residues within a sequence.

In one embodiment the replacement amino acid residue is selected from the residues of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

The replacement amino acid residue may additionally be selected from unnatural amino acids. Non-natural amino acid derivatives that may be used in the context of the present invention include alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-1-phenylalanine*, L-allyl-glycine*, β-alanine*, L-α-amino butyric acid*, L-γ-amino butyric acid*, L-α-amino isobutyric acid*, L-ε-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid# and L-Phe (4-benzyl)*. The notation * has been utilised for the purpose of the discussion above, to indicate the hydrophobic nature of the derivative whereas # has been utilised to indicate the hydrophilic nature of the derivative, #* indicates amphipathic characteristics.

As mentioned above, the present invention relates to a compound of Formula 1,

Formula 1

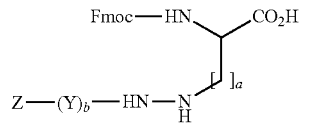

wherein a, b, Z, Y are as defined above.

The Applicant has demonstrated that the introduction of an already modified diamino acid derivative of Formula 1 into a peptide sequence is very advantageous and leads to a reduction of the usual byproducts of post synthetic modification or on-resin modification where the selective modification of the distinct amino function in the presence of other unprotected amino functions (such as in insulin, for example) is often very difficult.

The introduction into the peptide chain of the derivatives of Formula 1 can be performed by any method known in the art.

For example, one preferred embodiment of the invention relates to a process for preparing a peptide derivative of Formula 22, said process comprising the steps of:

(i) reacting a resin-bound peptide of formula H-$Aaa_1$-$Aaa_2$- . . . $Aaa_n$-Resin with a compound of Formula 1 to form a compound of Formula 20;

(ii) removing the protecting group from the compound of Formula 20 and coupling with an at least N-terminally protected amino acid or peptide having a free or activated carboxylic acid function and optionally repeating this step to give a compound of Formula 21;

(iii) removing said compound of Formula 21 from the resin to form a compound of Formula 22.

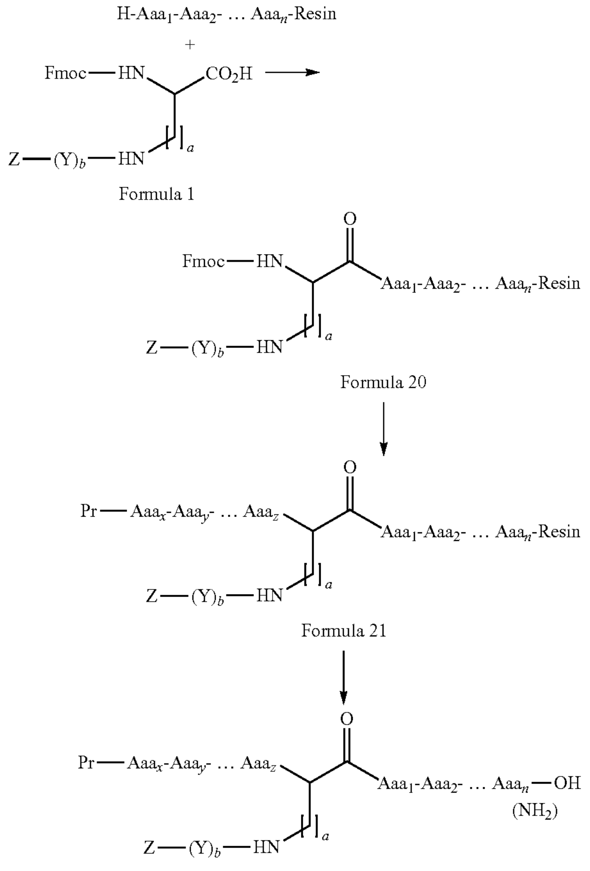

Formula 1

Formula 20

Formula 21

Formula 22

Preferably, the first step in the above process involves a coupling reaction using DIC/HOBt.

In one preferred embodiment, Z is a group of Formula 2.

In another preferred embodiment, Z is a group of Formula 4.

In another preferred embodiment, Z is a group of Formula 5.

In another preferred embodiment, Z is a group of Formula 6.

In another preferred embodiment, Z is a group of Formula 7.

In another preferred embodiment, Z is a group of Formula 8.

In another preferred embodiment, Z is a group of Formula 37.

In another preferred embodiment, Z is a group of Formula 10.

In another preferred embodiment, Z is a group of Formula 11.

In another preferred embodiment, Z is a group of Formula 12.

In one preferred embodiment, Y is a group of Formula 2'.

In another preferred embodiment, Y is a group of Formula 6'.

In another preferred embodiment, Y is a group of Formula 7'.

In another preferred embodiment, Y is a group of Formula 8'.

In another preferred embodiment, Y is a group of Formula 10'.

In another preferred embodiment, Y is a group of Formula 11'.

In another preferred embodiment, Y is a group of Formula 12'.

In one preferred embodiment, the diamino acid derivative is of Formula 13

Formula 13

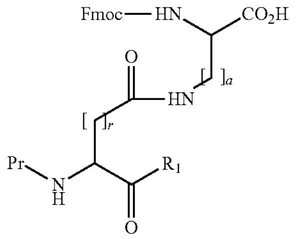

wherein Pr is a protecting group, and a, r and R are as defined above. Preferably, Pr represents a very acid sensitive group of the trityl-type.

More preferably, Pr represents trityl (Trt) or 2-chlorotrityl and R tBu. These new diacid derivatives can be easily introduced into peptide chains similar to 1.

In one preferred embodiment, $R_1$ is O-alkyl, more preferably, $O^t$Bu.

In one preferred embodiment, b is 1 or 2 or 3, more preferably 1 or 2, even more preferably 2.

In another preferred embodiment, b is 0, i.e. Y is absent.

In one preferred embodiment, a is an integer from 1 to 5, more preferably 2 or 3 or 4, even more preferably 2. In one highly preferred embodiment, a is 4.

In one preferred embodiment, Z is a group selected from Formulae 2, 4, 5, 6, 7, 8, 9, 11 and 12.

In one preferred embodiment, Z is a group selected from Formulae 2, 5, 6, 7, 8, 9, 11 and 12.

In one preferred embodiment, each Y is independently a group selected from Formulae 2', 11' and 12'.

In one preferred embodiment, each Y is independently a group selected from Formulae 11' and 12'.

One preferred embodiment of the invention relates to a compound of Formula 1, or a salt thereof, but with the proviso that when a is 4, b is 1, Y is of Formula 2', where r is 2 and $R_1$ is $OR_3$, $R_3$ is alkyl and Z is of Formula 4, k is other than 11 to 19.

One preferred embodiment of the invention relates to a compound of Formula 1, or a salt thereof, but with the proviso that when a is 4, b is 1, Y is of Formula 2', where r is 2 and $R_1$ is $OR_3$, and Z is of Formula 4, k is other than 11 to 19.

One preferred embodiment of the invention relates to a compound of Formula 1, or a salt thereof, but with the proviso that when a is 4, b is 1, Y is of Formula 2', where r is 2 and $R_1$ is $O^tBu$, and Z is other than —C(O)—$C_{12-20}$-alkyl.

One preferred embodiment of the invention relates to a compound of Formula 1, or a salt thereof, but with the proviso that when a is 4, b is 1, Y is of Formula 2', where r is 2 and $R_1$ is $O^tBu$, and Z is other than —C(O)—$C_{15}H_{33}$.

In one especially preferred embodiment, the compound of Formula 1 is selected from the following:

Formula 1-1

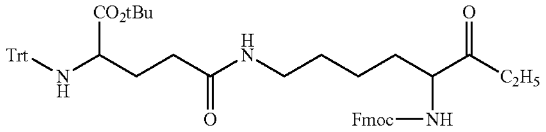

Formula 1-2

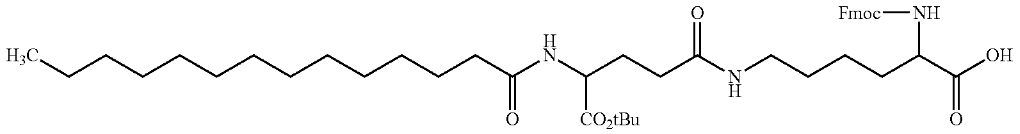

Formula 1-3

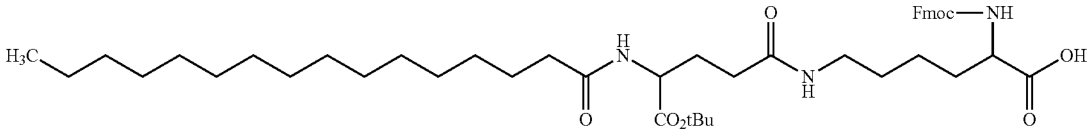

Formula 1-4

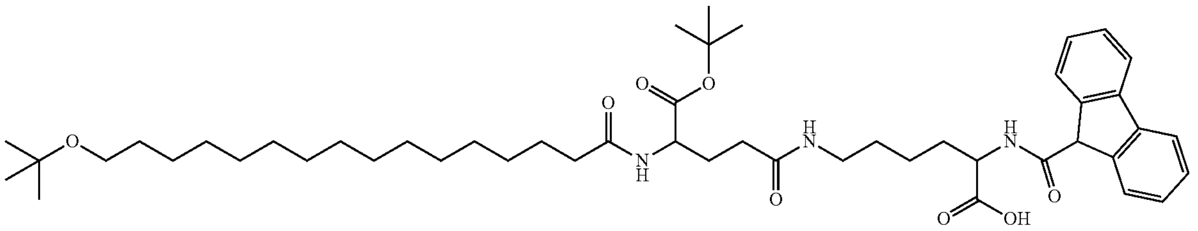

Formula 1-5

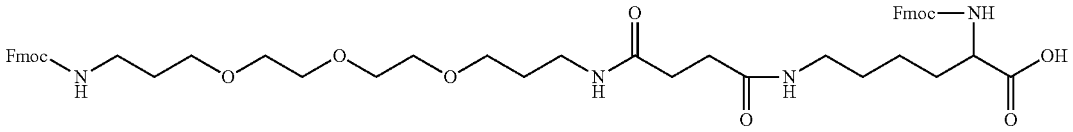

Formula 1-6

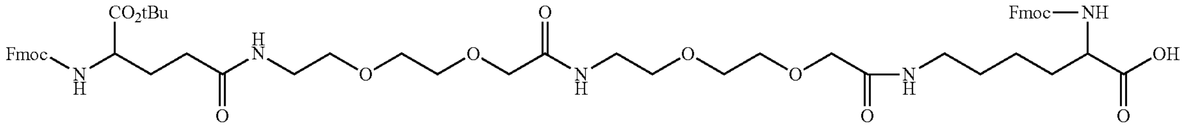

Formula 1-7

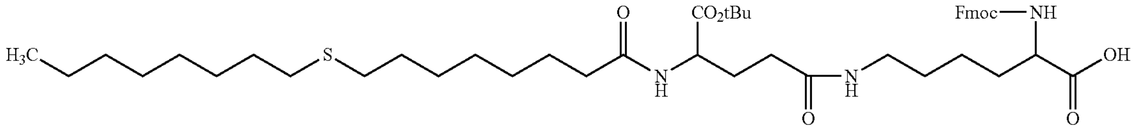

Formula 1-8

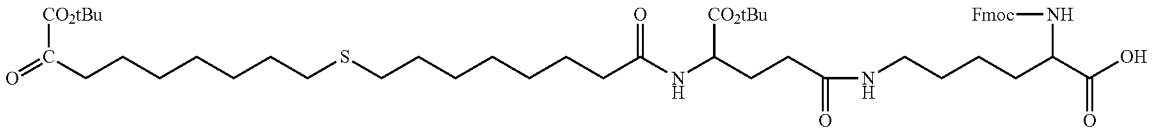

Preferred features for compounds of Formula 1 also apply to other aspects of the invention.

One aspect of the invention relates to a process for preparing a compound of Formula 1 as defined above (see examples 1 and 2), said process comprising reacting a compound of Formula 19 with a compound of Formula Z—$(Y)_b$—OH.

In one embodiment of the invention, compounds of Formula 13 are prepared by the coupling of the new amino diacid derivatives of formula 14 with diamino acid derivatives as shown below.

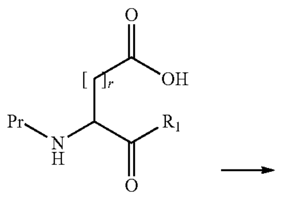

Formula 14

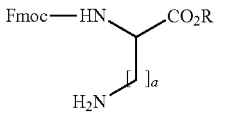

Formula 19

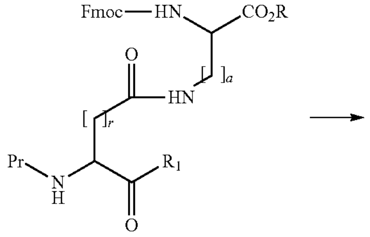

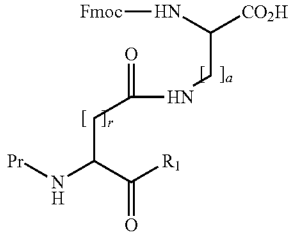

Formula 13

Thus, one embodiment of the invention relates to a process for the preparation of a compound of Formula 13, said process comprising the steps of:

(i) coupling a protected diacid derivative of Formula 14 with an $N^{\alpha}$-protected diamino acid derivative of Formula 19; and (ii) optionally hydrolysing the product formed in step (i) where R is other than H to form a compound of Formula 13.

Preferably, Pr is an acid sensitive protecting group which can be selectively removed in the presence of $^t$Bu-type groups. Preferably, Pr is selected from the trityl-type groups, even more preferably Trt or Clt.

In one highly preferred embodiment, the compound of the invention is of Formula 16

Formula 16

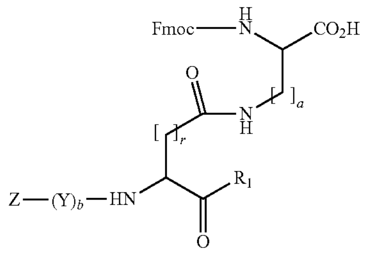

wherein Z, Y, a, b, r and $R_1$ are as defined above.

In one embodiment, compounds of Formula 16, where Y is an amino diacid, are prepared according to the scheme below.

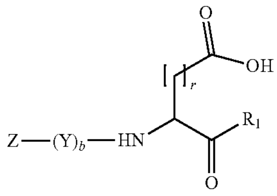

Formula 15

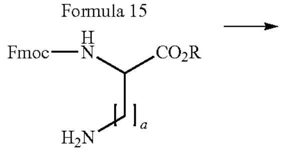

Formula 19

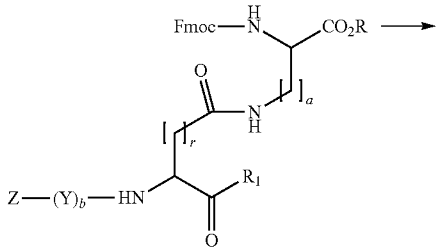

Formula 1a

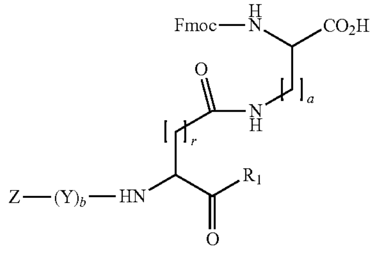

Formula 1b

Thus, one embodiment of the invention relates to a process for the preparation of a compound of Formula 16, said process comprising the steps of:

(i) coupling a protected diacid derivative of Formula 15 with an $N^{\alpha}$-protected diamino acid derivative of Formula 19; and (ii) optionally hydrolysing the product formed in step (i) where R is other than H to form a compound of Formula 16.

In another embodiment the groups Z—Y are introduced on the $N^{\alpha}$-function of the amino diacid of Formula 15 starting from the resin-bound aminodiacid where the side chain carboxyl function of the diacid is bound on a very acid sensitive resin and the side chain carboxyl group is protected as OR' or is $NH_2$ where R' is alkyl, aryl or aralkyl.

Preferably, the resin is a TFA-cleavable resin of the diphenylmethyl or of the trityl type.

Even more preferably, the resin is selected from trityl, 2-chloro-trityl, 4-methyl-trityl and 4-methoxy-trityl resins as shown below, wherein Q can be absent, or is a linker between the trityl-group and the polymer matrix P, such as a carboxyl group.

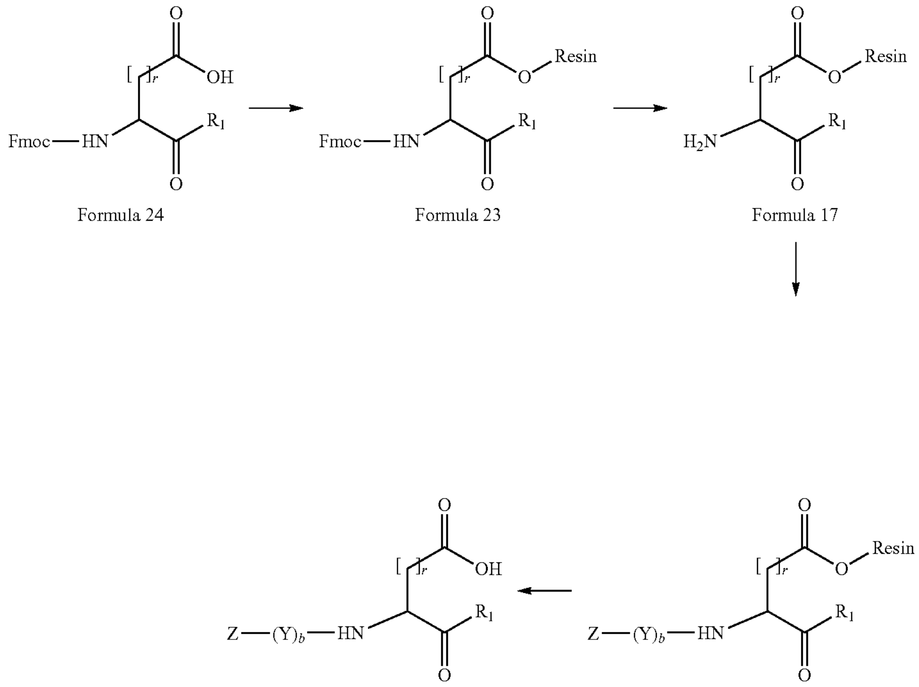

Formula 24 Formula 23 Formula 17

Formula 15 Formula 18

Thus one embodiment of the invention relates to a process for preparing a compound of Formula 15, wherein r is an integer from 1 to 12, more preferably from 2 to 6, said process comprising the steps of:

(i) reacting a compound of Formula 24, where $R_1$ is $NH_2$ or $OR_3$, where $R_3$ is selected from H, alkyl, aryl and aralkyl, with a resin to form a resin-bound compound of Formula 23;

(ii) deprotecting said compound of Formula 23 to form a compound of Formula 17; (iii) converting said compound of Formula 17 into a compound of Formula 18 by reacting with a compound of formula Z—$(Y)_b$—OH; and (iv) removing said compound of Formula 15 from the resin by treating with a mild acid to form a compound of Formula 18.

Preferably, step (i) comprises reacting the compound of Formula 24 with a resin in DCM or THF.

Preferably, step (ii) is carried out in the presence of a base and more preferably in the presence of DIPEA.

Step (iii) may be carried out in multiple steps, or a single reaction step.

Preferably, step (iv) is carried out in the presence of a weak acid.

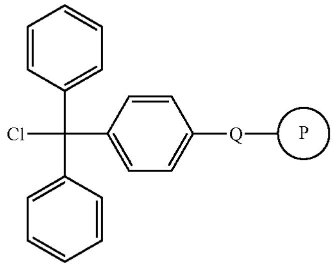

Trt-chloride resin

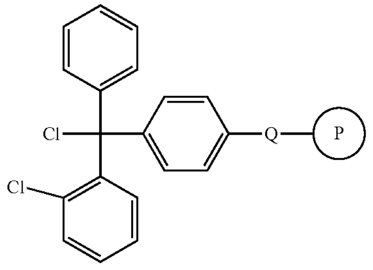

2-chlorotrityl chloride resin

-continued

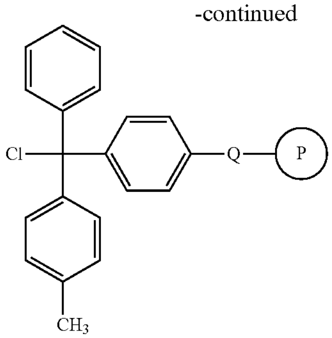

4-methyltrityl cloride resin
Mtt-chloride resin

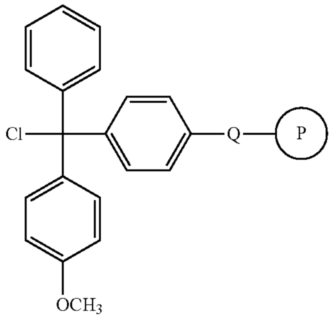

4-methoxytrityl chloride resin
Mmt-chloride resin

Another aspect of the invention relates to compounds (or "resin conjugates") of Formula 18

Formula 18

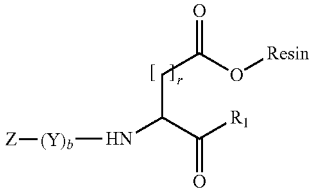

wherein Z, Y, b, r, $R_1$ and Resin are as defined above.

Another aspect of the invention relates to compounds (or "resin conjugates") of Formula 19

Formula 19

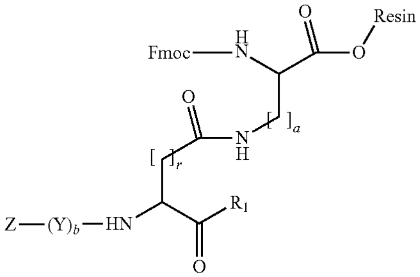

wherein Z, Y, b, r, $R_1$ and Resin are as defined above.

In one preferred embodiment, the acid sensitive resin is selected from trityl, 2-chloro-trityl, 4-methyl-trityl and 4-methoxy-trityl resin, more preferably 2-chlorotrityl resin.

In one highly preferred embodiment, the compound of Formula 18 is selected from the following:

Formula 18-2

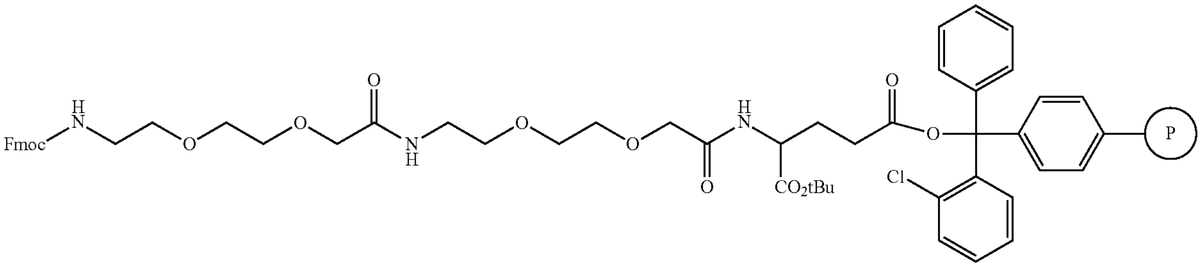

-continued
Formula 18-3
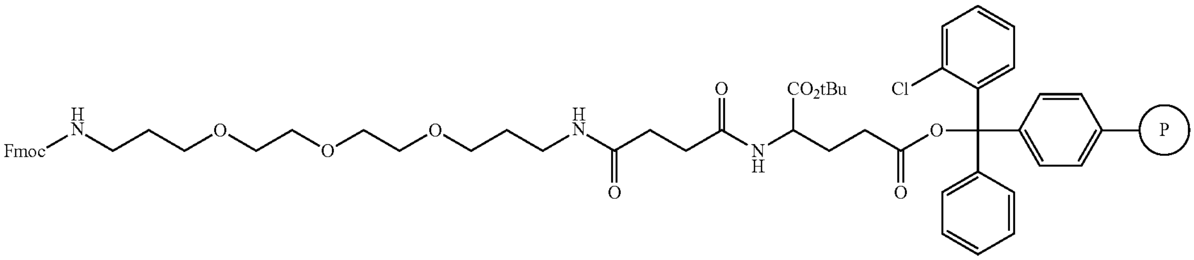
18-4
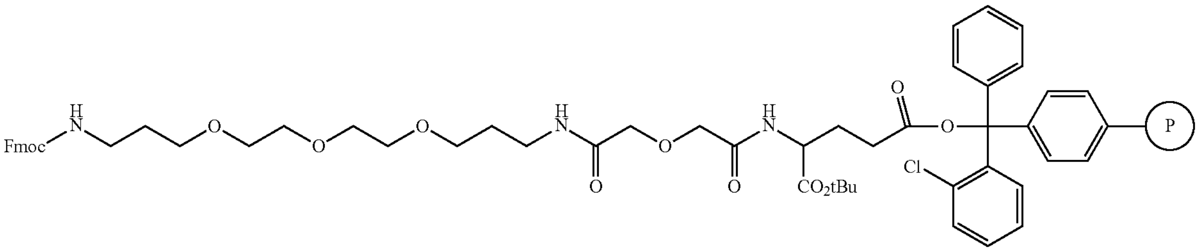
where P is a polymer matrix.
where P is a polymer matrix.
Another aspect of the invention relates to a compound (or "intermediate") of formula Z—(Y)$_b$—OH as defined above.
Highly preferred compounds of formula Z—(Y)$_b$—OH include the following:
Formula 2′-2
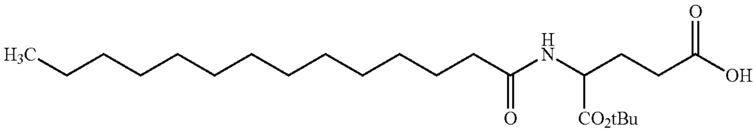
Formula 2′-3
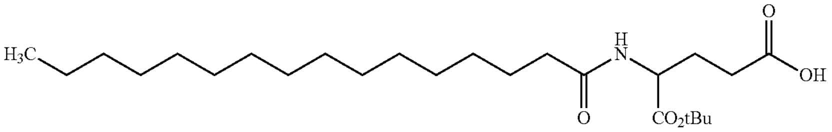
Formula 12-1
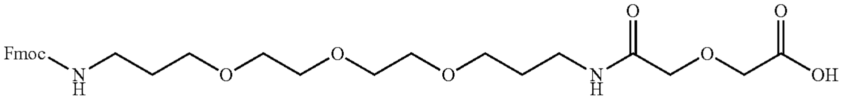
Formula 12-2
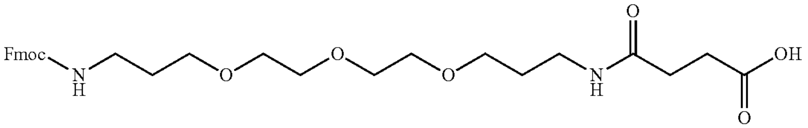
Formula 2′-4
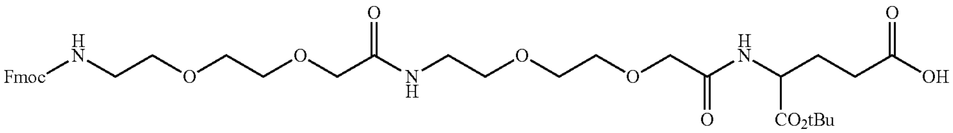
Formula 2′-5
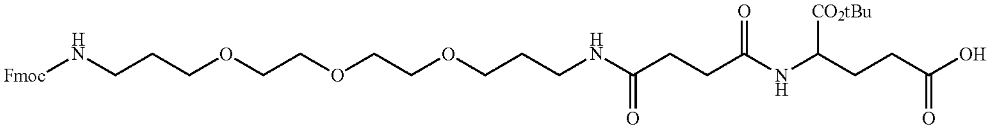

-continued
Formula 2′-6
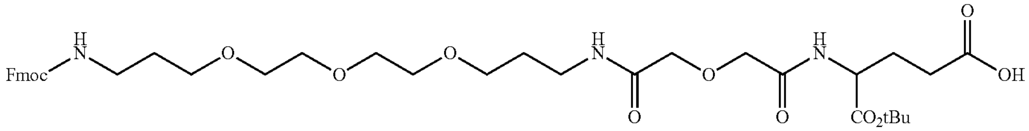
Formula 11-2
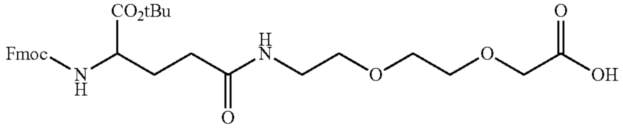
Formula 11-3
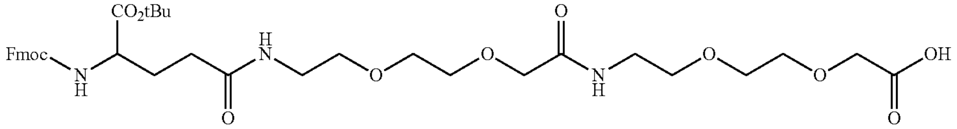
Formula 12-5
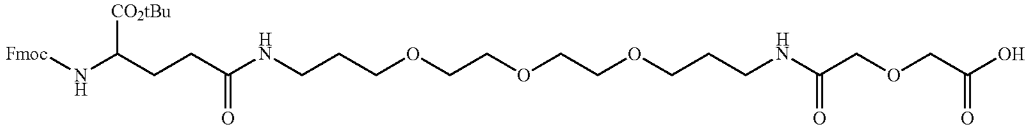
Formula 12-6
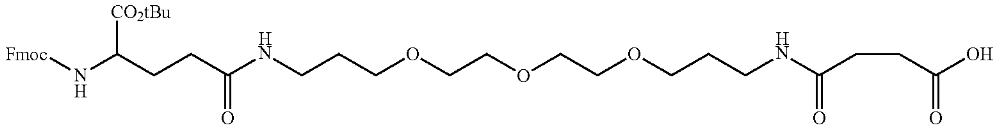
Formula 2′-7
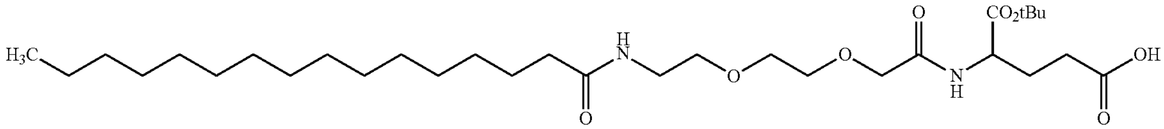
Formula 2′-8
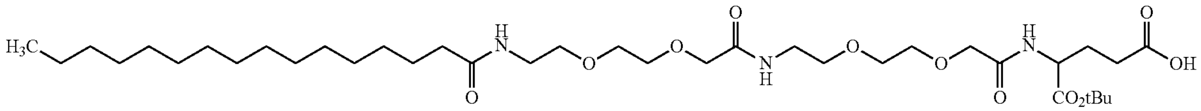
Formula 2′-9
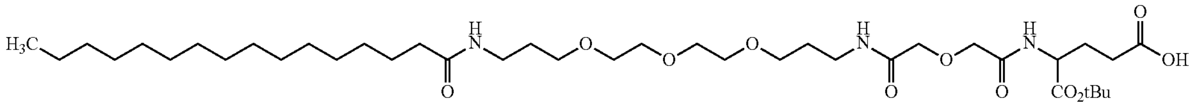
Formula 2′-10
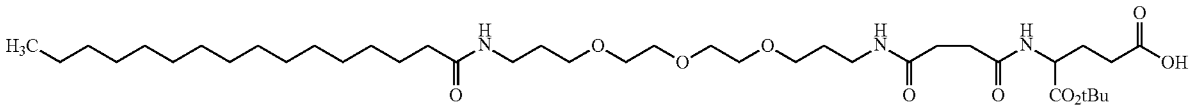
Formula 11-4
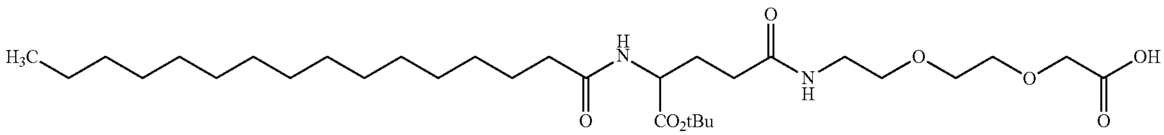
Formula 11-5
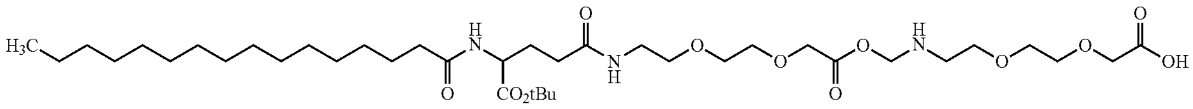

-continued
Formula 12-7
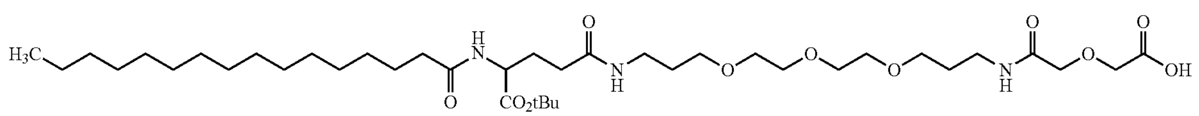
Formula 12-7
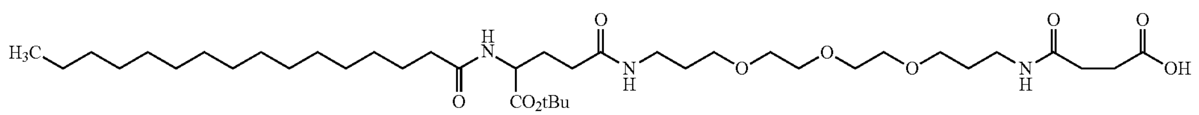
Formula 2′-11
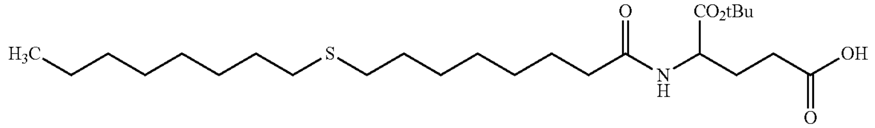
Formula 2′-12
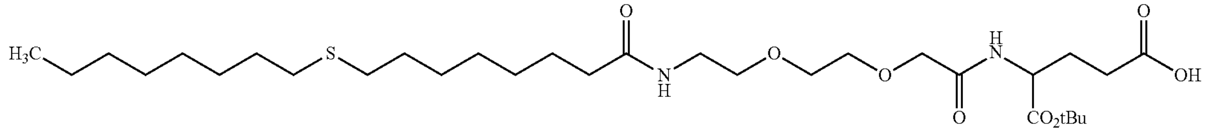
Formula 2′-13
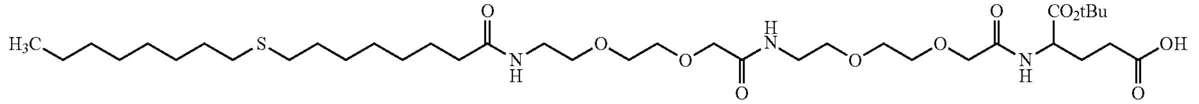
Formula 2′-14
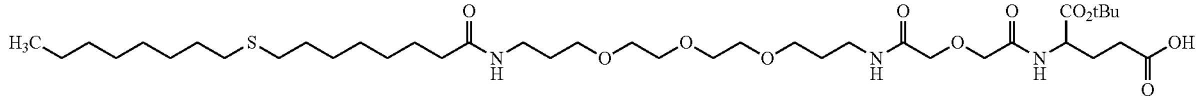
Formula 2′-15
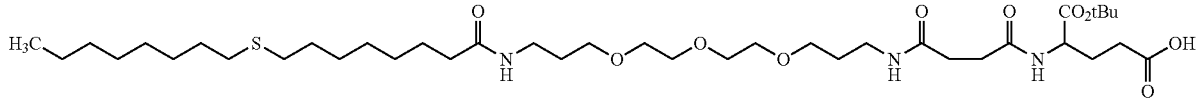
Formula 11-6
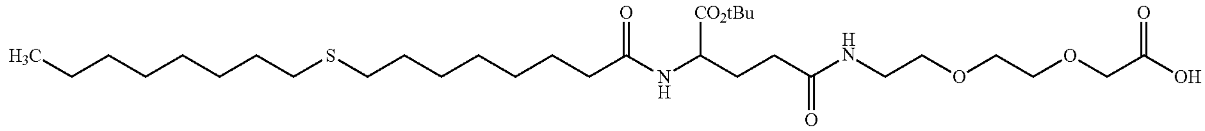
Formula 11-7
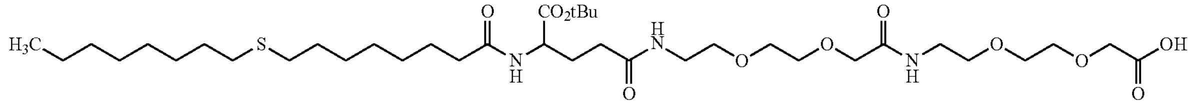
Formula 12-9
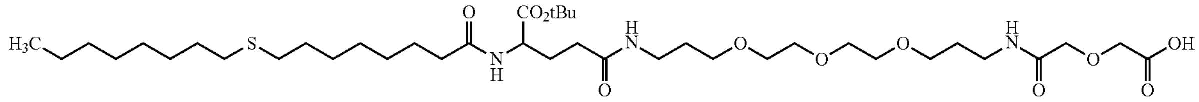
Formula 12-10
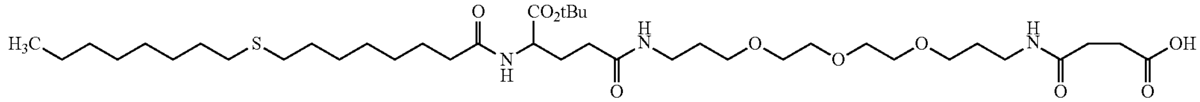

-continued
Formula 2'-16
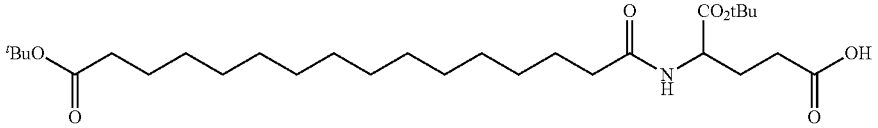
Formula 11-8
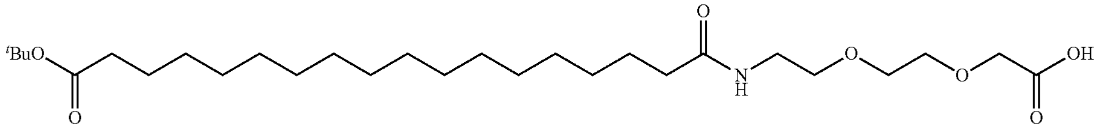
Formula 11-9
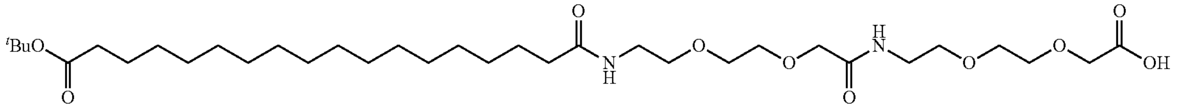
Formula 12-11
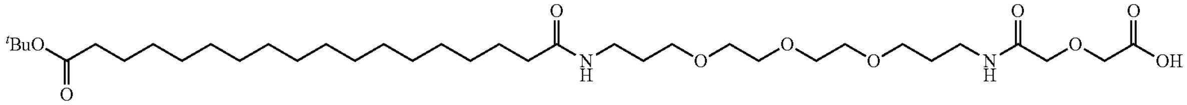
Formula 12-12
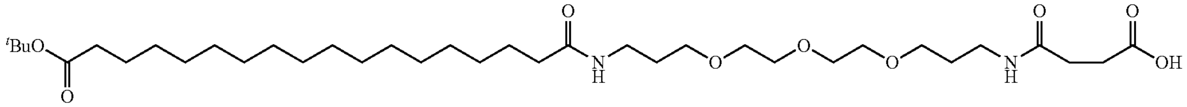
Formula 2'-17
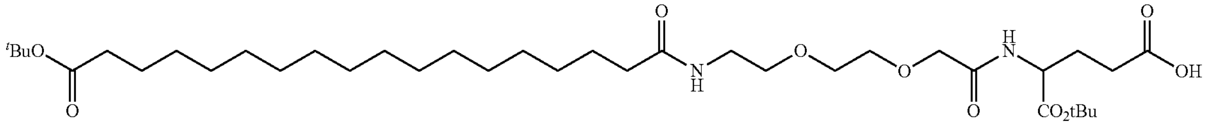
Formula 2'-18
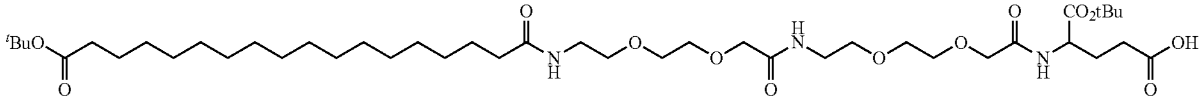
Formula 2'-19
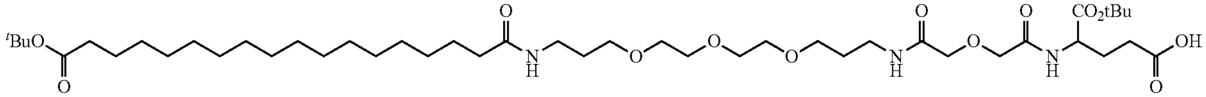
Formula 2'-20
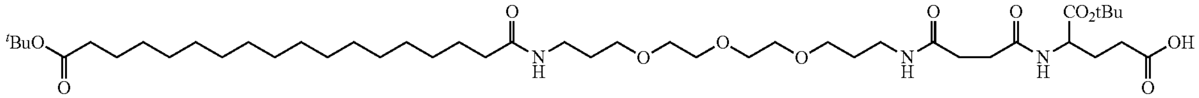
Formula 11-10
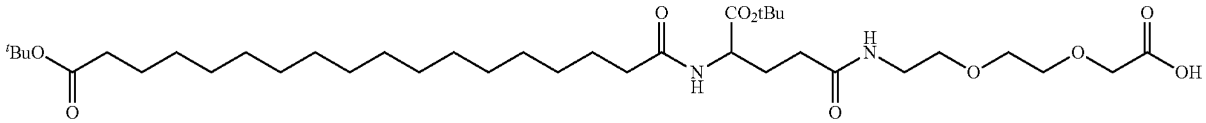
Formula 11-11
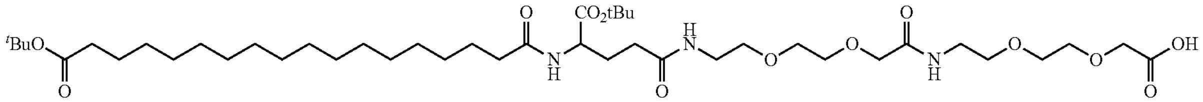

-continued
Formula 12-13
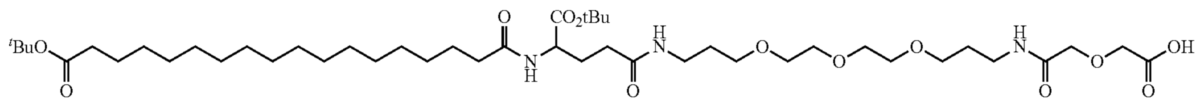
Formula 12-14
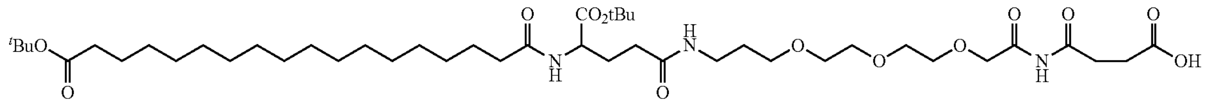
Formula 2′-21
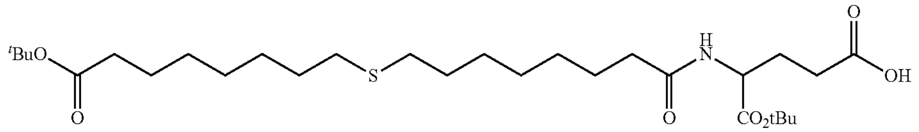
Formula 2′-22
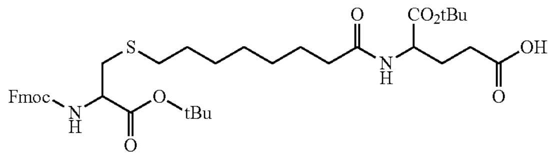
Formula 26-1
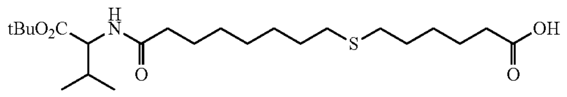
Formula 11-12
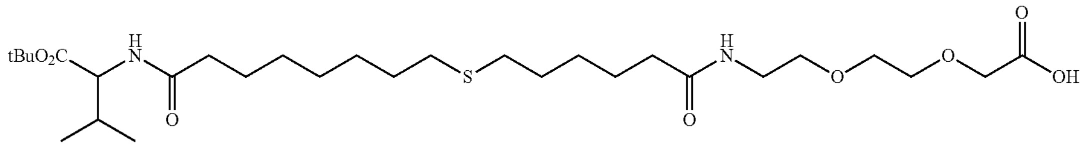
Formula 11-12
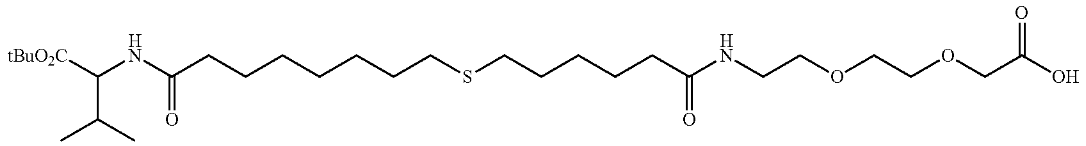
Formula 12-15
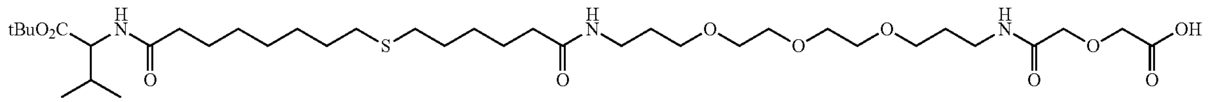
Formula 12-16
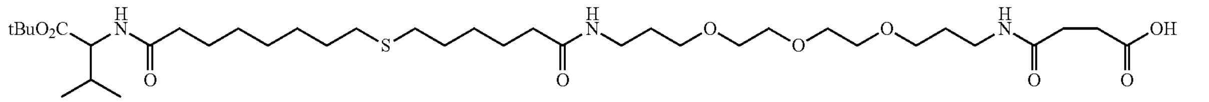
Formula 2′-23
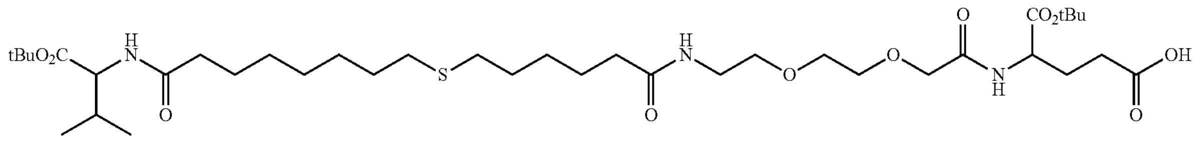
Formula 2′-24
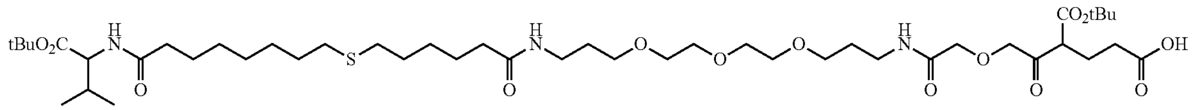

-continued
Formula 2′-25
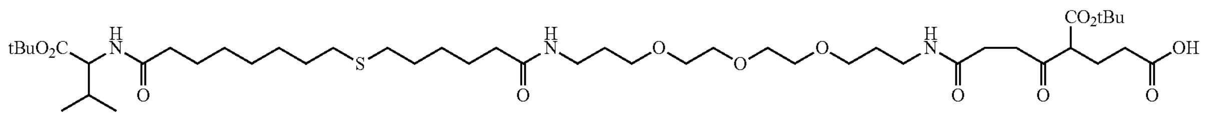
Formula 11-13
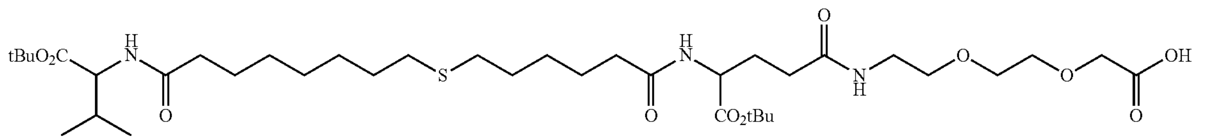
Formula 12-17
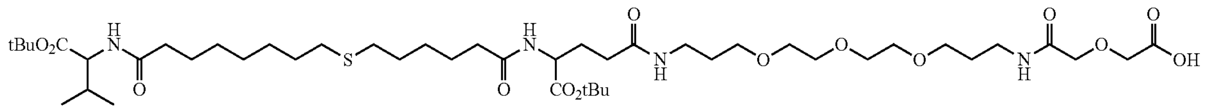
Formula 12-18
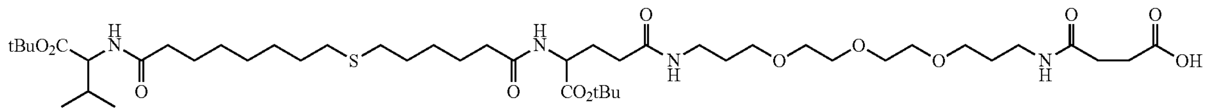
Formula 2′-26
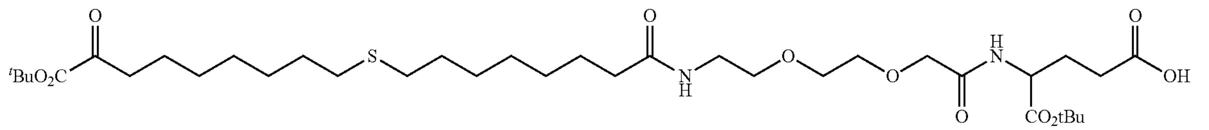
Formula 2′-27
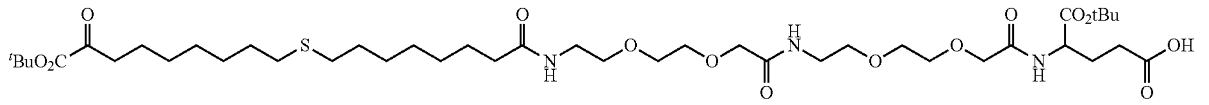
Formula 2′-28
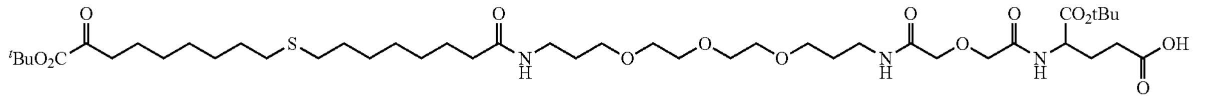
Formula 2′-29
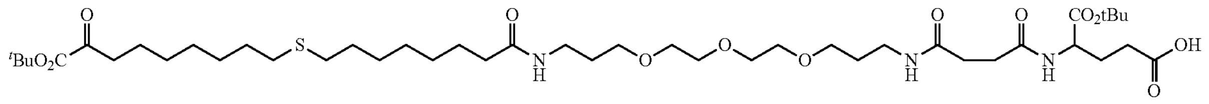
Formula 11-15
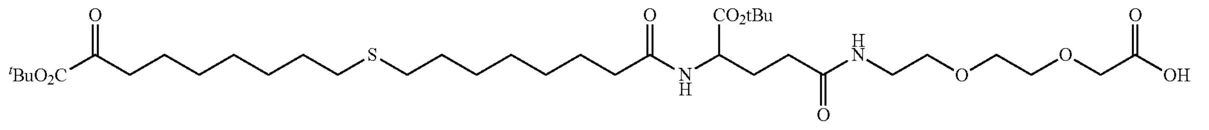
Formula 11-16
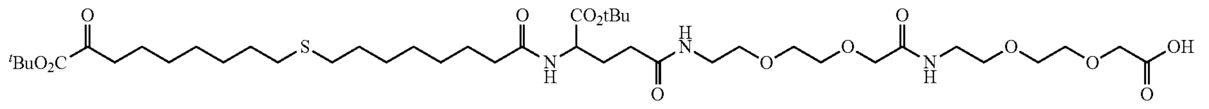
Formula 12-19
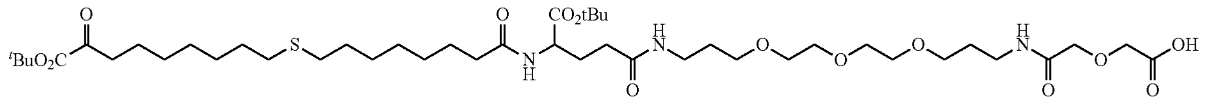

-continued

Formula 12-20

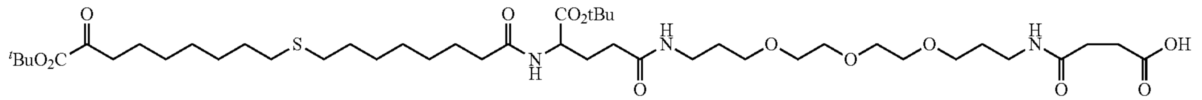

Formula 11-17

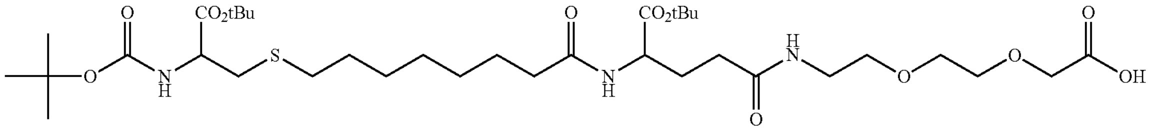

Formula 11-18

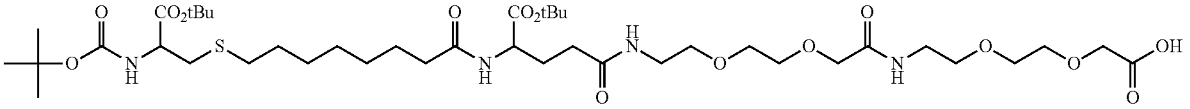

Formula 12-21

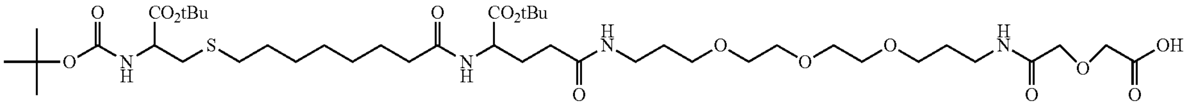

Formula 12-22

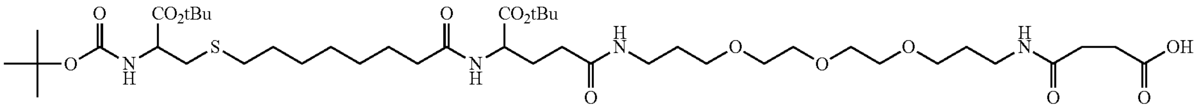

Formula 2′-30

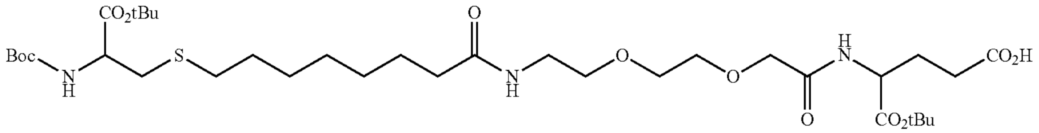

Formula 2′-31

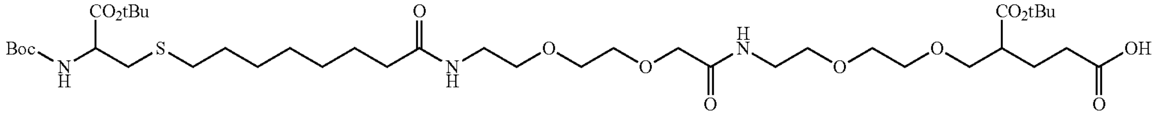

Formula 2′-32

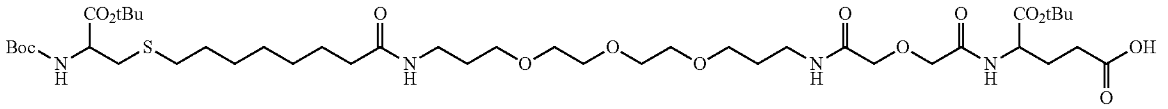

Formula 2′-33

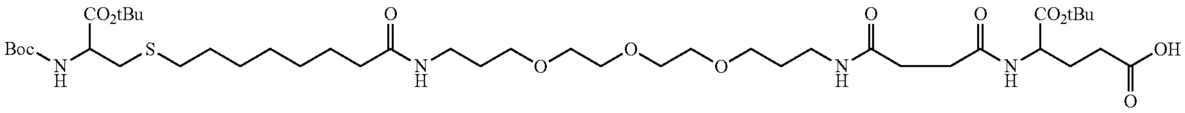

Compounds of formula Z—(Y)$_b$—OH, such as those described above, may be used to prepare compounds of Formula 1 as defined above, for example by reacting with compound of Formula 19.

Another aspect of the invention relates to the use of a compound as described above in the preparation of a peptide, or a fragment thereof, or a variant thereof.

Another aspect of the invention relates to the use of a resin conjugate as described above in the preparation of a peptide, or a fragment thereof, or a variant thereof.

Another aspect relates to a method of preparing a peptide, or a fragment thereof, or a variant thereof, which comprises using a process according to the invention.

Another aspect relates to a peptide, or a fragment thereof, or a variant thereof, wherein at least one amino acid residue in said peptide or fragment thereof is modified by side chain attachment of a peptide modifier derived from Z—(Y)$_b$—OH, wherein Z, Y and b are as defined above. Preferably, the peptide modifier derived from Z—(Y)$_b$—OH is attached via the side chain of a lysine residue.

In one preferred embodiment, the peptide, or a fragment or variant thereof, is of Formula 38

Formula 38

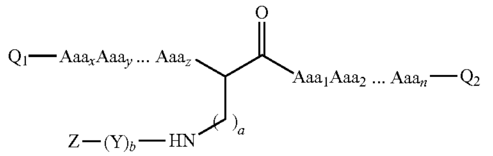

wherein:

a, b, Z and Y are as defined above;

$Q_1$ and $Q_2$ are each independently a terminal group; and $Aaa_xAaa_y$ . . . $Aaa_z$ and $Aaa_1Aaa_2$ . . . $Aaa_n$ are each independently a natural or synthetic peptide comprising 1 to 100 natural or unnatural amino acid residues, each of which is optionally protected.

Preferably, $Q_1$ is H or a protecting group.

Preferably, $Q_2$ is OH or $NH_2$.

In one highly preferred embodiment, the peptide or fragment thereof is selected from the following:

(i)

(SEQ ID NO: 1)

Boc-Phe-Val-Asn(Trt)-Gln(Trt)-His(Trt)-Leu-Cys(Trt)-Gly-Ser(tBu)-His(Trt)-Leu-Val-Glu(tBu)-Ala-Leu-Tyr(tBu)-Leu-Val-Cys(Trt)-Gly-Glu(tBu)-Arg(Pbf)-Gly-Phe-Phe-Tyr(tBu)-Thr(tBu)-Pro-Lys(H-Glu-OtBu)-OH (ii)

(SEQ ID NO: 2)

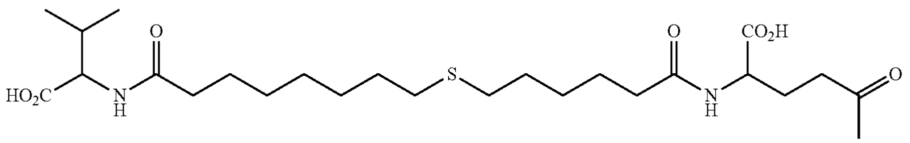

H-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Arg-Gly-OH (iii)

(SEQ ID NO: 3)

H-Ala-Pro-Pro-Arg-Leu-Ile-Cys-Asp-Ser-Arg-Val-Leu-Glu-Arg-Tyr-Leu-Leu-Glu-Ala-Lys-Glu-Ala-Glu-Asn-Ile-Thr-Thr-Gly-S-$CH_2$-$CH_2$-$CO_2Me$

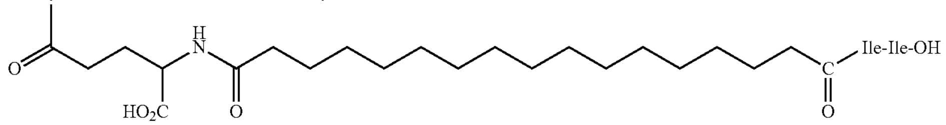

(iv)

(SEQ ID NO: 4)

H-His-Ala-Glu-Gly-Thr-Phe-Thr-Ser-Asp-Val-Ser-Ser-Tyr-Leu-Glu-Gly-Gln-Ala-Ala-Lys(Palm-Glu-OH)-Glu-Phe-Ile-Ala-Trp-Leu-Val-Arg-Gly-Arg-Gly-O (v)

(SEQ ID NO: 5)

Boc-Ala-Pro-Pro-Arg(Pbf)-Leu-Ile-Cys(trt)-Asp(tBu)-Ser(tBu)-Arg(Pbf)-Val-Leu-Glu(tBu)-Arg(Pbf)-Tyr(tBu)-Leu-Leu-Glu(tBu)-Ala

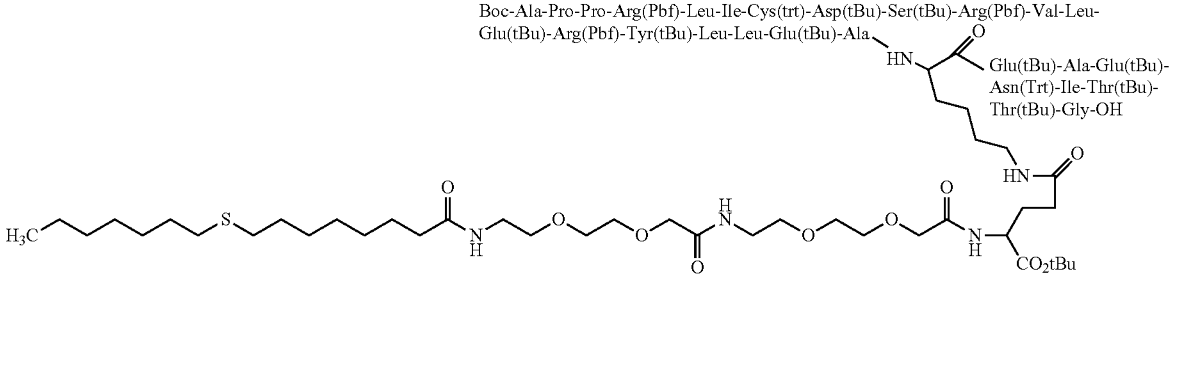

Glu(tBu)-Ala-Glu(tBu)-Asn(Trt)-Ile-Thr(tBu)-Thr(tBu)-Gly-OH

-continued
(vi)
(SEQ ID NO: 6)
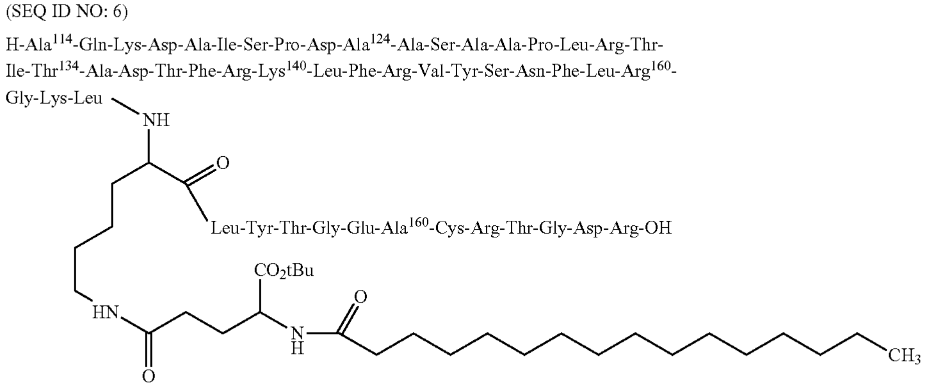
(vii)
(SEQ ID NO: 7)
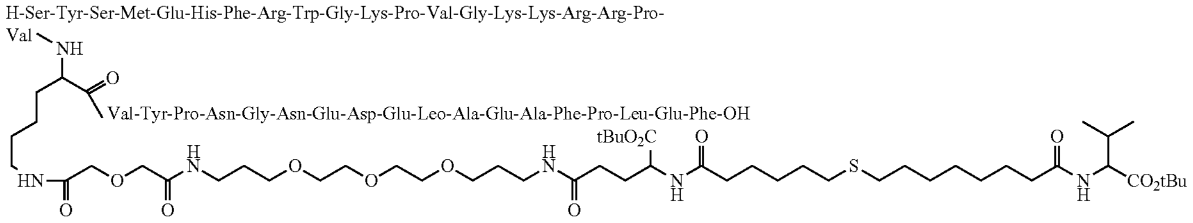
(viiii)
(SEQ ID NO: 8)
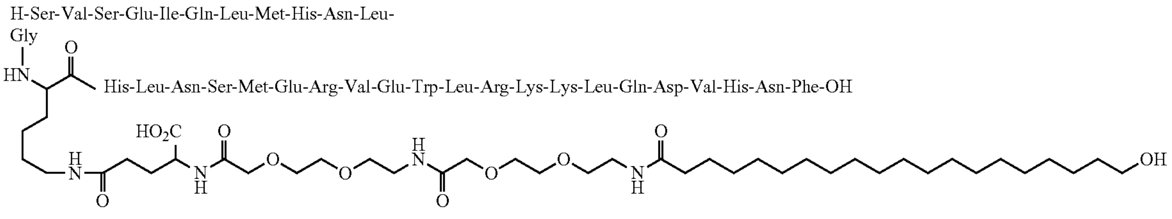
(ix)
(SEQ ID NO: 9)
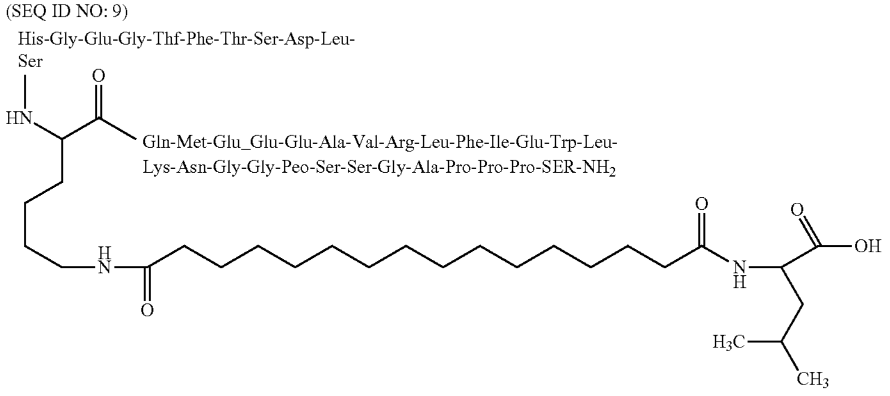

-continued (x)

(SEQ ID NO: 10)

H-Met-Glu-Val-Gly-Trp-Tyr-Arg-Ser-Pro-Phe-Ser-Arg-Val-Val-His-Leu-Tyr-Arg-Asn-

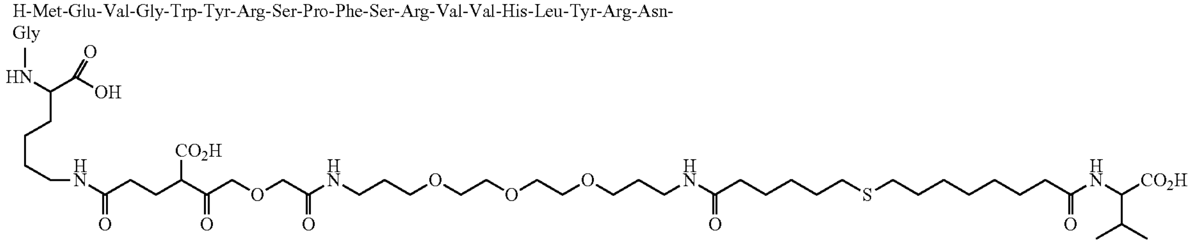

(xi)

(SEQ ID NO: 11)

H-Ser-Glu-Glu-Pro-Pro-Ile-Ser-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-
Asn-Arg

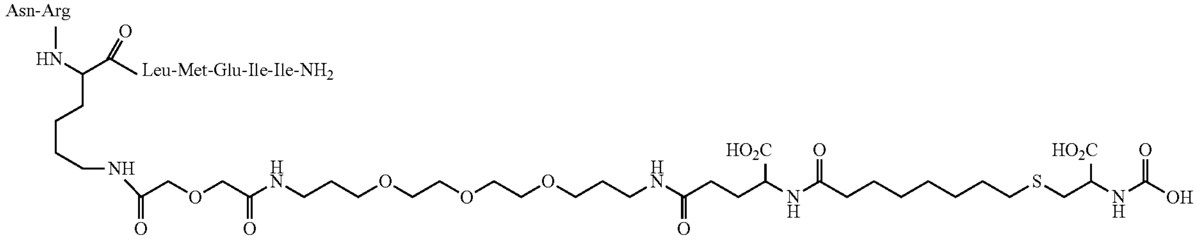

(xii)

(SEQ ID NO: 12)

H-Tyr-Pro-Ile

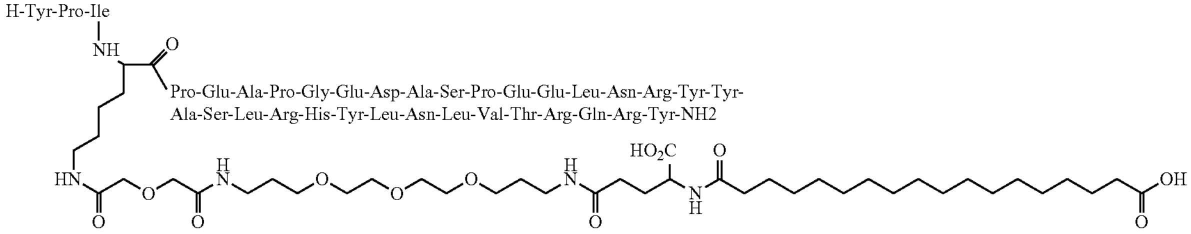

(xiii)

(SEQ ID NO: 13)

Fuzeon Modified at $Lys^{18}$:

N-acetyl-Tyr-Thr-Ser-Ile-His-Ser-Leu-Ile-Glu-Glu-Ser-Gln-Asn-Gln-Gln-Glu-Lys(X)-Asn-Glu-Gln-Gln-Leu-Leu-Glu-Leu-Asp-Lys-Trp-Ala-Ser-Leu-Trp-Asn-Trp-Phe-$NH_2$, where in X is 34-(tert-butoxycarbonyl)-1-(9H-fluoren-9-yl)-55,55-dimethyl-3,11,15,31,36,53-hexaoxo-2,13,20,23,26,54-hexaora-44-thia-4,10,16,30,35-pentaazahexapentacontane-5-carbonyl).

Pharmaceutical Composition

Another aspect of the invention relates to a pharmaceutical composition comprising a peptide, or a fragment thereof, or a variant thereof, as described herein admixed with a pharmaceutically acceptable excipient, diluent or carrier.

Even though the peptides of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant (s), suspending agent(s), coating agent(s), solubilising agent (s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders. An alternative means of transdermal administration is by use of a skin patch.

Compositions may be formulated in unit dosage form, i.e., in the form of discrete portions containing a unit dose, or a multiple or sub-unit of a unit dose.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case.

There can of course be individual instances where higher or lower dosage ranges are merited, and such are within the scope of this invention.

The present invention is further described by way of the following non-limiting examples.

EXAMPLES

Abbreviations

DCM dichloromethane
Hex hexane
TFA trifluoroacetic acid
RE rotary evaporation
RT room temperature
DMF dimethyl formamide
MeOH methanol
EtAc ethyl acetate
DMAP dimethylamino pyridine
DEE diethyl ether
PE petroleum ether
IPA isopropyl alcohol
NMP N-methyl pyrrolidone
HOBt hydroxybenzotriazole
DIC N,N'-diisopropylcarbodiimide
DTT dithiothreitol
TES triethylsilyl
HOSu N-hydroxysuccinimide
DCC N,N'-dicyclhfexyicarbodiimide
DIPEA N,N-diisopropylethylamine

Example 1: General Method for the Synthesis of Side Chain Modified Diamino Acid Derivatives with the General Formula 1 in Aqueous Solution by the Acylation Fmoc-Lys-OH To 18.4 g Fmoc-Lys-OH 200 ml Dioxan/10%-$NaHCO_3$ (1:1) were added. The obtained mixture was then cooled to 0-5° C. and then equimolar amounts of Z—$(Y)_b$—OH in 100 ml dioxan were added and the mixture was stirred for 2 h at 0-5° C. and 2 h at RT. The mixture was then diluted with 0.1 N—HCl and extracted with EtAc. The organic layer was then washed with 5%-$NaHCO_3$, $H_2O$, 0.1 N—HCl, $H_2O$ and brine, dried over anhydrous $Na_2SO_4$ and concentrated in the RE. The obtained oily product precipitated by the addition of DEE or petroleum ether or water. The obtained solid was filtered and washed with DEE or PE or water and dried in vacuum. Yield 60-95%.

Example 2: General Method for the Synthesis of Side Chain Modified Diamino Acid Derivatives with the General Formula 1 in Organic Solution by the Acylation of Fmoc-Lys-OH To a suspension of 18.4 g Fmoc-Lys-OH in 200 ml DCM 5.4 ml $Me_3SiCl$ were added at 0° C. and stirred for 3 h. Then 12.9 ml DIPEA were added and stirred for additional 30 min. Then a solution of equimolar amounts of Z—$(Y)_b$—OH, EDAC·HCl and HOSu in 100 ml anhydrous DMF were added and the mixture was stirred for 4 h at 10-15° C. The mixture was then diluted with 1N—HCl and extracted with EtAc. The organic layer was then washed with 5%-$NaHCO_3$, $H_2O$, 0.1N—HCl, $H_2O$ and brine, dried over anhydrous $Na_2SO_4$ and concentrated in the RE. The obtained oily products precipitated by the addition of DEE or petroleum ether or water. The obtained solids were filtered washed with DEE and hexane and dried in vacuum. Yield: 65-95%.

Example 3: Synthesis of N-Trityl-glutamic Acid α-tert-butyl ester (Trt-Glu-OtBu). Formula Nr. 2'-1

2'-1

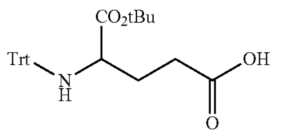

40.6 g H-Glu-(OtBu) were suspended in 400 ml DCM and cooled to 0° C. Then 21.7 g chlorotrimethylsilane were added dropwise and the mixture was stirred until a clear solution was obtained. Then 52 g DIPEA were added followed by 56 g Trt-Cl and the mixture was stirred for additional 2 h at 0° C. and warmed up to RT and stirred farther for additional 2 h. Then 20 ml MeOH were added and the mixture was concentrated in vacuum and then 500 ml DEE were added and the product was extracted and purified by acidic-basic extraction. The organic solution was concentrated in vacuum and the Trt-Glu-OtBu was obtained as syrup. Yield: 86.0 g (76.7%). The obtained syrup can be converted to solid diethylammonium salt by dissolving it in 350 ml DEE and adding to the solution 15 g DEA.

Example 4: Synthesis of Trt-Glu(OSu)-OtBu. Formula Nr. 2-1

2-1

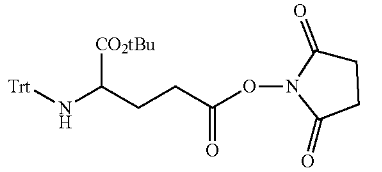

44.0 g of the Trt-Glu-OtBu in the syrup form were dissolved in 125 g THF and cooled to 10° C. Then 20.6 g DCC in 125 ml THF were added and the solution was stirred for 3 h at RT. Then 0.5 g AcOH and 0.5 ml $H_2O$ were added and the mixture was stirred for additional 1 h and filtered. The obtained solution was concentrated in the RE. A yellowish solid precipitated by the addition of DEE/hexane, filtered and dried in vacuum.

Example 5: Synthesis in Aqueous Solution of 2-(((9H-fluoren-9-yl)methoxy)carbonylamino)-6-(5-tert-butoxy-5-oxo-4-(tritylamino)pentanamido) hexanoic acid [Fmoc-Lys(Trt-Glu-OtBu)-OH, Formula Nr. 13-1 starting from Fmoc-Lys-OH Formula 13-1

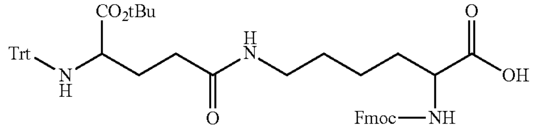

To 18.4 g Fmoc-Lys-OH 200 ml Dioxan/10%-$NaHCO_3$ (1:1) were added. The obtained mixture was then cooled to 0-5° C. and then 27.2 g Trt-Glu(OSu)-OtBu in 100 ml dioxan were added and the mixture was stirred for 2 h at 0-5° C. and 2 h at RT. The mixture was then diluted with 5% citric acid and extracted with EtAc. The organic layer was then washed with 5%-$NaHCO_3$, $H_2O$, 3% citric acid, $H_2O$) and brine, dried over anhydrous $Na_2SO_4$ and concentrated in the RE. The obtained oily product precipitated by the addition of DEE. The obtained solid was filtered washed with DEE and hexane and dried in vacuum. Yield 34.7 g=87.3%. With a melting range of 85-105° C. (decomposition).

Example 6: Synthesis in Organic Solution of 2-(((9H-fluoren-9-yl)methoxy)carbonylamino)-6-(5-tert-butoxy-5-oxo-4-(tritylamino)pentanamido) hexanoic acid [Fmoc-Lys(Trt-Glu-OtBu)-OH, Formula Nr. 13-1 starting from Fmoc-Lys-OH Formula 13-1

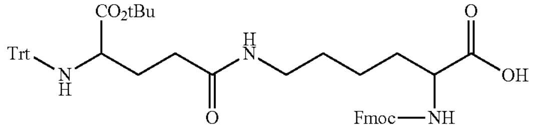

To a suspension of 18.4 g Fmoc-Lys-OH in 200 ml DCM 5.4 ml $Me_3SiCl$ were added at 0° C. and stirred for 3 h. Then 12.9 ml DIPEA were added and stirred for additional 30 min. Then 27.2 g Trt-Glu(OSu)-OtBu in 100 ml anhydrous DMF were added and the mixture was stirred for 4 h at 10-15° C. The mixture was then diluted with 5% citric acid and extracted with EtAc. The organic layer was then washed with 5%-$NaHCO_3$, $H_2O$, 3% citric acid, $H_2O$) and brine, dried over anhydrous $Na_2SO_4$ and concentrated in the RE. The obtained oily product precipitated by the addition of DEE. The obtained solid was filtered washed with DEE and hexane and dried in vacuum. Yield 35.7 g=89.8%. With a melting range of 85-105° C. (decomposition).

Example 7: Synthesis of (4-polystyrylphenyl)(p-tolyl)methyl 2-(((9H-fluoren-9-yl)methoxy)carbonylamino)-6-(5-tert-butoxy-5-oxo-4-(tritylamino) pentanamido)hexanoate [Fmoc-Lys(Trt-Glu-OtBu)-O-4-methylbenzhydryl-polystyryl ester], Formula Nr. 19-1

Formula 19-1

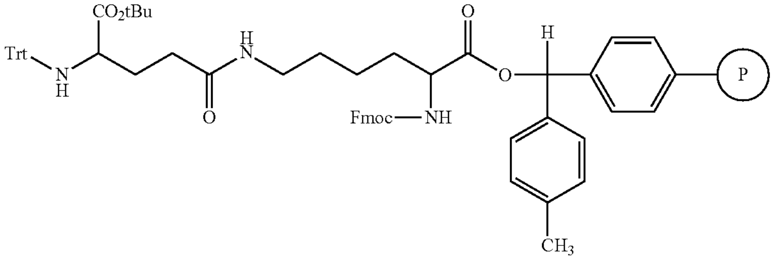

To a suspension of 100 g (170 mmol) 4-methyl-polystyryl bromide resin in 1 Lt DME 80 g (100.0 mmol) Fmoc-Lys (Trt-Glu-OtBu)-OH and 56 g DIPEA were added and the mixture was shacked for 12 h at RT. Then 100 ml MeOH were added and the mixture was shacked for additional 4 h at RT. The obtained resin was then washed with DCM/MeOH/DIPEA (85:10:5), DMF, iPrOH and hexane and dried in vacuum. Yield 143.4 g with a total loading of 43.0 mmol Fmoc-groups (43%) which were determined spectrophotometrically.

Example 8: Synthesis of (2-chlorophenyl)(phenyl)(p-polystyrylphenyl)methyl 2-(((9H-fluoren-9-yl)methoxy)carbonylamino)-6-(5-tert-butoxy-5-oxo-4-(tritylamino)pentanamido)hexanoate [Fmoc-Lys(Trt-Glu-OtBu)-O-2-chloro trityl-polystyryl ester], Formula Nr. 19-2

Formula 19-2

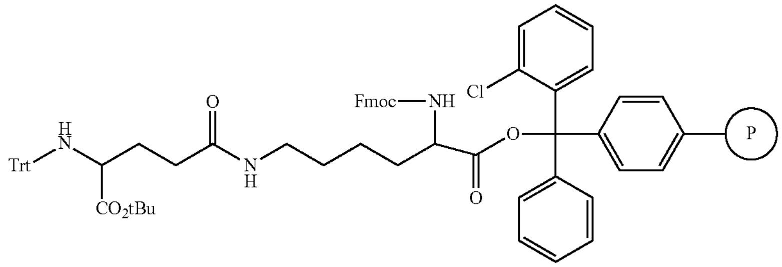

To a suspension of 100.0 g (160 mmol) 2-chlorotrityl-polystyryl chloride resin in 1.0 Lt DCM 80.0 g (100 mmol) Fmoc-Lys(Trt-Glu-OtBu)-OH and 56 g DIPEA were added and the mixture was shacked for 3 h at RT. Then 50 ml MeOH were added and the mixture was shacked for additional 1 h at RT. The obtained resin was then washed with DCM/MeOH/DIPEA (85:10:5), DMF, iPrOH and hexane and dried in vacuum. Yield 170.1 g with a total loading of 0.65 mmol Fmoc-groups (80%) which were determined spectrophotometrically.

Example 9: 1-tert-butyl 5-(2-chlorophenyl)(phenyl)(p-polystyrylphenyl)methyl 2-aminopentanedioate [H-Glu(2-chlorotrityl-polystyryl ester)-OtBu], Formula Nr. 18-1

Formula 18-1

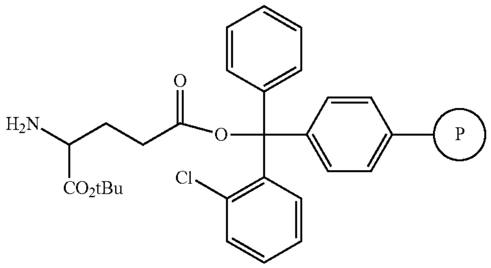

100 g (160 mmol) of CTC-chloride resin in 1 Lt DCM were esterified with 43 g (1.0 mol) Fmoc-L-Glu-OtBu under standard conditions and the Fmoc-group was removed subsequently. Yield 130.3 g with a total loading of 81.2 mmol Fmoc-groups (81%) which were determined spectrophotometrically.

Example 10: Synthesis of Myristoyl-Glu-OtBu, Formula Nr. 2'-2

Formula 2'-2

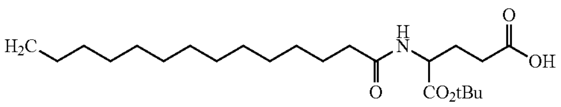

To a suspension of 0.78 g (0.63 mmol) of H-Glu(2-chloro trityl-polystyryl ester)-OtBu in 6 ml DMF were added 0.23 g (1 mmol) myristic acid, 0.15 g DIC and 0.15 g HOBt and the mixture was shacked for 4 h at RT. The resin was then filtered and washed 4× with DMF and 6× with DCM. Then the resin was treated 6× with 1% TFA and the combined filtrates were extracted with water and concentrated in the RE with the gradual addition of hexanes. The precipitated product was filtered, washed with hexanes and dried in vacuum. Yield: 0.28 g (95%) of an amorphous solid.

Example 11 (A): 2-(((9H-fluoren-9-yl)methoxy) carbonylamino)-6-(5-tert-butoxy-5-oxo-4-tetradecanamidopentanamido)hexanoic acid [Fmoc-Lys (Myr-Glu-OtBu)-OH] Formula Nr. 1-1

Formula 1-1

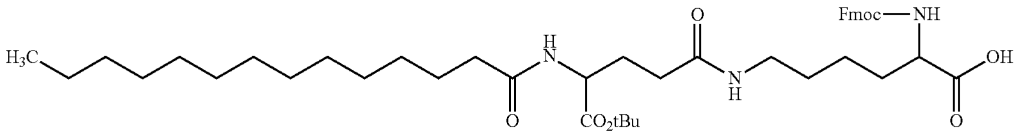

A mixture of 5.39 g 1-tert-butyl 5-(2,5-dioxopyrrolidin-1-yl) 2-tetradecanamidopentanedioate in 20 ml DMF were reacted with 4.05 g (10 mmol) of 2-(((9H-fluoren-9-yl) methoxy)carbonylamino)-6-aminohexanoic acid hydrochloride and 2.58 g (20 mmol) DIPEA was stirred for 4 h at RT. To this product mixture brine and EtAc were added and after a standard work up 6.65 g (87%) of the product were obtained.

(B): 2-(((9H-fluoren-9-yl)methoxy)carbonylamino)-6-(5-tert-butoxy-5-oxo-4-palmitamidopentanamido) hexanoic acid [Fmoc-Lys(Pal-Glu-OtBu)-OH] Formula 1-2

Example 12: 5-tert-butoxy-5-oxo-4-palmitamidopentanoic acid. Formula Nr. 2'-3 (Palmitoyl-Glu-OtBu) Molecular Weight: 441.6

Formula 2'-3

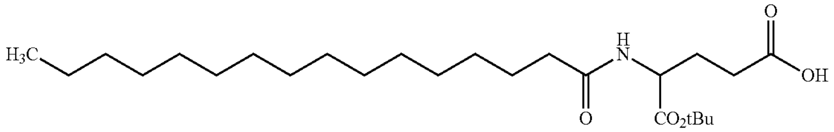

To suspension of 0.78 g (0.63 mmol) of H-Glu(2-chloro trityl-polystyryl ester)-OtBu in 6 ml DMF were added 0.26 g (1 mmol) palmitic acid, 0.15 g DIC and 0.15 g HOBt and the mixture was shacked for 4 h at RT. The resin was then filtered and washed 4× with DMF and 6× with DCM. Then the resin was treated 6× with 1% TFA and the combined filtrates were extracted with water and concentrated in the RE with the gradual addition of hexanes. The precipitated product was filtered, washed with hexanes and dried in vacuum. Yield: 0.28 g (95%) of an amorphous solid.

Example 13: 1-(9H-fluoren-9-yl)-3,19-dioxo-2,8,11,14,21-pentaoxa-4,18-diazatricosan-23-oic acid. Formula Nr. 12-1

Molecular Weight: 558.6

Formula 12-1

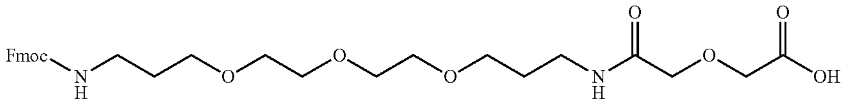

To 220.3 g (1 Mol) of 3,3'-(2,2'-oxybis(ethane-2,1-diyl) bis(oxy))dipropan-1-amine (BASF) in 600 ml DCM 217.2 g chlorotrimethylsilane and 258.0 g DIPEA were added at 5° C. and stirred for 3 h at RT. The obtained mixture was cooled at 3° C. and then a solution of 175.0 g (676.5 mmol) of Fmoc-chloride in 1200 ml DCM were added drop wise within 2 h. and stirred then for additional 3 h at RT. The mixture was concentrated in the RE and partitioned between water and DEE. The water layer was extracted one more time with DEE and to the obtained water phase solid sodium carbonate and solid NaCl were added until the formed (9H-fluoren-9-yl)methyl 3-(2-(2-(3-aminopropoxy)ethoxy) ethoxy) propylcarbamate was separated as a yellowish oil which was extracted in DCM. The obtained DCM solution was then concentrated in the RE and the oily residue was dissolved in 750 ml DMF. Then 58.5 g (0.5 Mol) of 1,4-dioxane-2,6-dione (glycolic acid anhydride) and 130 g DIPEA were added and the mixture was warmed to 60° C. and stirred for 3 h. After a standard work up 215.4 g (38.5%) of the 1-(9H-fluoren-9-yl)-3,19-dioxo-2,8,11,14,21-pentaoxa-4,18-diazatricosan-23-oic acid were obtained.

Example 14: 1-(9H-fluoren-9-yl)-3,19-dioxo-2,8,11,14-tetraoxa-4,18-diazadocosan-22-oic Acid new method of preparation. Formula Nr. 12-2

Molecular Weight: 542.6

Formula 12-2

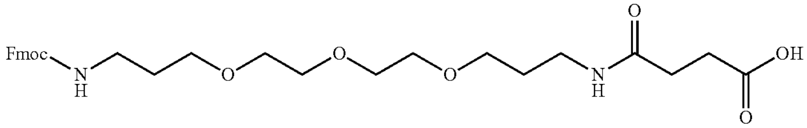

To 220.3 g (1 Mol) of 3,3'-(2,2'-oxybis(ethane-2,1-diyl) bis(oxy))dipropan-1-amine (BASF) in 600 ml DCM 217.2 g chlorotrimethylsilane and 258.0 g DIPEA were added at 5° C. and stirred for 3 h at RT. The obtained mixture was cooled at 3° C. and then a solution of 175.0 g (676.5 mmol) of Fmoc-chloride in 1200 ml DCM were added drop wise within 2 h. and stirred then for additional 3 h at RT. The mixture was concentrated in the RE and partitioned between water and DEE. The water layer was extracted one more time with DEE and to the obtained water phase solid sodium carbonate and solid NaCl were added until the formed (9H-fluoren-9-yl)methyl 3-(2-(2-(3-aminopropoxy)ethoxy) ethoxy) propylcarbamate was separated as a yellowish oil which was extracted in DCM. The obtained DCM solution was then concentrated in the RE and the oily residue was dissolved in 750 ml DMF. Then 50.0 g (0.5 Mol) of 1, dihydrofuran-2,5-dione (succinic acid anhydride) and 130 g DIPEA were added and the mixture was warmed to 60° C. and stirred for 3 h. After a standard work up 228.4 g (42.1%) of the 1-(9H-fluoren-9-yl)-3,19-dioxo-2,8,11,14-tetraoxa-4,18-diazadocosan-22-oic acid were obtained.

Example 15: (2-chlorophenyl)(phenyl)(polystyryl) methyl 1-(9H-fluoren-9-yl)-3-oxo-2,7,10-trioxa-4-azadodecan-12-oate. Formula Nr. 11-1

Formula 11-1

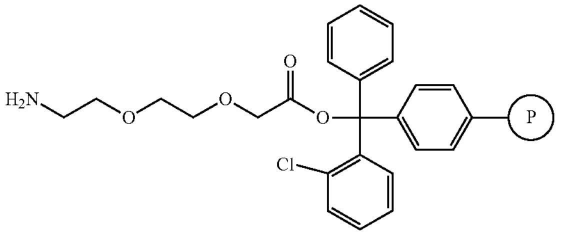

A suspension of 100.00 g (160 mmol) CTC-chloride resin in 1 Lt DCM was esterified under standard conditions with 38.5 g (100 mmol) of 1-(9H-fluoren-9-yl)-3,19-dioxo-2,8,11,14,21-pentaoxa-4,18-diazatricosan-23-oic acid and the Fmoc-group was removed subsequently. Yield: 115.5 g with a total loading of 79 mmol (79%).

Example 16: (2-chlorophenyl)(phenyl)(polystyryll) methyl 1-amino-15-oxo-4,7,10-trioxa-14-azaoctadecan-18-oate. Formula Nr. 12-3

Formula 12-3

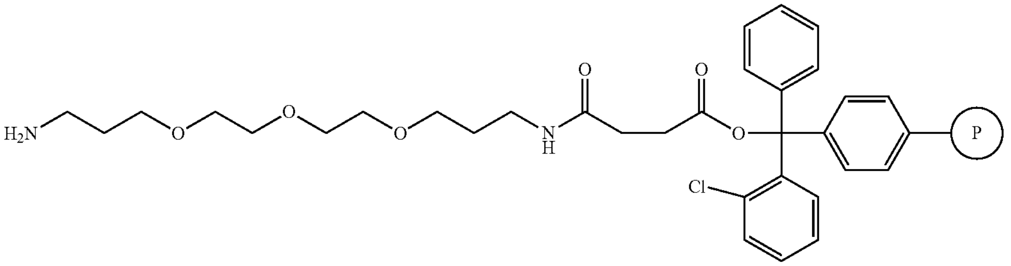

A suspension of 100.00 g (160 mmol) CTC-chloride resin in 1 Lt DCM was esterified under standard conditions with 54.3 g (100 mmol) of 1-(9H-fluoren-9-yl)-3,19-dioxo-2,8,11,14-tetraoxa-4,18-diazadocosan-22-oic acid and the Fmoc-group was removed subsequently. Yield: 117.7 g with a total loading of 84 mmol (79%).

Example 17: Synthesis of 1-(9H-fluoren-9-yl)-3,19-dioxo-2,8,11,14,21-pentaoxa-4,18-diazatricosan-23-oic Acid 2-chlorotrityl ester. Formula Nr. 12-4

Formula Nr. 12-4

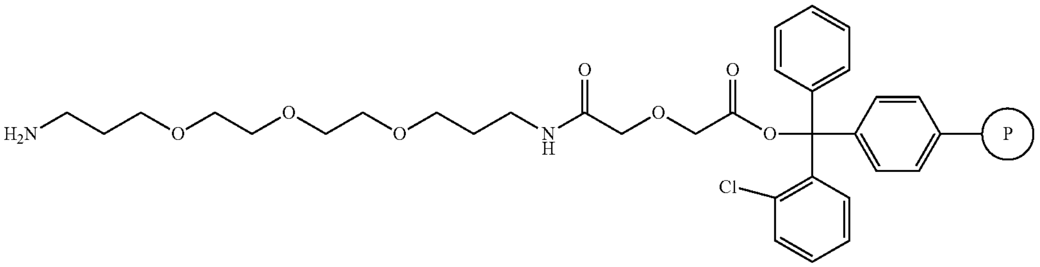

A suspension of 100.00 g (160 mmol) CTC-chloride resin in 1 Lt DCM was esterified under standard conditions with 55.8 g (100 mmol) of 1-(9H-fluoren-9-yl)-3,19-dioxo-2,8,11,14,21-pentaoxa-4,18-diazatricosan-23-oic acid and the Fmoc-group was removed subsequently. Yield: 128.0 g with a total loading of 88 mmol (88%).

Example 18: 1-tert-butyl 5-(2-chlorophenyl)(phenyl)(4-polystyrylphenyl)methyl 2-(1-(9H-fluoren-9-yl)-3,12-dioxo-2,7,10,16,19-pentaoxa-4,13-diazahenicosanamido)pentanedioate. Formula Nr. 18-2

A suspension of 1.00 g H-Glu(2-chlorotrityl-polystyryl ester)-OtBu (0.61 mmol) in 5 ml DMF was coupled with 0.38 g (1 mmol) of 1-(9H-fluoren-9-yl)-3-oxo-2,7,10-trioxa-4-azadodecan-12-oic acid, the Fmoc-group was subsequently removed as usual and a second coupling with the same quantity 1-(9H-fluoren-9-yl)-3-oxo-2,7,10-trioxa-4-azadodecan-12-oic acid was performed. After the standard washing and drying of the resin 1.45 g were obtained with a total loading of 0.58 mmol (95%).

Formula 18-2

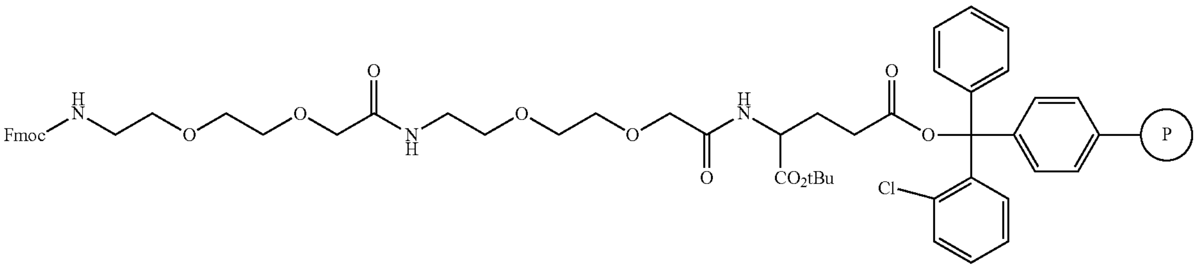

Example 19: 23-(tert-butoxycarbonyl)-1-(9H-fluoren-9-yl)-3,12,21-trioxo-2,7,10,16,19-pentaoxa-4,13,22-triazahexacosan-26-oic acid. Formula Nr. 2'-4

Molecular Weight: 715.8

Formula 2'-4

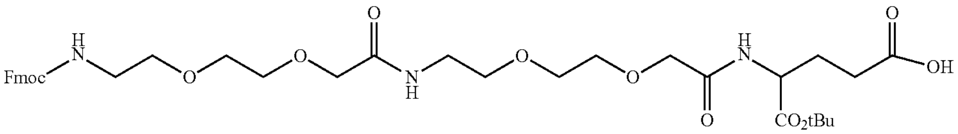

1.45 g (0.58 mmol) of the resin obtained according to the procedure described above were treated and worked up as usually in order to obtain the protected modifier. Yield 0.38 g (91.5%).

Example 20: 1-tert-butyl 5-(2-chlorophenyl)(phenyl)(4-polystyrylphenyl)methyl 2-(1-(9H-fluoren-9-yl)-3,19-dioxo-2,8,11,14-tetraoxa-4,18-diazadocosanamido)pentanedioate. Formula Nr. 18-3

Formula 18-3

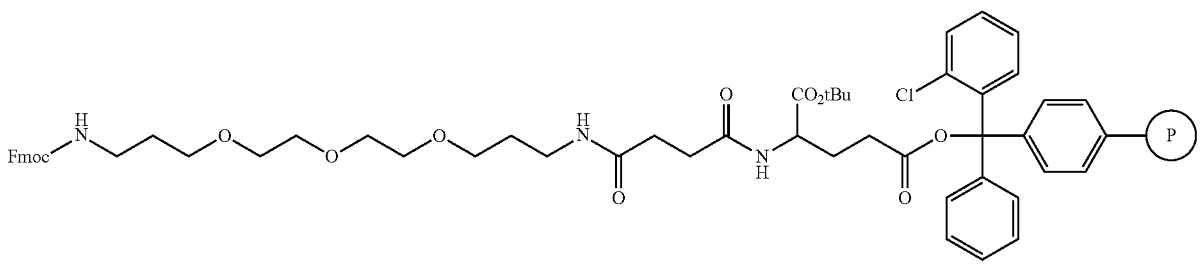

A suspension of 1.00 g H-Glu(2-chlorotrityl-polystyryl ester)-OtBu (0.61 mmol) in 5 ml DMF was coupled with 0.54 g (1 mmol) of 1-(9H-fluoren-9-yl)-3,19-dioxo-2,8,11,14-tetraoxa-4,18-diazadocosan-22-oic acid. After the standard washing and drying of the resin 1.74 g were obtained with a total loading of 0.59 mmol (96.7%).

Example 21: 24-(tert-butoxycarbonyl)-1-(9H-fluoren-9-yl)-3,19,22-trioxo-2,8,11,14-tetraoxa-4,18,23-triazaheptacosan-27-oic acid. Formula Nr. 2'-5

Molecular Weight: 727.8

Formula 2'-5

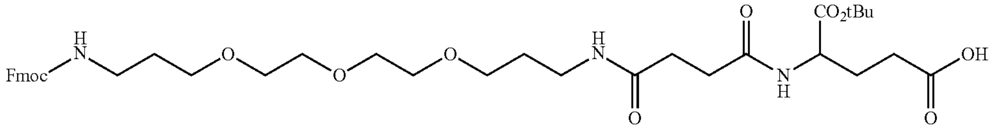

1.74 g (0.59 mmol) of the resin obtained according to the procedure described above were treated and worked up as usually in order to obtain the protected modifier. Yield 0.42 g (96.6%).

Example 22: 1-tert-butyl 5-(2-chlorophenyl)(phenyl)(4-polystyrylphenyl)methyl 2-(1-(9H-fluoren-9-yl)-3,19-dioxo-2,8,11,14,21-pentaoxa-4,18-diazatricosanamido)pentanedioate. Formula Nr. 18-4

18-4

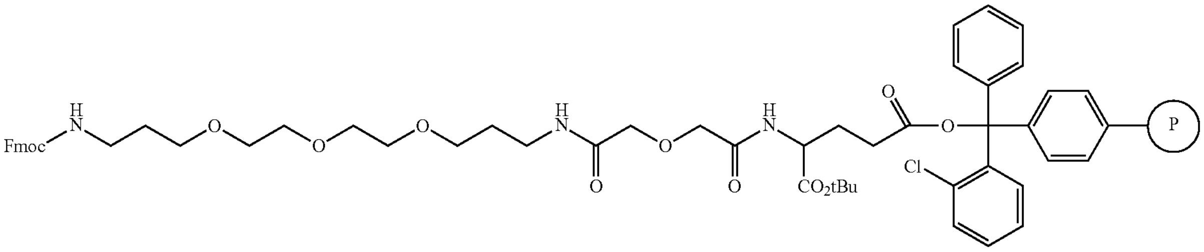

A suspension of 1.00 g H-Glu(OCTC-resin-OtBu (0.61 mmol) in 5 ml DMF was coupled with 0.56 g (1 mmol) of 1-(9H-fluoren-9-yl)-3,19-dioxo-2,8,11,14,21-pentaoxa-4,18-diazatricosan-23-oic acid. After the standard washing and drying of the resin 1.61 g were obtained with a total loading of 0.54 mmol (88.5%).

Example 23: 25-(tert-butoxycarbonyl)-1-(9H-fluoren-9-yl)-3,19,23-trioxo-2,8,11,14,21-pentaoxa-4,18,24-triazaoctacosan-28-oic acid. Formula Nr. 2'-6

Molecular Weight: 743.8

Formula 2'-6

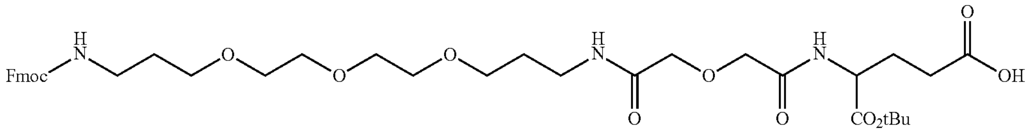

1.60 g (1 mmol) H-Glu(OCTC-resin)-OtBu were coupled with 1.12 g (2 mmol) of 1-(9H-fluoren-9-yl)-3,19-dioxo-2,8,11,14,21-pentaoxa-4,18-diazatricosan-23-oic acid. The protected modifier was then cleaved from the resin following the standard procedure. Yield: 0.71 g (95.46%).

Example 24: 5-(tert-butoxycarbonyl)-1-(9H-fluoren-9-yl)-3,8-dioxo-2,12,15-trioxa-4,9-diazaheptadecan-17-oic acid. Formula Nr. 11-2

Molecular Weight: 570.6

Formula 11-2

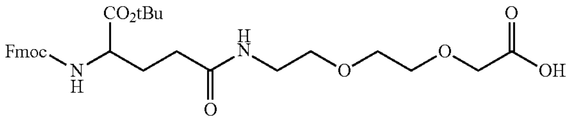

1.45 g (1.0 mmol) of the as described above obtained (2-chlorophenyl)(phenyl)(polystyryl)methyl 2-(2-(2-aminoethoxy)ethoxy)acetate was coupled with 0.85 g (2 mmol) Fmoc-Glu-OtBu. The resin was then treated according to the standard procedure for obtaining protected modifiers. Yield 0.52 g (91.1%).

Example 25: 5-(tert-butoxycarbonyl)-1-(9H-fluoren-9-yl)-3,8,17-trioxo-2,12,15,21,24-pentaoxa-4,9,18-triazahexacosan-26-oic acid. Formula Nr. 11-3

Molecular Weight: 715.8

Formula 11-3

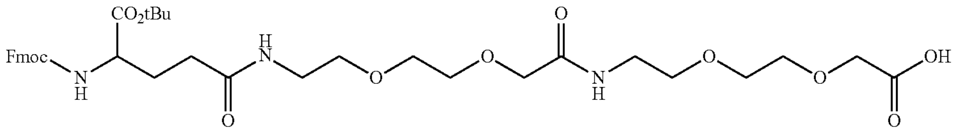

1.45 g (1.0 mmol) of the as described above obtained (2-chlorophenyl)(phenyl)(polystyryl)methyl 2-(2-(2-aminoethoxy)ethoxy)acetate were coupled with 0.77 g (2 mmol) of 1-(9H-fluoren-9-yl)-3-oxo-2,7,10-trioxa-4-azadodecan-12-oic acid, the Fmoc-group was then removed and the resin was coupled with 0.85 (2 mmol) Fmoc-Glu-OtBu. Then the resin was treated according to the general procedure to give the protected modifier. Yield: 0.69 g (96.4%).

Example 26: 5-(tert-butoxycarbonyl)-1-(9H-fluoren-9-yl)-3,8,24-trioxo-2,13,16,19,26-pentaoxa-4,9,23-triazaoctacosan-28-oic acid. Formula Nr. 12-5

Molecular Weight: 743.8

Formula 12-5

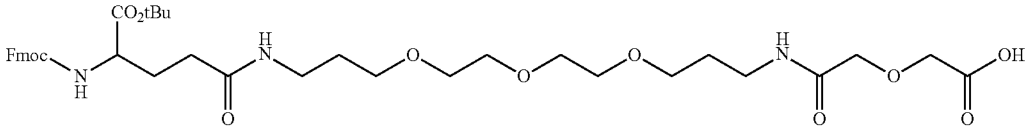

1.67 g (1 mmol) of the resin prepared according to the example above was treated with piperidine in order to remove the Fmoc-group. The obtained resin was then coupled with 0.85 g of Fmoc-Glu-OtBu and worked up to give the protected modifier. Yield: 0.65 g (87.4%).

Example 27: 5-(tert-butoxycarbonyl)-1-(9H-fluoren-9-yl)-3,8,24-trioxo-2,13,16,19-tetraoxa-4,9,23-triazaheptacosan-27-oic acid. Formula Nr. 12-6

Molecular Weight: 727.8

Formula 12-6

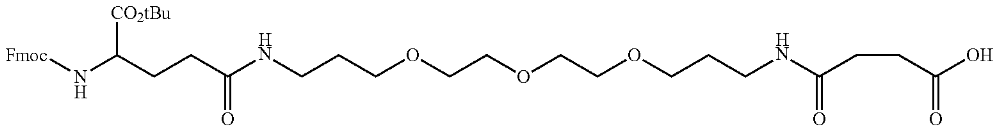

1.40 g (1 mmol) (2-chlorophenyl)(phenyl)(polystyryll) methyl 1-amino-15-oxo-4,7,10-trioxa-14-azaoctadecan-18-oate were coupled with 0.85 (2 mmol) g of Fmoc-Glu-OtBu and worked up to give the protected modifier. Yield: 0.69 g (94.8%).

Example 28: 4-(tert-butoxycarbonyl)-6,15-dioxo-8,11-dioxa-5,14-diazatriacontan-1-oic acid. Formula Nr. 2'-7

Molecular Weight: 586.8

Formula 2'-7

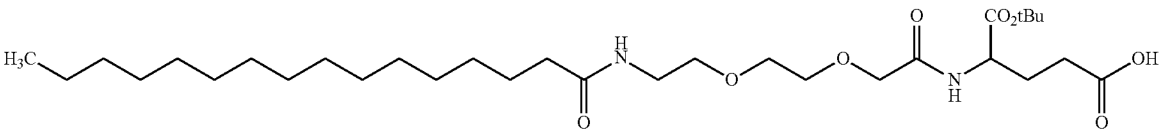

1.60 g (1 mmol) H-Glu(OCTC-resin)-OtBu were coupled sequentially with 0.72 g (2 mmol) of 1-(9H-fluoren-9-yl)-3-oxo-2,7,10-trioxa-4-azadodecan-12-oic acid and 0.51 g palmitic acid. The protected modifier was then cleaved from the resin following the standard procedure. Yield: 0.53 g (89.83%).

Example 29: 4-(tert-butoxycarbonyl)-6,15,24-trioxo-8,11,17,20-tetraoxa-5,14,23-triazanonatriacontan-1-oic acid. Formula Nr. 2'-8

Formula 2'-8

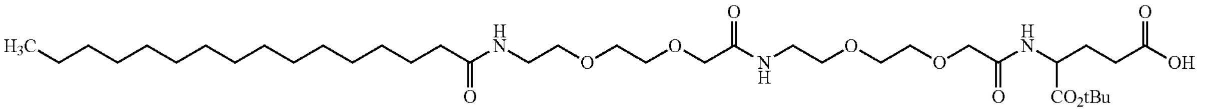

1.60 g (1 mmol) H-Glu(OCTC-resin)-OtBu were coupled sequentially with 0.72 g (2 mmol) of 1-(9H-fluoren-9-yl)-3-oxo-2,7,10-trioxa-4-azadodecan-12-oic acid, 0.72 g (2 mmol) of 1-(9H-fluoren-9-yl)-3-oxo-2,7,10-trioxa-4-azadodecan-12-oic acid and 0.51 g palmitic acid. The protected modifier was then cleaved from the resin following the standard procedure. Yield: 0.71 g (97.00%).

Example 30: 4-(tert-butoxycarbonyl)-6,10,26-trioxo-8,15,18,21-tetraoxa-5,11,25-triazahentetracontan-1-oic acid. Formula Nr. 2'-9

Formula 2'-9

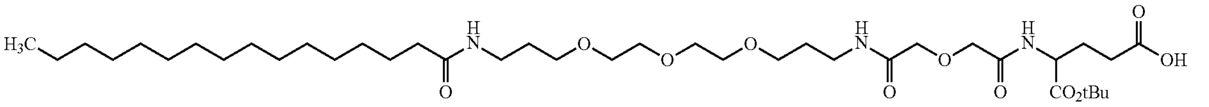

1.60 g (1.0 mmol) H-Glu(OCTC-resin)-OtBu were coupled sequentially with 1.12 g (2.0 mmol) of 1-(9H-fluoren-9-yl)-3-oxo-2,7,10-trioxa-4-azadodecan-12-oic acid and 0.51 g palmitic acid. The protected modifier was then cleaved from the resin following the standard procedure. Yield: 0.68 g (89.47%).

Example 31: 4-(tert-butoxycarbonyl)-6,9,25-trioxo-14,17,20-trioxa-5,10,24-triazatetracontan-1-oic acid. Formula Nr. 2'-10

Formula 2'-10

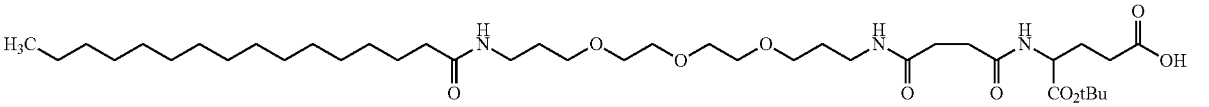

1.60 g (1.0 mmol) H-Glu(OCTC-resin)-OtBu were coupled sequentially with 1.09 g (2.0 mmol) of 1-(9H-fluoren-9-yl)-3,19-dioxo-2,8,11,14-tetraoxa-4,18-diazado-cosan-22-oic acid and 0.51 g palmitic acid. The protected modifier was then cleaved from the resin following the standard procedure. Yield: 0.71 g (95.43%).

Example 32: 13-(tert-butoxycarbonyl)-10,15-dioxo-3,6-dioxa-9,14-diazatriacontan-1-oic acid. Formula Nr. 11-4

Molecular Weight: 586.8

Formula 11-4

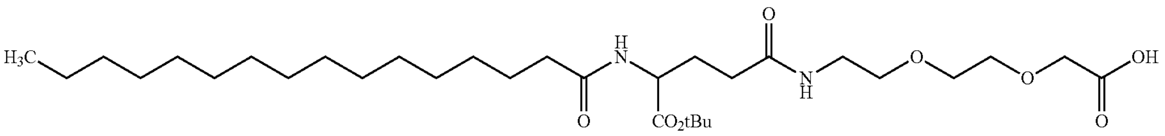

1.45 g (1 mmol) (2-chlorophenyl)(phenyl)(polystyryl) methyl 2-(2-(2-aminoethoxy)ethoxy)acetate were coupled sequentially with 0.85 g (2.0 mmol) Fmoc-Glu-OtBu and with 0.51 (2.00 mmol) g palmitic acid. The protected modifier was then cleaved from the resin following the standard procedure. Yield: 0.51 g (86.91%).

Example 33: 24-(tert-butoxycarbonyl)-12,21,26-trioxo-3,6,11,14,17-pentaoxa-9,20,25-triazahentetracontan-1-oic acid. Formula Nr. 11-5

Molecular Weight: 762.0

Formula 11-5

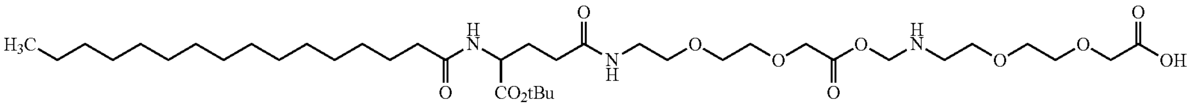

1.45 g (1 mmol) (2-chlorophenyl)(phenyl)(polystyryl) methyl 2-(2-(2-aminoethoxy)ethoxy)acetate were coupled sequentially with 0.77 g (2 mmol) 1-(9H-fluoren-9-yl)-3-oxo-2,7,10-trioxa-4-azadodecan-12-oic acid, with 0.85 g (2.0 mmol) Fmoc-Glu-OtBu and with 0.51 (2.00 mmol) g palmitic acid. The protected modifier was then cleaved from the resin following the standard procedure. Yield: 0.72 g (94.49%).

Example 34: 24-(tert-butoxycarbonyl)-5,21,26-trioxo-3,10,13,16-tetraoxa-6,20,25-triazahentetracontan-1-oic acid. Formula Nr. 12-7

Molecular Weight: 760.0

Formula 12-7

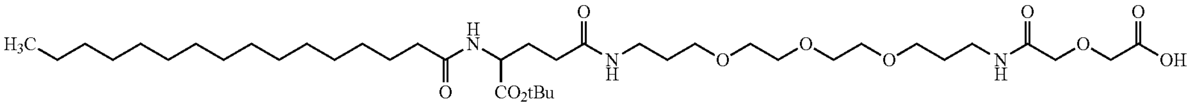

1.65 g (1 mmol). (2-chlorophenyl)(phenyl)(polystyryl) methyl 1-(9H-fluoren-9-yl)-3,19-dioxo-2,8,11,14,21-pentaoxa-4,18-diazatricosan-23-oate were coupled sequentially with 0.85 g (2 mmol) Fmoc-Glu-OtBu and with 0.51 g palmitic acid. The protected modifier was then cleaved from the resin following the standard procedure. Yield: 0.69 g (90.79%).

Example 35: 23-(tert-butoxycarbonyl)-4,20,25-trioxo-9,12,15-trioxa-5,19,24-triazatetracontan-1-oic acid. Formula Nr. 12-8

Molecular Weight: 744.0

Formula 12-7

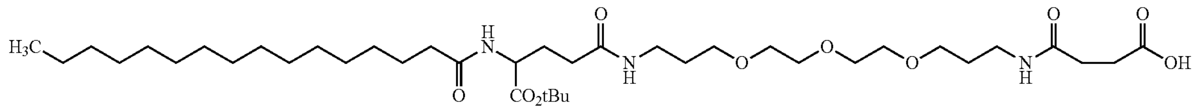

1.40 g (1 mmol) (2-chlorophenyl)(phenyl)(polystyryll) methyl 1-amino-15-oxo-4,7,10-trioxa-14-azaoctadecan-18-oate were coupled were coupled sequentially with 0.85 g (2 mmol) Fmoc-Glu-OtBu and with 0.51 g palmitic acid. The protected modifier was then cleaved from the resin following the standard procedure. Yield: 0.69 g (92.74%).

Example 36: 5-tert-butoxy-4-(8-(octylthio)octanamido)-5-oxopentanoic acid. Formula Nr. 2'-11

Formula 2'-11

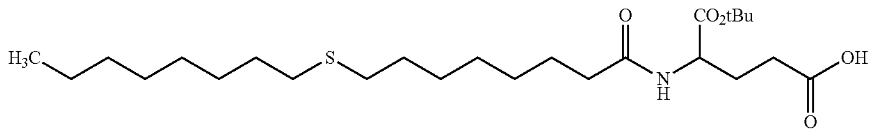

1.6 g (1.00) of H-Glu(OCTC-resin)-OtBu were coupled with 0.29 g (1 mmol) 8-(octylthio)octanoic acid (obtained by the reaction of 1-octanethiol and 8-bromooctanoic acid. The protected modifier was then cleaved from the resin following the standard procedure. Yield: 0.39 g (82.38%).

Example 37: 4-(tert-butoxycarbonyl)-6,15-dioxo-8,11-dioxa-23-thia-5,14-diazahentriacontan-1-oic acid. Formula Nr. 2'-12

Molecular Weight: 618.9

Formula 2'-12

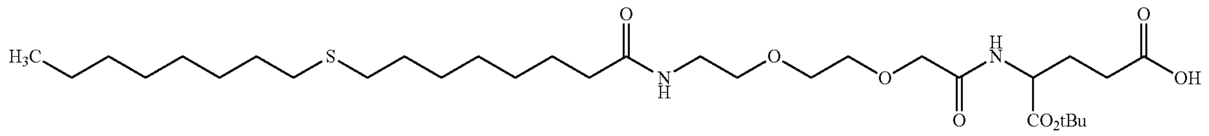

1.60 g (1 mmol) H-Glu(OCTC-resin)-OtBu were coupled sequentially with 0.77 g (2 mmol) of 1-(9H-fluoren-9-yl)-3-oxo-2,7,10-trioxa-4-azadodecan-12-oic acid and 0.58 g (2 mmol) of 8-(octylthio)octanoic acid. The protected modifier was then cleaved from the resin following the standard procedure. Yield: 0.58 g (93.71%).

Example 38: 4-(tert-butoxycarbonyl)-6,15,24-trioxo-8,11,17,20-tetraoxa-32-thia-5,14,23-triazatetracontan-1-oic acid. Formula Nr. 2'-13

Molecular Weight: 764.0

Formula 2'-13

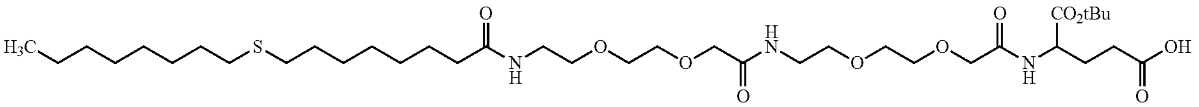

1.60 g (1 mmol) H-Glu(OCTC-resin)-OtBu were coupled sequentially with 0.77 g (2 mmol) of 1-(9H-fluoren-9-yl)-3-oxo-2,7,10-trioxa-4-azadodecan-12-oic acid, with 0.77 g (2 mmol) of 1-(9H-fluoren-9-yl)-3-oxo-2,7,10-trioxa-4-azadodecan-12-oic acid and 0.58 g (2 mmol) of 8-(octylthio) octanoic acid. The protected modifier was then cleaved from the resin following the standard procedure. Yield: 0.75 g (98.17%).

Example 39: 4-(tert-butoxycarbonyl)-6,10,26-trioxo-8,15,18,21-tetraoxa-34-thia-5,11,25-triazadotetracontan-1-oic acid. Formula Nr. 2'-14

Molecular Weight: 792.1

Formula 2'-14

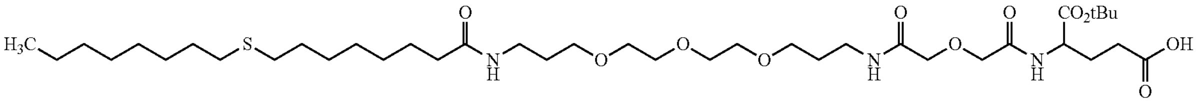

1.60 g (1 mmol) H-Glu(OCTC-resin)-OtBu were coupled sequentially with 1.12 g (2 mmol) of 1-(9H-fluoren-9-yl)-3,19-dioxo-2,8,11,14,21-pentaoxa-4,18-diazatricosan-23-oic acid and 0.58 g (2 mmol) of 8-(octylthio)octanoic acid. The protected modifier was then cleaved from the resin following the standard procedure. Yield: 0.79 g (92.16%).

Example 40: 4-(tert-butoxycarbonyl)-6,9,25-trioxo-14,17,20-trioxa-33-thia-5,10,24-triazahentetracontan-1-oic acid. Formula Nr. 2'-15

Molecular Weight: 776.1

Formula 2'-15

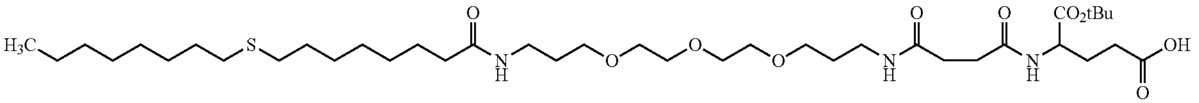

1.60 g (1 mmol) H-Glu(OCTC-resin)-OtBu were coupled sequentially with 1.08 g (2 mmol) of 1-(9H-fluoren-9-yl)-3,19-dioxo-2,8,11,14-tetraoxa-4,18-diazadocosan-22-oic acid and 0.58 g (2 mmol) of 8-(octylthio)octanoic acid. The protected modifier was then cleaved from the resin following the standard procedure. Yield: 0.79 g (92.16%).

Example 41: 13-(tert-butoxycarbonyl)-10,15-dioxo-3,6-dioxa-23-thia-9,14-diazahentriacontan-1-oic acid. Formula Nr. 11-6

Molecular Weight: 618.9

Formula 11-6

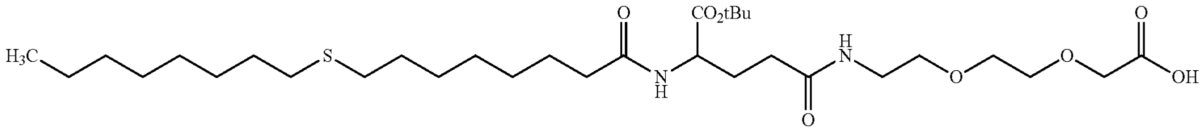

1.46 g (1 mmol) of (2-chlorophenyl)(phenyl)(polystyryl) methyl 2-(2-(2-aminoethoxy)ethoxy)acetate were coupled sequentially with 0.85 g of Fmoc-Glu-OtBu (2 mmol) and 0.58 g (2 mmol) of 8-(octylthio)octanoic acid. The protected modifier was then cleaved from the resin following the standard procedure. Yield: 0.55 g (89.00%).

Example 42: 22-(tert-butoxycarbonyl)-10,19,24-trioxo-3,6,12,15-tetraoxa-32-thia-9,18,23-triazatetracontan-1-oic acid. Formula Nr. 11-7

Molecular Weight: 764.0

Formula 11-7

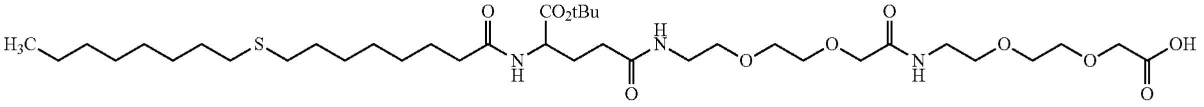

1.46 g (1 mmol) of (2-chlorophenyl)(phenyl)(polystyryl) methyl 2-(2-(2-aminoethoxy)ethoxy)acetate were coupled sequentially with 0.77 g (2 mmol) 1-(9H-fluoren-9-yl)-3-oxo-2,7,10-trioxa-4-azadodecan-12-oic acid, with 0.85 g (2 mmol) of Fmoc-Glu-OtBu and 0.58 g (2 mmol) of 8-(octylthio)octanoic acid. The protected modifier was then cleaved from the resin following the standard procedure. Yield: 0.70 g (93.83%).

Example 43: 24-(tert-butoxycarbonyl)-5,21,26-trioxo-3,10,13,16-tetraoxa-34-thia-6,20,25-triazadotetracontan-1-oic acid. Formula Nr. 12-9

Molecular Weight: 792.1

Formula 12-9

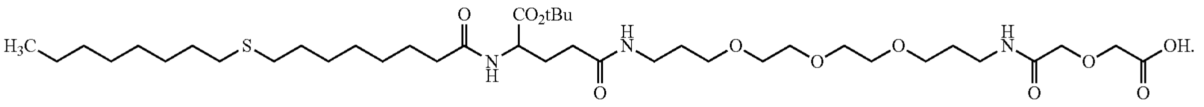

1.45 g (1 mmol) (2-chlorophenyl)(phenyl)(polystyryl) methyl 19-amino-5-oxo-3,10,13,16-tetraoxa-6-azanonadecan-1-oate were coupled sequentially with 0.85 g (2 mmol) of Fmoc-Glu-OtBu and 0.58 g (2 mmol) of 8-(octylthio) octanoic acid. The protected modifier was then cleaved from the resin following the standard procedure. Yield: 0.77 g (97.21%).

Example 44: 23-(tert-butoxycarbonyl)-4,20,25-trioxo-9,12,15-trioxa-33-thia-5,19,24-triazahentetracontan-1-oic acid. Formula Nr. 12-10

Molecular Weight: 776.1

Formula 12-10

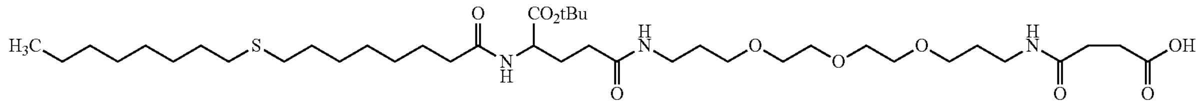

1.40 g (1 mmol) (2-chlorophenyl)(phenyl)(polystyryll) methyl 1-amino-15-oxo-4,7,10-trioxa-14-azaoctadecan-18-oate were coupled were coupled sequentially with 0.85 g (2 mmol) Fmoc-Glu-OtBu and with 0.58 g 8-(octylthio)octanoic acid. The protected modifier was then cleaved from the resin following the standard procedure. Yield: 0.73 g (93.99%).

Example 45: 5-tert-butoxy-4-(16-tert-butoxy-16-oxohexadecanamido)-5-oxopentanoic acid. Formula Nr. 2'-16

Molecular Weight: 527.7

Formula 2'-16

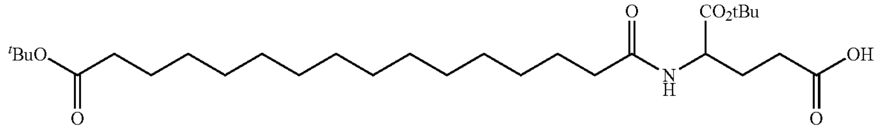

1 g (0.7 mmol) of L-glutamic acid α-(2-chlorotrityl-polystyryl) ester in 6 ml DMF were reacted with 0.34 g (1.00 mmol) of tert-butyloxycarbonyldecapentanoic acid (prepared by tert butylation of the corresponding monomethyl ester followed by saponification), 0.15 g DIC and 0.15 g HOBt. The mixture was stirred for 4 h at RT. The resin was then filtered and washed 4× with DMF and 6× with DCM. Then the resin was treated 6× with 1% TFA and the combined filtrates were extracted with water and concentrated in the RE with the gradual addition of hexanes. The precipitated product was filtered, washed with hexanes and dried in vacuum. Yield: 0.32 g (86.2%) of an amorphous solid.

Example 46: 29,29-dimethyl-10,27-dioxo-3,6,28-trioxa-9-azatriacontan-1-oic acid. Formula Nr. 11-8

Molecular Weight: 515.7

Formula 11-8

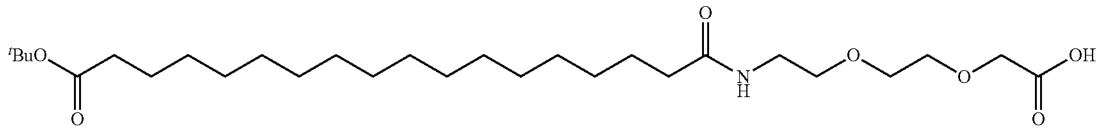

1.46 g (1 mmol) (2-chlorophenyl)(phenyl)(polystyryl) methyl 2-(2-(2-aminoethoxy)ethoxy)acetate were coupled with 0.74 g (2 mmol) of 18-tert-butoxy-18-oxooctadecanoic acid. The protected modifier was then cleaved from the resin following the standard procedure. Yield: 0.44 g (85.02%).

Example 47: 38,38-dimethyl-10,19,36-trioxo-3,6,12,15,37-pentaoxa-9,18-diazanonatriacontan-1-oic acid. Formula Nr. 11-9

Molecular Weight: 660.9

Formula 11-9

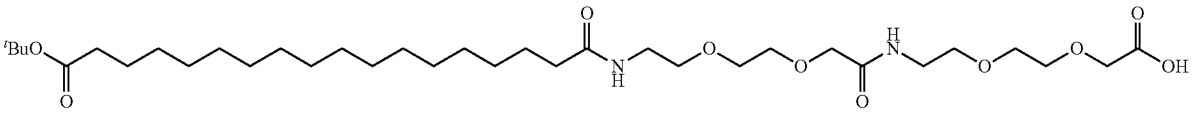

1.46 g (1 mmol) (2-chlorophenyl)(phenyl)(polystyryl) methyl 2-(2-(2-aminoethoxy)ethoxy)acetate were coupled sequentially with 0.77 g (2 mmol) of 1-(9H-fluoren-9-yl)-3-oxo-2,7,10-trioxa-4-azadodecan-12-oic acid and with 0.74 g (2 mmol) of 18-tert-butoxy-18-oxooctadecanoic acid. The protected modifier was then cleaved from the resin following the standard procedure. Yield: 0.66 g (92.03%).

Example 48: 40,40-dimethyl-5,21,38-trioxo-3,10,13,16,39-pentaoxa-6,20-diazahentetracontan-1-oic acid. Formula Nr. 12-11

Molecular Weight: 688.9

Formula 12-11

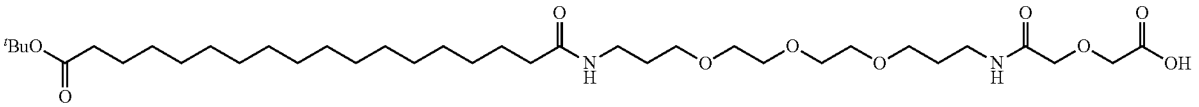

1.45 g (1 mmol) of (2-chlorophenyl)(phenyl)(polystyryl) methyl 19-amino-5-oxo-3,10,13,16-tetraoxa-6-azanonadecan-1-oate were coupled with 0.74 g (2 mmol) of 18-tert-butoxy-18-oxooctadecanoic acid. The protected modifier was then cleaved from the resin following the standard procedure. Yield: 0.65 g (94.35%).

Example 49: 2,2-dimethyl-4,21,37-trioxo-3,26,29,32-tetraoxa-22,36-diazatetracontan-40-oic acid. Formula Nr. 12-12

Molecular Weight: 672.9

Formula 12-12

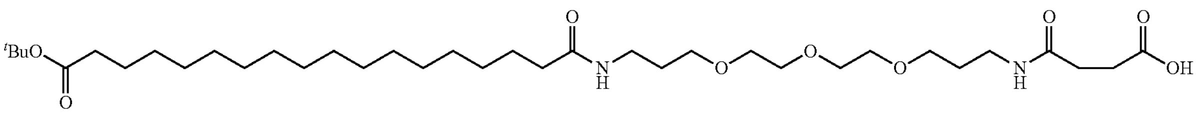

1.40 g (1 mmol) (2-chlorophenyl)(phenyl)(polystyryll) methyl 1-amino-15-oxo-4,7,10-trioxa-14-azaoctadecan-18-oate were coupled with 0.74 g (2 mmol) of 18-tert-butoxy-18-oxooctadecanoic acid. The protected modifier was then cleaved from the resin following the standard procedure. Yield: 0.63 g (93.62%).

Example 50: 32-(tert-butoxycarbonyl)-2,2-dimethyl-4,21,30-trioxo-3,25,28-trioxa-22,31-diazapentatriacontan-35-oic acid. Formula Nr. 2'-17

Molecular Weight: 700.9

Formula 2'-17

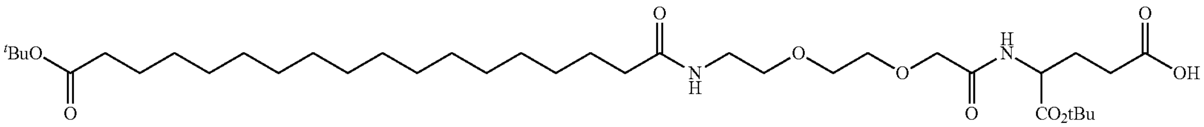

1.60 g (1 mmol) of H-Glu(OCTC-resin)-OtBu were coupled sequentially with 0.77 g (2 mmol) of 1-(9H-fluoren-9-yl)-3-oxo-2,7,10-trioxa-4-azadodecan-12-oic acid and with 0.74 g (2 mmol) of 18-tert-butoxy-18-oxooctadecanoic acid. The protected modifier was then cleaved from the resin following the standard procedure. Yield: 0.65 g (92.74%).

Example 51: 41-(tert-butoxycarbonyl)-2,2-dimethyl-4,21,30,39-tetraoxo-3,25,28,34,37-pentaoxa-22,31,40-triazatetratetracontan-44-oic acid. Formula Nr. 2'-18

Molecular Weight: 846.1

Formula 2'-18

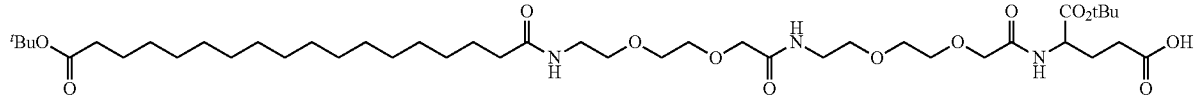

1.60 g (1 mmol) of H-Glu(OCTC-resin)-OtBu were coupled sequentially with 0.77 g (2 mmol) of 1-(9H-fluoren-9-yl)-3-oxo-2,7,10-trioxa-4-azadodecan-12-oic, with 0.77 g (2 mmol) of 1-(9H-fluoren-9-yl)-3-oxo-2,7,10-trioxa-4-azadodecan-12-oic acid and with 0.74 g (2 mmol) of 18-tert-butoxy-18-oxooctadecanoic acid. The protected modifier was then cleaved from the resin following the standard procedure. Yield: 0.82 g (96.92%).

Example 52: 43-(tert-butoxycarbonyl)-2,2-dimethyl-4,21,37,41-tetraoxo-3,26,29,32,39-pentaoxa-22,36,42-triazahexatetracontan-46-oic acid. Formula Nr. 2'-19

Molecular Weight: 874.2

Formula 2'-19

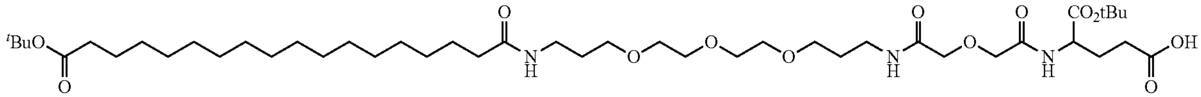

1.60 g (1 mmol) of H-Glu(OCTC-resin)-OtBu were coupled sequentially with 1.12 g (2 mmol) 1-(9H-fluoren-9-yl)-3,19-dioxo-2,8,11,14,21-pentaoxa-4,18-diazatricosan-23-oic acid and with 0.74 g (2 mmol) of 18-tert-butoxy-18-oxooctadecanoic acid. The protected modifier was then cleaved from the resin following the standard procedure. Yield: 0.79 g (90.37%).

Example 53: 42-(tert-butoxycarbonyl)-2,2-dimethyl-4,21,37,40-tetraoxo-3,26,29,32-tetraoxa-22,36,41-triazapentatetracontan-45-oic acid. Formula Nr. 2'-20

Molecular Weight: 858.2

Formula 2'-20

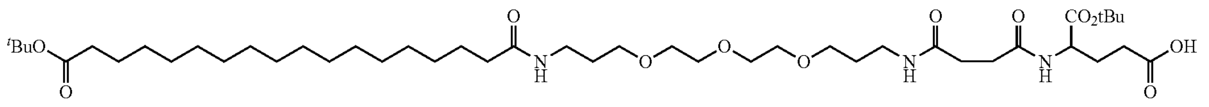

1.60 g (1 mmol) of H-Glu(OCTC-resin)-OtBu were coupled sequentially with 1.08 g (2 mmol) 1-(9H-fluoren-9-yl)-3,19-dioxo-2,8,11,14-tetraoxa-4,18-diazadocosan-22-oic acid and with 0.74 g (2 mmol) of 18-tert-butoxy-18-oxooctadecanoic acid. The protected modifier was then cleaved from the resin following the standard procedure. Yield: 0.82 g (92.05%).

Example 54:13-(tert-butoxycarbonyl)-34,34-dimethyl-10,15,32-trioxo-3,6,33-trioxa-9,14-diazapentatriacontan-1-oic acid. Formula Nr. 11-10

Molecular Weight: 700.9

Formula 11-10

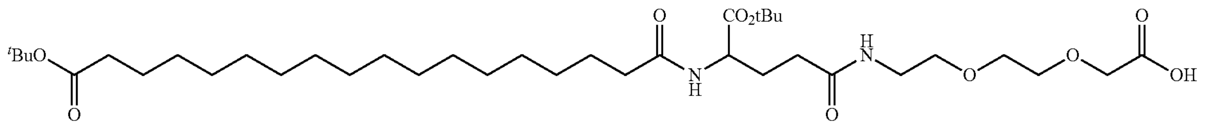

1.46 g (1 mmol) of (2-chlorophenyl)(phenyl)(polystyryl) methyl 2-(2-(2-aminoethoxy)ethoxy)acetate were coupled sequentially with 0.85 g (2 mmol) Fmoc-Glu-OtBu g and with 0.74 g (2 mmol) of 18-tert-butoxy-18-oxooctadecanoic acid. The protected modifier was then cleaved from the resin following the standard procedure. Yield: 0.64 g (91.31%).

Example 55: 22-(tert-butoxycarbonyl)-43,43-dimethyl-10,19,24,41-tetraoxo-3,6,12,15,42-pentaoxa-9,18,23-triazatetratetracontan-1-oic acid. Formula Nr. 11-11

Molecular Weight: 846.1

Formula 11-11

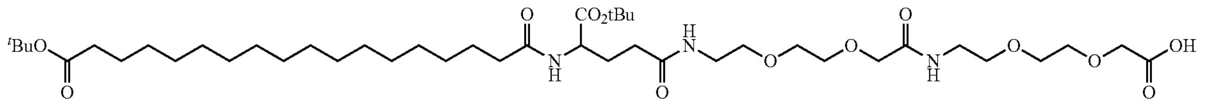

1.46 g (1 mmol) of (2-chlorophenyl)(phenyl)(polystyryl) methyl 2-(2-(2-aminoethoxy)ethoxy)acetate were coupled sequentially with 0.77 g (2 mmol) 1-(9H-fluoren-9-yl)-3-oxo-2,7,10-trioxa-4-azadodecan-12-oic acid, with 0.85 g (2 mmol) Fmoc-Glu-OtBu g and with 0.74 g (2 mmol) of 18-tert-butoxy-18-oxooctadecanoic acid. The protected modifier was then cleaved from the resin following the standard procedure. Yield: 0.82 g (96.92%).

Example 56: 24-(tert-butoxycarbonyl)-45,45-dimethyl-5,21,26,43-tetraoxo-3,10,13,16,44-pentaoxa-6,20,25-triazahexatetracontan-1-oic acid. Formula Nr. 12-13

Molecular Weight: 874.2

Formula 12-13

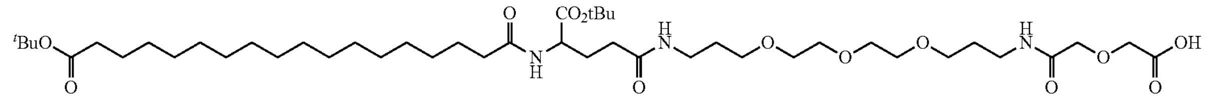

1, 45 g (1 mmol) of (2-chlorophenyl)(phenyl)(polystyryl) methyl 19-amino-5-oxo-3,10,13,16-tetraoxa-6-azanonadecan-1-oate were coupled sequentially with 0.85 g (2 mmol) Fmoc-Glu-OtBu g and with 0.74 g (2 mmol) of 18-tert-butoxy-18-oxooctadecanoic acid. The protected modifier was then cleaved from the resin following the standard procedure. Yield: 0.77 g (88.08%).

Example 57: 23-(tert-butoxycarbonyl)-2,2-dimethyl-4,21,26,39,41-pentaoxo-3,31,34,37-tetraoxa-22,27,40-triazatetratetracontan-44-oic acid. Formula Nr. 12-14

Molecular Weight: 858.1

Formula 12-14

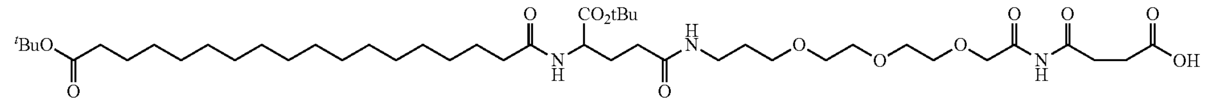

1.40 g (1 mmol) (2-chlorophenyl)(phenyl)(polystyryll) methyl 1-amino-15-oxo-4,7,10-trioxa-14-azaoctadecan-18-oate were coupled sequentially with 0.77 g (2 mmol) 1-(9H-fluoren-9-yl)-3-oxo-2,7,10-trioxa-4-azadodecan-12-oic acid, with 0.85 g Fmoc-Glu-OtBu and with 0.74 g (2 mmol) of 18-tert-butoxy-18-oxooctadecanoic acid. The protected modifier was then cleaved from the resin following the standard procedure. Yield: 0.76 g (88.57%).

Example 58: 5-tert-butoxy-4-(8-(8-tert-butoxy-8-oxooctylthio)octanamido)-5-oxopentanoic acid. Formula Nr. 2'-21

Molecular Weight: 559.8

Formula 2'-21

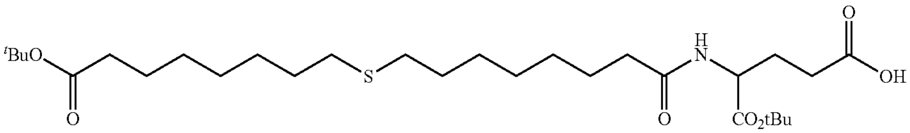

1.6 g (1 mmol) H-Glu(OCTC-resin)-OtBu were coupled with 0.75 g (2 mmol) of 8-(8-tert-butoxy-8-oxooctylthio) octanoic acid. The protected modifier was then cleaved from the resin following the standard procedure. Yield: 0.48 g (85.74%).

Example 59: 5,17-bis(tert-butoxycarbonyl)-1-(9H-fluoren-9-yl)-3,15-dioxo-2-oxa-7-thia-4,16-diaza-icosan-20-oic acid. Formula Nr. 2'-22

Molecular Weight: 726.9

Formula 2'-22

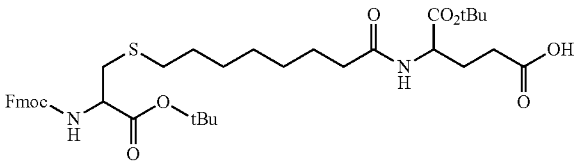

To suspension of 0.78 g (0.63 mmol) of H-Glu(2-chloro trityl-polystyryl ester)-OtBu in 10 ml of 25% piperidine in DMF was shacked for 30 min at RT in order to remove the Fmoc-group. The resin was then washed 8× with DMF. Then 6 ml DMF were added and to this mixture 0.54 g (1 mmol) Gmoc-Cys (octanoic acid)-OtBu (obtained by the reaction of Fmoc-Cys-OtBu and 8-bromooctanoic acid), 0.15 g DIC and 0.15 g HOBt were added and the mixture was stirred for 4 h at RT. The resin was then filtered and washed 4× with DMF and 6× with DCM. Then the resin was treated 6× with 1% TFA and the combined filtrates were extracted with water and concentrated in the RE with the gradual addition of hexanes. The precipitated product was filtered, washed with DEE and hexanes and dried in vacuum. Yield: 0.42 g (92%) of an amorphous solid.

Example 60: 16-(1-tert-butoxy-4-methyl-1-oxopentan-2-ylamino)-16-oxohexadecanoic acid. Formula Nr. 5'-1

Molecular Weight: 455.7

Formula 5'-1

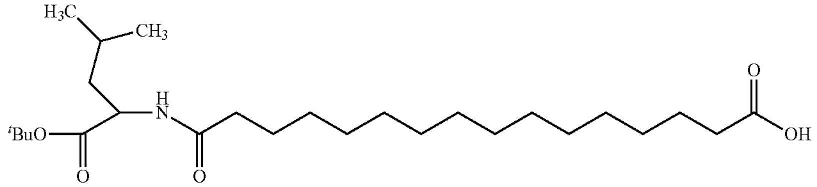

28.6 g tetradecanedioic acid in 400 ml DMF/DCM (1:3) were cooled to 0° C. Then 20.6 g DCC were added and the mixture was stirred for 2 h at 0° C. and 2 h at RT. Then 25.0 g L-leucine tert-butyl ester hydrochloride were added followed by 25 g DIPEA and 12.2 g DMAP. The mixture was stirred for 2 h at RT, concentrated in RE and then heated for 4 h at 65° C. To the obtained mixture brine and EtAc were added, followed by a standard acidic/basic extraction. The organic layer containing the product was concentrated in RE and the product was then purified by column chromatography using a mixture of chloroform/MeOH/AcOH (9/0,9/0.1) as the eluant. Fractions containing the product were concentrated in vacuum. Yield: 31.85 g of a colourless syrup were obtained and used in farther reactions as such.

Example 61: Synthesis of N-((carboxyalkylthio)alcanoic Acid) Amino Acid and Peptide Esters of the General Formula 26 Starting from Resin-Bound Mercapto Acids of Formula 25

The compounds of the general Formula 26 were obtained according to the scheme below starting from resin-bound mercapto acids.

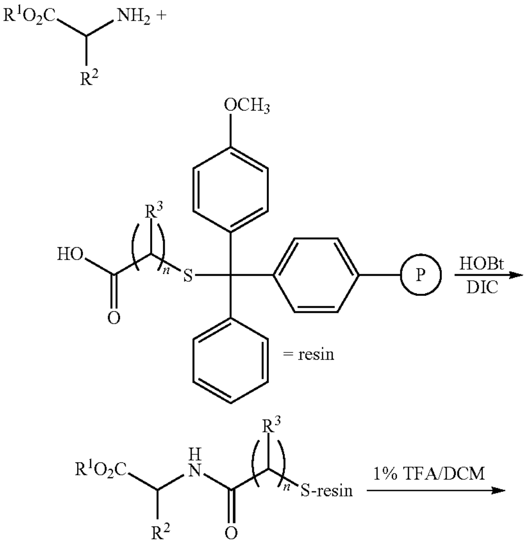

-continued

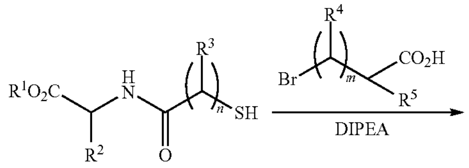

Formula 25

-continued

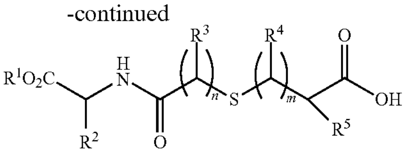

Formula 26

$R^1, R^2, R^3, R^4, R^5$ = H, alkyl or aralkyl; n, m = 0-16

N-Mercaptoacyl-amino acids or peptide esters of Formula 25 which were obtained according to (Spyros Mourtas, Dimitrios Gatos, Manolis Karavoltsos, Christina Katakalou and Kleomenis Barlos, Resin-bound mercapto acids: synthesis and application, Tetrahedron Letters 43 (2002) 3419-3421) were dissolved as 1 N-solutions in DMF and treated with a 1.2 molar excess of a bromoalcanoic acid for 1-4 h at RT. Then a 4 molar excess of cysteamine was added and the mixture was stirred for additional 1 h at RT. To the obtained mixture EtAc and brine were added and the obtained solution was acidified to pH=2.5-3 with 1N—HCl. After a standard extraction and concentration in the RE we obtained the N-((carboxyalkylthio)alcanoic acid) amino acids as oils or amorphous powders. The yields obtained were 80-95%.

Example 62: 6-(8-(1-tert-butoxy-3-methyl-1-oxobutan-2-ylamino)-8-oxooctylthio)hexanoic acid. Formula Nr. 26-1

Molecular Weight: 445.7

Formula 26-1

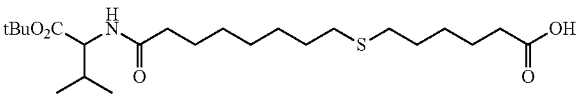

A suspension of 1.38 g (1.0 mmol) of 8-((4-methoxyphenyl)(phenyl)(p-polystyryl)methylthio)octanoic acid in 10 ml DMF were treated twice with 140 mg HOBt and 125 mg DIC. The obtained resin was washed 5× with 6 ml DMF and filtered. Then a solution of tert-butyl 2-amino-3-methylbutanoate [obtained by the alkaline extraction of 420 mg (2.0 mmol) of tert-butyl 2-amino-3-methylbutanoate hydrochloride] in 4 ml DMF was added and the mixture was shacked for 3 h at RT. The resin was filtered and washed 3×DMF and 6×DCM. The resin was then treated 6× with 5 ml of 1.5% TFA in DCM and the combined filtrates were extracted with water and brine and the DCM solution was concentrated in the RE. The obtained oil was dissolved in 5 ml DMF and to the obtained solution 260 mg DIPEA and 195 mg 6-bromohexanoic acid in 5 ml DMF were added at 5° C. The mixture was stirred for additional 1 h at 5° C. and 3 h at RT. Then 260 mg DIPEA and 254 mg 3-aminopropane-1 thiol hydrochloride (cysteamine hydrochloride) were added and the mixture was stirred for additional 2 h at RT. To the obtained DMF solution was then added EtAc and brine and the EtAc layer was extracted 3× with 5%-citric acid and water, the organic layer was dried over anhydrous Na2SO4 and concentrated in the RE. Yield: 0.37 g of a yellowish oil (83%).

Example 63: Synthesis of N-((carboxyalkylthio)alcanoic acid) Amino Acid and Peptide Esters of the General Formula 26 Starting from Resin-Bound Halogeno Acids The compounds of the general Formula 26 were obtained according to the scheme below starting from resin-bound halogeno acids (CBL-Patras, Merck).

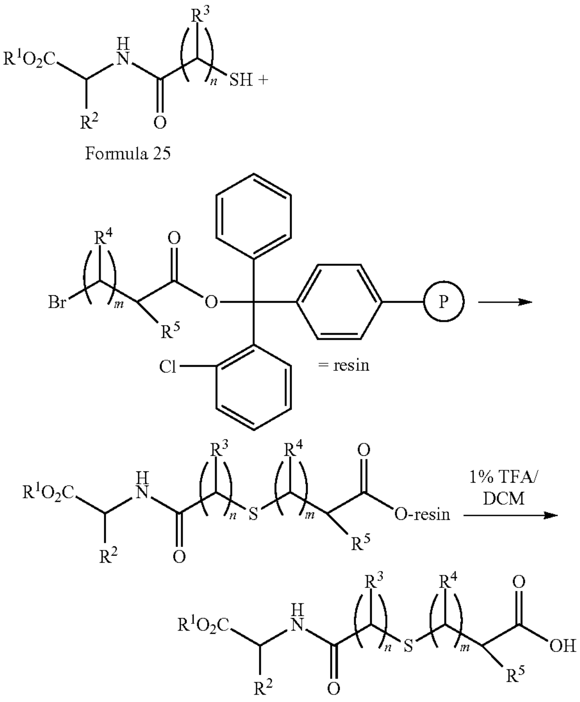

Formula 25

Formula 26

$R^1, R^2, R^3, R^4, R^5$ = H, alkyl or aralkyl; n, m = 0-16

Example 64: 6-(8-(1-tert-butoxy-3-methyl-1-oxobutan-2-ylamino)-8-oxooctylthio)hexanoic acid. Formula Nr. 26-1

Molecular Weight: 445.7

Formula 26-1

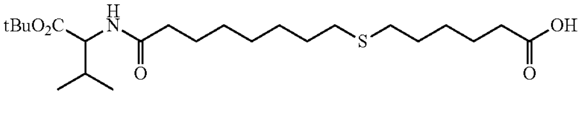

To a suspension of 74.0 g (50.0 mmol) 6-bromohexanoic acid 2-chlorotrityl ester (obtained according to the general esterification procedure) in 40 ml DMF were treated with 15 g of tert-butyl 2-(8-mercaptooctanamido)-3-methylbutanoate (obtained as described in the above example) and 26 g DIPEA and the mixture was shaked for 3 h at RT. The resin was then treated according to the standard procedure to give the protected modifier after precipitation with the addition of DEE as an amorphous powder with a melting range of 82-97° C. Yield 19.0 g (91.3%).

Example 65: Synthesis of Oligoethylene Glycol Derivatives of the General Formula 27

The compounds of the general Formula 27 were obtained according to the scheme below starting from resin-bound oligoethylene glycol derivatives of the Formula 11-1 (CBL-Patras) and acids of the general Formula 26 obtained as described above in the Example 63. The coupling and the cleavage of 27 from the resin were performed according to the standard procedures. Yield 80-95%.

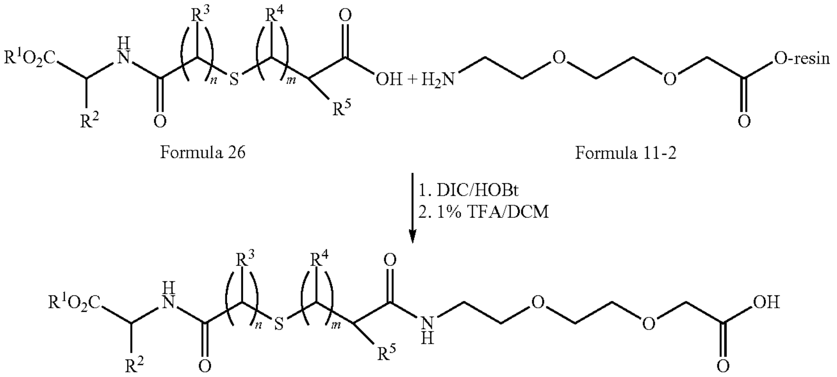

Formula 26

Formula 11-2

Formula 27

$R^1$, $R^2$, $R^3$, $R^4$, $R^5$ = H, alkyl or aralkyl; n, m = 0-16

Example 66: 26-isopropyl-29,29-dimethyl-10,24,27-trioxo-3,6,28-trioxa-16-thia-9,25-diazatriacontan-1-oic acid. Formula Nr. 11-12

Molecular Weight: 590.8

Formula 11-12

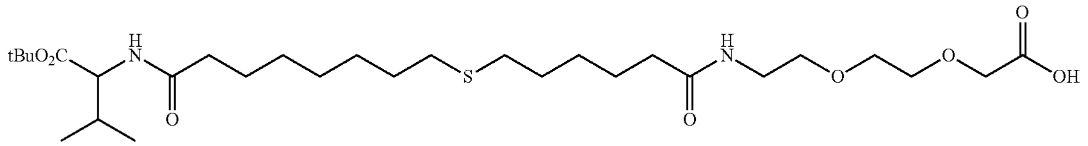

1.45 g (1 mmol) (2-chlorophenyl)(phenyl)(polystyryl) methyl 2-(2-(2-aminoethoxy)ethoxy)acetate were coupled with 0.89 g (2 mmol) of 6-(8-(1-tert-butoxy-3-methyl-1-oxobutan-2-ylamino)-8-oxooctylthio)hexanoic acid obtained as described above. The protected modifier was then cleaved from the resin following the standard procedure. Yield: 0.53 g (89.7%).

Example 67: Alternative General Scheme for the Synthesis of Oligoethylene Glycol Derivatives of the General Formula 27

1.45 g (1 mmol) (2-chlorophenyl)(phenyl)(polystyryl) methyl 2-(2-(2-aminoethoxy)ethoxy)acetate were coupled with 2 mmol of a haloalcanoic acid following the standard coupling procedures. The obtained resin-bound pegylated haloalcanoic acid of Formula 28 was then reacted with a 1.5 molar excess of the thiols of Formula 27. The obtained ester was then cleaved from the resin to yield 85-95% of the products with Formula 27

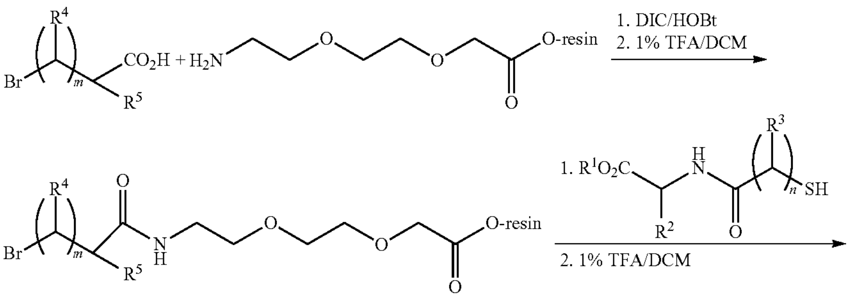

Formula 28

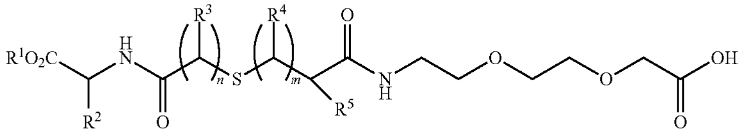

Formula 27

$R^1$, $R^2$, $R^3$, $R^4$, $R^5$ = H, alkyl or aralkyl; n, m=0-16

Example 68: 26-isopropyl-29,29-dimethyl-10,24,27-trioxo-3,6,28-trioxa-16-thia-9,25-diazatriacontan-1-oic acid. Formula Nr. 11-12

Molecular Weight: 590.8

Formula 11-12

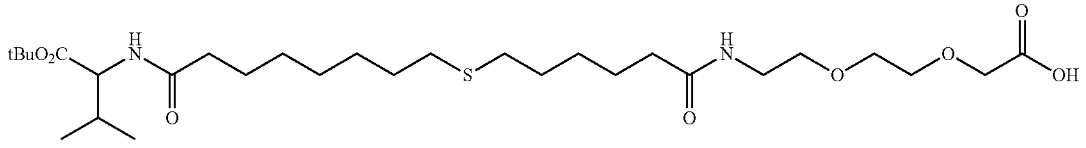

1.45 g (1 mmol) (2-chlorophenyl)(phenyl)(polystyryl) methyl 2-(2-(2-aminoethoxy)ethoxy)acetate were coupled sequentially with 0.39 (2 mmol) of 6-bromohexanoic acid and then treated with 0.66 g (2 mmol) tert-butyl 2-(8-mercaptooctanamido)-3-methylbutanoate. The protected modifier was then cleaved from the resin following the standard procedure. Yield: 0.55 g (93.1%).

Example 69: Synthesis of Oligoethylene Glycol Derivatives of the General Formula 29

1.67 g (1 mmol) 2-chlorophenyl)(phenyl)(polystyryl) methyl 1-(9H-fluoren-9-yl)-3,19-dioxo-2,8,11,14,21-pentaoxa-4,18-diazatricosan-23-oate were coupled with 2 mmol of a haloalcanoic acid following the standard coupling procedures. The obtained resin-bound pegylated haloalcanoic acid was then reacted with a 1.5 molar excess of the thiols of Formula 26. The obtained ester was then cleaved from the resin to yield 85-95% of the products with Formula 29

Formula 29

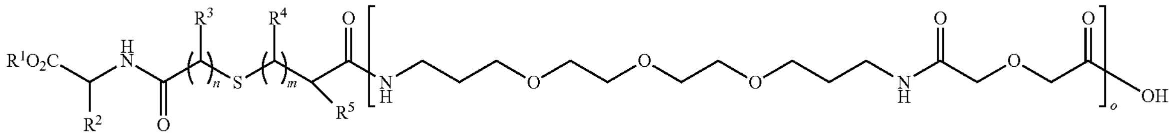

$R^1$, $R^2$, $R^3$, $R^4$, $R^5$ = H, alkyl or aralkyl; n, m, o = 0-16

Example 70: 37-isopropyl-40,40-dimethyl-5,21,35,38-tetraoxo-3,10,13,16,39-pentaoxa-27-thia-6,20,36-triazahentetracontan-1-oic acid. Formula Nr. 12-15

Molecular Weight: 764.0

Formula 12-15

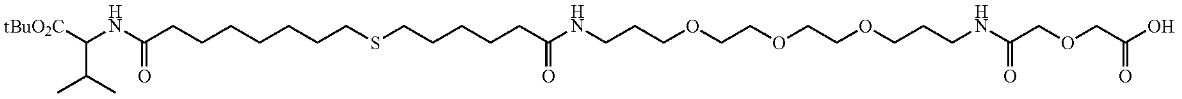

1.67 g (1 mmol (2-chlorophenyl)(phenyl)(polystyryl) methyl 1-(9H-fluoren-9-yl)-3,19-dioxo-2,8,11,14,21-pentaoxa-4,18-diazatricosan-23-oate were coupled with 0.89 g (2 mmol) of 6-(8-(1-tert-butoxy-3-methyl-1-oxobutan-2-ylamino)-8-oxooctylthio)hexanoic acid obtained as described above. The protected modifier was then cleaved from the resin following the standard procedure. Yield: 0.71 g (92.9%).

Example 71: Synthesis of Oligoethylene Glycol Derivatives of the General Formula 30

1.40 g (1 mmol) (2-chlorophenyl)(phenyl)(polystyryll) methyl 1-amino-15-oxo-4,7,10-trioxa-14-azaoctadecan-18-oate were coupled with 2 mmol of a haloalcanoic acid following the standard coupling procedures. The obtained resin-bound pegylated haloalcanoic acid was then reacted with a 1.5 molar excess of the thiols of Formula 25 obtained as described in the Example 61. The obtained esters were then cleaved from the resin to yield 80-97% of the products with Formula 30

Formula 30

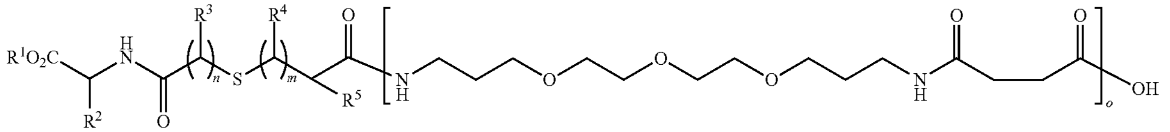

$R^1, R^2, R^3, R^4, R^5$ = H, alkyl or aralkyl; n, m, o = 0-16

Example 72: 5-isopropyl-2,2-dimethyl-4,7,21,37-tetraoxo-3,26,29,32-tetraoxa-15-thia-6,22,36-triaza-tetracontan-40-oic acid. Formula Nr. 12-16

Molecular Weight: 748.0

Formula 12-16

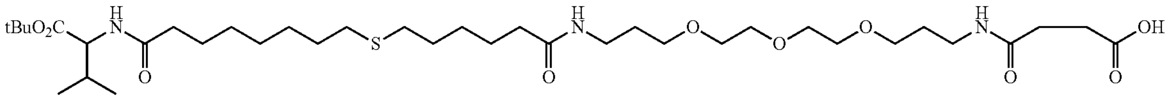

1.40 g (1 mmol) (2-chlorophenyl)(phenyl)(polystyryll) methyl 1-amino-15-oxo-4,7,10-trioxa-14-azaoctadecan-18-oate were coupled with 0.89 g (2 mmol) of 6-(8-(1-tert-butoxy-3-methyl-1-oxobutan-2-ylamino)-8-oxooctylthio) hexanoic acid obtained as described above. The protected modifier was then cleaved from the resin following the standard procedure. Yield: 0.70 g (93.6%).

Example 73: Synthesis of the Amino Acid Thioalcanoic Acid Pegylated Derivatives of the General Formula 31

1.60 g (1 mmol) H-Glu(OCTC-resin)-OtBu was coupled sequentially with 0.77 g (2 mmol) of 1-(9H-fluoren-9-yl)-3-oxo-2,7,10-trioxa-4-azadodecan-12-oic acid (2.0 mmol) and with 2 mmol of Ithioalcnoic acid obtained as described above in the Example 63. The protected modifier was then cleaved from the resin following the standard procedure. Yield: 85-95%.

Formula 31

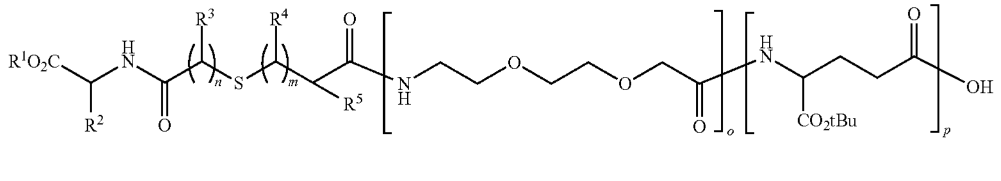

$R^1, R^2, R^3, R^4, R^5$ = H, alkyl or aralkyl; n, m = 0-16; o, p = 0-12

Example 74: 32-(tert-butoxycarbonyl)-5-isopropyl-2,2-dimethyl-4,7,21,30-tetraoxo-3,25,28-trioxa-15-thia-6,22,31-triazapentatriacontan-35-oic acid. Formula Nr. 2'-23

Molecular Weight: 776.0

Formula 2'-23

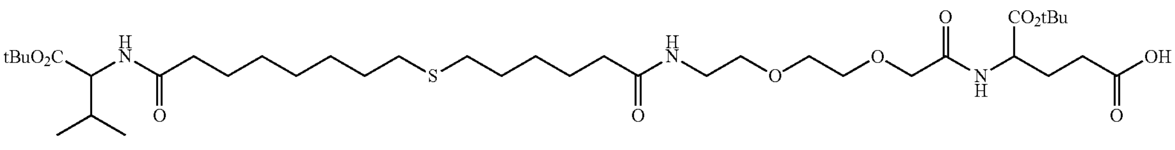

1.60 g (1 mmol) H-Glu(OCTC-resin)-OtBu was coupled sequentially with 0.77 g (2 mmol) of 1-(9H-fluoren-9-yl)-3-oxo-2,7,10-trioxa-4-azadodecan-12-oic acid (2.0 mmol) and with 0.89 g (2 mmol) of 6-(8-(1-tert-butoxy-3-methyl-1-oxobutan-2-ylamino)-8-oxooctylthio)hexanoic acid obtained as described above in the Example 64. The protected modifier was then cleaved from the resin following the standard procedure. Yield: 0.74 g (95.4%).

Example 75: Synthesis of the Amino Acid Thioalcanoic Acid Pegylated Derivatives of the General Formula 32

1.60 g (1 mmol) H-Glu(OCTC-resin)-OtBu was coupled sequentially with 1.12 g (2 mmol) of 1-(9H-fluoren-9-yl)-3,19-dioxo-2,8,11,14,21-pentaoxa-4,18-diazatricosan-23-oic acid and with 1.5 mmol) of the thioalcanoic acid of the Formula 26 obtained as described above in the Example 63. The protected modifier was then cleaved from the resin following the standard procedure. Yield: 85-97%.

Formula 32

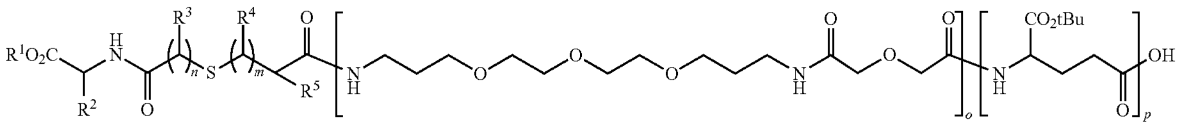

$R^1, R^2, R^3, R^4, R^5$ = H, alkyl or aralkyl; n, m = 0-16; o, p = 0-12

Example 76: 42-(tert-butoxycarbonyl)-5-isopropyl-2,2-dimethyl-4,7,21,37,41-pentaoxo-3,26,29,32,39-pentaoxa-15-thia-6,22,36-triazapentatetracontan-45-oic acid. Formula Nr. 2'-24

Molecular Weight: 934.2

Formula 2'-24

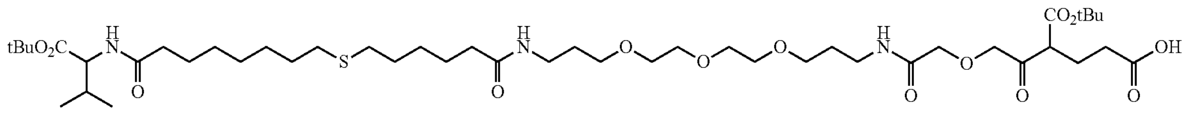

1.60 g (1 mmol) H-Glu(OCTC-resin)-OtBu was coupled sequentially with 1.12 g (2 mmol) of 1-(9H-fluoren-9-yl)-3,19-dioxo-2,8,11,14,21-pentaoxa-4,18-diazatricosan-23-oic acid and with 0.89 g (2 mmol) of 6-(8-(1-tert-butoxy-3-methyl-1-oxobutan-2-ylamino)-8-oxooctylthio)hexanoic acid obtained as described above in the Example 64. The protected modifier was then cleaved from the resin following the standard procedure. Yield: 0.88 g (94.2%).

Example 77: Synthesis of the Amino Acid Thioalcanoic Acid Pegylated Derivatives of the General Formula 33

1.60 g (1 mmol) H-Glu(OCTC-resin)-OtBu was coupled sequentially with 1.08 g (2 mmol) of 1-(9H-fluoren-9-yl)-3,19-dioxo-2,8,11,14-tetraoxa-4,18-diazadocosan-22-oic acid and with 0.89 g (2 mmol) of 6-(8-(1-tert-butoxy-3-methyl-1-oxobutan-2-ylamino)-8-oxooctylthio)hexanoic acid obtained as described above in the Example 64. The protected modifier was then cleaved from the resin following the standard procedure. Yield: 0.88 g (94.2%).

Formula 33

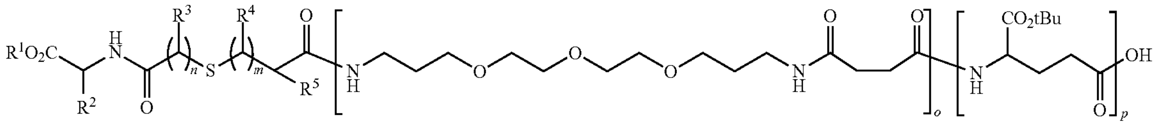

$R^1, R^2, R^3, R^4, R^5$ = H, alkyl or aralkyl; n, m = 0-16; o, p = 0-12

Example 78: 41-(tert-butoxycarbonyl)-5-isopropyl-2,2-dimethyl-4,7,21,37,40-pentaoxo-3,26,29,32-tetraoxa-15-thia-6,22,36-triazatetratetracontan-44-oic acid. Formula Nr. 2'-25

Molecular Weight: 918.2

Formula 2'-25

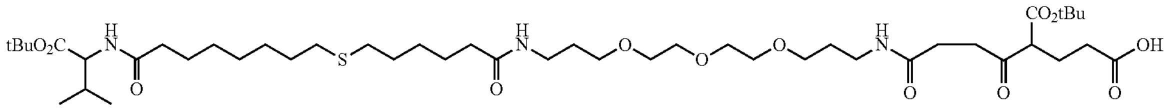

1.60 g (1 mmol) H-Glu(OCTC-resin)-OtBu was coupled sequentially with 1.08 g (2 mmol) of 1-(9H-fluoren-9-yl)-3,19-dioxo-2,8,11,14-tetraoxa-4,18-diazadocosan-22-oic acid and with 0.89 g (2 mmol) of 6-(8-(1-tert-butoxy-3-methyl-1-oxobutan-2-ylamino)-8-oxooctylthio)hexanoic acid obtained as described above in the Example 64. The protected modifier was then cleaved from the resin following the standard procedure. Yield: 0.83 g (90.4%).

Example 79: Synthesis of the Amino Acid Thioalcanoic Acid Pegylated Derivatives of the General Formula 34

1.45 g (1 mmol) (2-chlorophenyl)(phenyl)(polystyryl) methyl 2-(2-(2-aminoethoxy)ethoxy)acetate were coupled sequentially with 0.85 g (2.0 mmol) Fmoc-Glu-OtBu and with 2 mmol of the thioalcanoic acid of Formula 26 obtained as described in the Example 63. The protected modifier was then cleaved from the resin following the standard procedure. Yield: 85-95%.

Formula 33

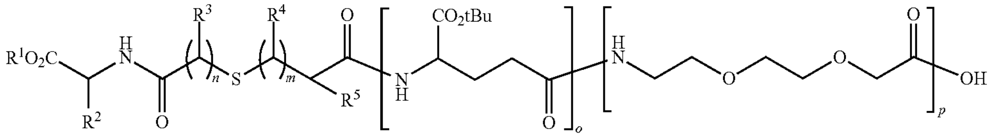

$R^1, R^2, R^3, R^4, R^5$ = H, alkyl or aralkyl; n, m = 0-16; o, p = 0-12

Example 80: 13-(tert-butoxycarbonyl)-31-isopropyl-34,34-dimethyl-10,15,29,32-tetraoxo-3,6,33-trioxa-21-thia-9,14,30-triazapentatriacontan-1-oic acid. Formula Nr. 11-13

Molecular Weight: 776.0

Formula 11-13

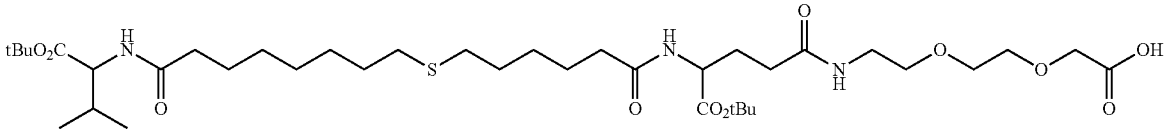

1.45 g (1 mmol) (2-chlorophenyl)(phenyl)(polystyryl) methyl 2-(2-(2-aminoethoxy)ethoxy)acetate were coupled sequentially with 0.85 g (2.0 mmol) Fmoc-Glu-OtBu and with 0.89 g (2 mmol) of 6-(8-(1-tert-butoxy-3-methyl-1-oxobutan-2-ylamino)-8-oxooctylthio)hexanoic acid obtained as described above in the Example 64. The protected modifier was then cleaved from the resin following the standard procedure. Yield: 0.71 g (91.5%).

Example 81: Synthesis of the Amino Acid Thioalcanoic Acid Pegylated Derivatives of the General Formula 35

1.67 g (1 mmol (2-chlorophenyl)(phenyl)(polystyryl) methyl 1-(9H-fluoren-9-yl)-3,19-dioxo-2,8,11,14,21-pentaoxa-4,18-diazatricosan-23-oate were coupled sequential with 0.85 g (2.0 mmol) Fmoc-Glu-OtBu and with thiohexanoic acid obtained as described above in the Example 63. The protected modifier was then cleaved from the resin following the standard procedure. Yield: 897%.

Formula 35

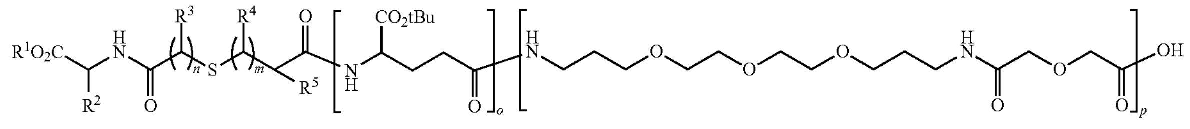

$R^1, R^2, R^3, R^4, R^5$ = H, alkyl or aralkyl; n, m = 0-16; o, p = 0-12

Example 82: 24-(tert-butoxycarbonyl)-42-isopropyl-45,45-dimethyl-5,21,26,40,43-pentaoxo-3,10,13,16,44-pentaoxa-32-thia-6,20,25,41-tetraazahexatetracontan-1-oic acid. Formula Nr. 12-17

Molecular Weight: 949.2

Formula 12-17

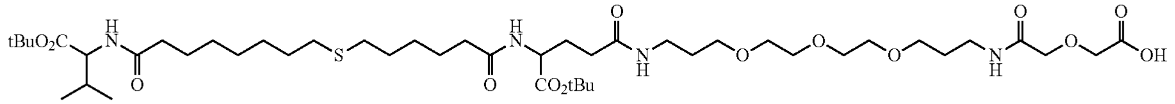

1.67 g (1 mmol (2-chlorophenyl)(phenyl)(polystyryl) methyl 1-(9H-fluoren-9-yl)-3,19-dioxo-2,8,11,14,21-pentaoxa-4,18-diazatricosan-23-oate were coupled sequential with 0.85 g (2.0 mmol) Fmoc-Glu-OtBu and with 0.89 g (2 mmol) of 6-(8-(1-tert-butoxy-3-methyl-1-oxobutan-2-ylamino)-8-oxooctylthio)hexanoic acid obtained as described above. The protected modifier was then cleaved from the resin following the standard procedure. Yield: 0.87 g (91.6%).

Example 83: Synthesis of the Amino Acid Thioalcanoic Acid Pegylated Derivatives of the General Formula 36

1.40 g (1 mmol) (2-chlorophenyl)(phenyl)(polystyryll) methyl 1-amino-15-oxo-4,7,10-trioxa-14-azaoctadecan-18-oate were coupled sequential with 0.85 g (2.0 mmol) Fmoc-Glu-OtBu and with 2 mmol) of thioalcanoic acid obtained as described above in Example 63. The protected modifier was then cleaved from the resin following the standard procedure. Yield: 80-95%

Formula 36

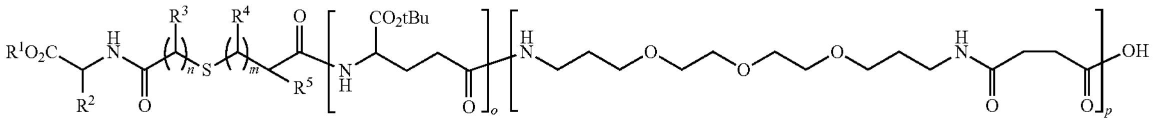

$R^1, R^2, R^3, R^4, R^5$ = H, alkyl or aralkyl; n, m = 0-16; o, p = 0-12

Example 84: 23-(tert-butoxycarbonyl)-5-isopropyl-2,2-dimethyl-4,7,21,26,42-pentaoxo-3,31,34,37-tetraoxa-15-thia-6,22,27,41-tetraazapentatetracontan-45-oic acid. Formula Nr. 12-18

Molecular Weight: 933.2

Formula 12-18

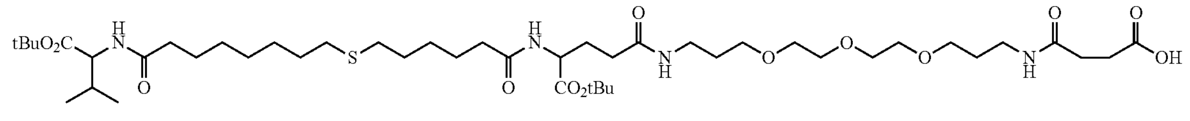

1.40 g (1 mmol) (2-chlorophenyl)(phenyl)(polystyryll) methyl 1-amino-15-oxo-4,7,10-trioxa-14-azaoctadecan-18-oate were coupled sequential with 0.85 g (2.0 mmol) Fmoc-Glu-OtBu and with 0.89 g (2 mmol) of 6-(8-(1-tert-butoxy-3-methyl-1-oxobutan-2-ylamino)-8-oxooctylthio)hexanoic acid obtained as described above. The protected modifier was then cleaved from the resin following the standard procedure. Yield: 0.81 g (86.8%).

Example 85: 32-(tert-butoxycarbonyl)-2,2-dimethyl-4,5,21,30-tetraoxo-3,25,28-trioxa-13-thia-22,31-diazapentatriacontan-35-oic acid. Formula Nr. 2'-26

Molecular Weight: 733.0

Formula 2'-26

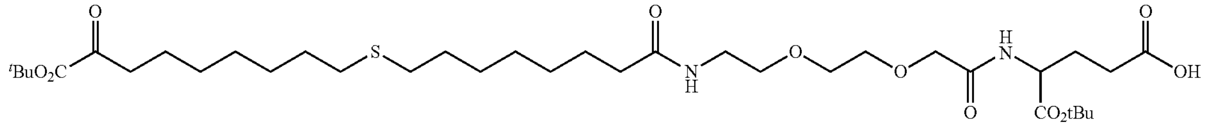

1.60 g (1 mmol) H-Glu(OCTC-resin)-OtBu was coupled sequentially with 0.77 g (2 mmol) of 1-(9H-fluoren-9-yl)-3-oxo-2,7,10-trioxa-4-azadodecan-12-oic acid and with 0.8 g (2 mmol) 8-(9-tert-butoxy-8,9-dioxononylthio)octanoic acid. The protected modifier was then cleaved from the resin following the standard procedure. Yield: 0.67 g (91.41%).

Example 86: 41-(tert-butoxycarbonyl)-2,2-dimethyl-4,5,21,30,39-pentaoxo-3,25,28,34,37-pentaoxa-13-thia-22,31,40-triazatetratetracontan-44-oic acid. Formula Nr. 2'-27

Molecular Weight: 878.1

Formula 2'-27

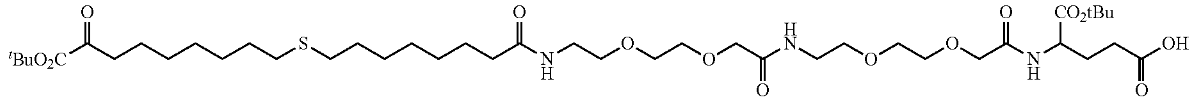

1.60 g (1 mmol) H-Glu(OCTC-resin)-OtBu was coupled sequentially with 0.77 g (2 mmol) of 1-(9H-fluoren-9-yl)-3-oxo-2,7,10-trioxa-4-azadodecan-12-oic acid, with 0.77 g (2 mmol) of 1-(9H-fluoren-9-yl)-3-oxo-2,7,10-trioxa-4-azadodecan-12-oic acid and with 0.8 g (2 mmol) 8-(9-tert-butoxy-8,9-dioxononylthio)octanoic acid. The protected modifier was then cleaved from the resin following the standard procedure. Yield: 0.80 g (91.11%).

Example 87: 43-(tert-butoxycarbonyl)-2,2-dimethyl-4,5,21,37,41-pentaoxo-3,26,29,32,39-pentaoxa-13-thia-22,36,42-triazahexatetracontan-46-oic acid. Formula Nr. 2'-28

Molecular Weight: 906.2

Formula 2'-28

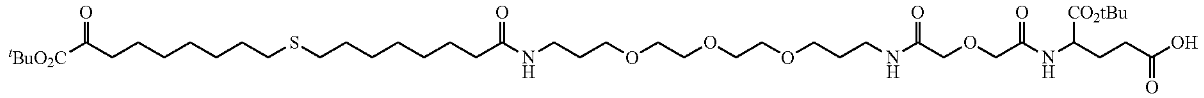

1.60 g (1 mmol) H-Glu(OCTC-resin)-OtBu was coupled sequentially with 1.12 g (2 mmol) of 1-(9H-fluoren-9-yl)-3,19-dioxo-2,8,11,14,21-pentaoxa-4,18-diazatricosan-23-oic acid and 0.8 g (2 mmol) 8-(9-tert-butoxy-8,9-dioxononylthio)octanoic acid. The protected modifier was then cleaved from the resin following the standard procedure. Yield: 0.81 g (91.01%).

Example 88: 42-(tert-butoxycarbonyl)-2,2-dimethyl-4,5,21,37,40-pentaoxo-3,26,29,32-tetraoxa-13-thia-22,36,41-triazapentatetracontan-45-oic acid. Formula Nr. Formula Nr. 2'-29

Molecular Weight: 890.2

Formula 2'-29

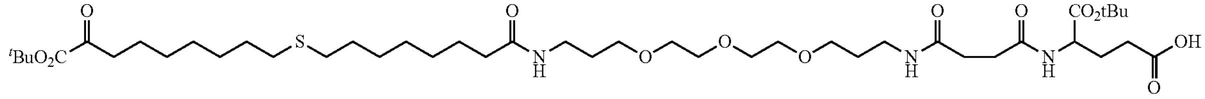

1.60 g (1 mmol) H-Glu(OCTC-resin)-OtBu was coupled sequentially with 1.08 g (2 mmol) of 1-(9H-fluoren-9-yl)-3,19-dioxo-2,8,11,14-tetraoxa-4,18-diazadocosan-22-oic acid and 0.8 g (2 mmol) 8-(9-tert-butoxy-8,9-dioxononylthio)octanoic acid. The protected modifier was then cleaved from the resin following the standard procedure. Yield: 0.81 g (91.01%).

Example 89: 13-(tert-butoxycarbonyl)-34,34-dimethyl-10,15,31,32-tetraoxo-3,6,33-trioxa-23-thia-9,14-diazapentatriacontan-1-oic acid. Formula Nr. 11-15

Molecular Weight: 733.0

Formula 11-15

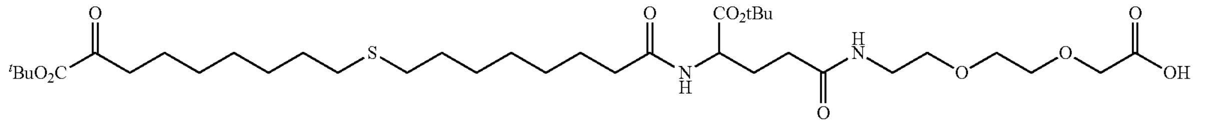

1.45 g (1 mmol) (2-chlorophenyl)(phenyl)(polystyryl) methyl 2-(2-(2-aminoethoxy)ethoxy)acetate were coupled sequentially with 0.85 g (2.0 mmol) Fmoc-Glu-OtBu and with 0.8 (2.00 mmol) g 8-(9-tert-butoxy-8,9-dioxononylthio)octanoic acid. The protected modifier was then cleaved from the resin following the standard procedure. Yield: 0.67 g (91.41%).

Example 90: 22-(tert-butoxycarbonyl)-43,43-dimethyl-10,19,24,40,41-pentaoxo-3,6,12,15,42-pentaoxa-32-thia-9,18,23-triazatetratetracontan-1-oic acid. Formula Nr. 11-16

Molecular Weight: 878.1

Formula 11-16

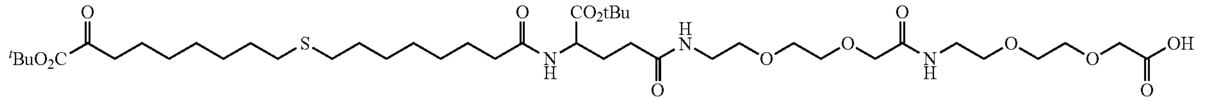

1.45 g (1 mmol) (2-chlorophenyl)(phenyl)(polystyryl) methyl 2-(2-(2-aminoethoxy)ethoxy)acetate were coupled sequentially with 0.77 g (2 mmol) of 1-(9H-fluoren-9-yl)-3-oxo-2,7,10-trioxa-4-azadodecan-12-oic acid, with 0.85 g (2.0 mmol) Fmoc-Glu-OtBu and with 0.8 (2.00 mmol) g 8-(9-tert-butoxy-8,9-dioxononylthio)octanoic acid. The protected modifier was then cleaved from the resin following the standard procedure. Yield: 0.81 g (97.94%).

Example 91: 24-(tert-butoxycarbonyl)-45,45-dimethyl-5,21,26,42,43-pentaoxo-3,10,13,16,44-pentaoxa-34-thia-6,20,25-triazahexatetracontan-1-oic acid. Formula Nr. 12-19

Molecular Weight: 906.2

Formula 12-19

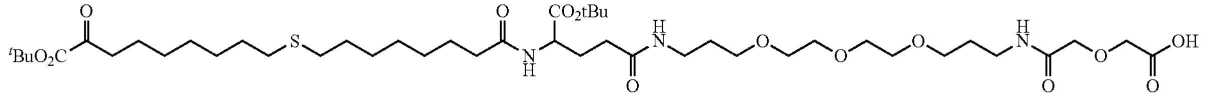

1.67 g (1 mmol (2-chlorophenyl)(phenyl)(polystyryl) methyl 1-(9H-fluoren-9-yl)-3,19-dioxo-2,8,11,14,21-pentaoxa-4,18-diazatricosan-23-oate were coupled sequential with 0.85 g (2.0 mmol) Fmoc-Glu-OtBu and with 0.8 (2.00 mmol) g 8-(9-tert-butoxy-8,9-dioxononylthio)octanoic acid. The protected modifier was then cleaved from the resin following the standard procedure. Yield: 0.86 g (94.9%).

Example 92: 23-(tert-butoxycarbonyl)-2,2-dimethyl-4,5,21,26,42-pentaoxo-3,31,34,37-tetraoxa-13-thia-22,27,41-triazapentatetracontan-45-oic acid. Formula Nr. 12-20

Molecular Weight: 890.2

Formula 12-20

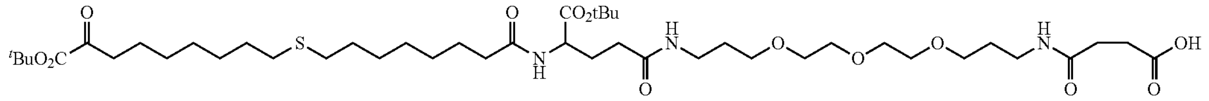

1.40 g (1 mmol) (2-chlorophenyl)(phenyl)(polystyryll) methyl 1-amino-15-oxo-4,7,10-trioxa-14-azaoctadecan-18-oate were coupled sequential with 0.85 g (2.0 mmol) Fmoc-Glu-OtBu and with 0.8 (2.00 mmol) g 8-(9-tert-butoxy-8,9-dioxononylthio)octanoic acid. The protected modifier was then cleaved from the resin following the standard procedure. Yield: 0.89 g (93.26%).

Example 93: 6,18-bis(tert-butoxycarbonyl)-2,2-dimethyl-4,16,21-trioxo-3,25,28-trioxa-8-thia-5,17,22-triazatriacontan-30-oic acid. Formula Nr. 11-17

Molecular Weight: 750.0

Formula 11-17

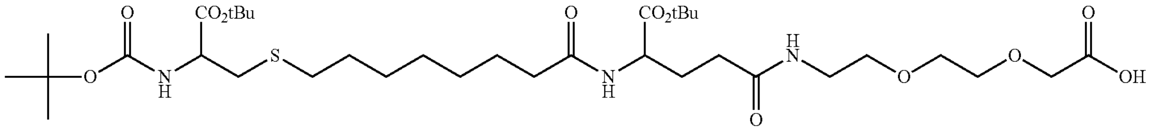

1.45 g (1 mmol) (2-chlorophenyl)(phenyl)(polystyryl) methyl 2-(2-(2-aminoethoxy)ethoxy)acetate were coupled sequentially with 0.85 g (2.0 mmol) Fmoc-Glu-OtBu and with 0.84 (2.00 mmol) g 8-(3-tert-butoxy-2-(tert-butoxycarbonylamino)-3-oxopropylthio)octanoic acid. The protected modifier was then cleaved from the resin following the standard procedure. Yield: 0.68 g (90.67%).

Example 94: 6,18-bis(tert-butoxycarbonyl)-2,2-dimethyl-4,16,21,30-tetraoxo-3,25,28,34,37-pentaoxa-8-thia-5,17,22,31-tetraazanonatriacontan-39-oic acid. Formula Nr. 11-18

Molecular Weight: 895.1

Formula 11-18

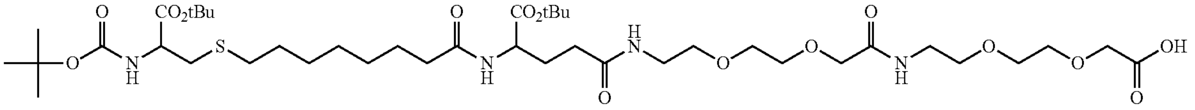

1.45 g (1 mmol) (2-chlorophenyl)(phenyl)(polystyryl) methyl 2-(2-(2-aminoethoxy)ethoxy)acetate were coupled sequentially with 0.77 g (2 mmol) of 1-(9H-fluoren-9-yl)-3-oxo-2,7,10-trioxa-4-azadodecan-12-oic acid, with 0.85 g (2.0 mmol) Fmoc-Glu-OtBu and with 0.84 (2.00 mmol) g 8-(3-tert-butoxy-2-(tert-butoxycarbonylamino)-3-oxopropylthio)octanoic acid. The protected modifier was then cleaved from the resin following the standard procedure. Yield: 0.84 g (93.84%).

Example 95: 6,18-bis(tert-butoxycarbonyl)-2,2-dimethyl-4,16,21,37-tetraoxo-3,26,29,32,39-pentaoxa-8-thia-5,17,22,36-tetraazahentetracontan-41-oic acid. Formula Nr. 12-21

Molecular Weight: 923.2

Formula 12-21

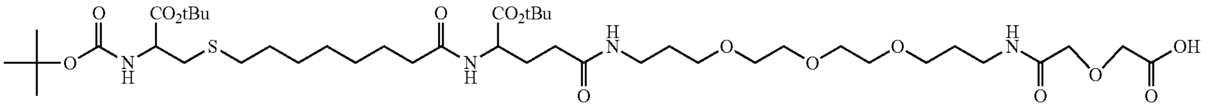

1.67 g (1 mmol (2-chlorophenyl)(phenyl)(polystyryl) methyl 1-(9H-fluoren-9-yl)-3,19-dioxo-2,8,11,14,21-pentaoxa-4,18-diazatricosan-23-oate were coupled sequentially with 0.85 g (2.0 mmol) Fmoc-Glu-OtBu and with 0.84 (2.00 mmol) g 8-(3-tert-butoxy-2-(tert-butoxycarbonylamino)-3-oxopropylthio)octanoic acid. The protected modifier was then cleaved from the resin following the standard procedure. Yield: 0.82 g (88.84%).

Example 96: 6,18-bis(tert-butoxycarbonyl)-2,2-dimethyl-4,16,21,37-tetraoxo-3,26,29,32-tetraoxa-8-thia-5,17,22,36-tetraazatetracontan-40-oic acid. Formula Nr. 12-22

Molecular Weight: 907.2

Formula 12-22

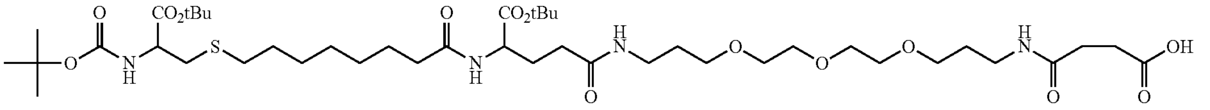

1.40 g (1 mmol) (2-chlorophenyl)(phenyl)(polystyryll) methyl 1-amino-15-oxo-4,7,10-trioxa-14-azaoctadecan-18-oate were coupled sequentially with 0.85 g (2.0 mmol) Fmoc-Glu-OtBu and with 0.84 (2.00 mmol) g 8-(3-tert-butoxy-2-(tert-butoxycarbonylamino)-3-oxopropylthio)octanoic acid. The protected modifier was then cleaved from the resin following the standard procedure. Yield: 0.87 g (95.92%).

Example 97: 6,27-bis(tert-butoxycarbonyl)-2,2-dimethyl-4,16,25-trioxo-3,20,23-trioxa-8-thia-5,17,26-triazatriacontan-30-oic acid. Formula Nr. 2'-30

Molecular Weight: 750.0

Formula 2'-30

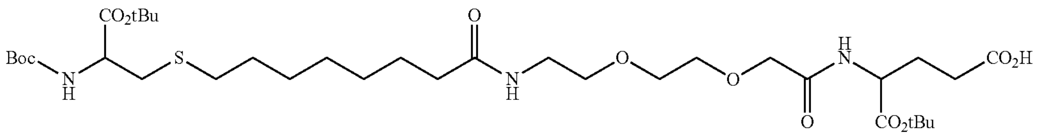

1.60 g (1 mmol) H-Glu(OCTC-resin)-OtBu was coupled sequentially with 0.77 g (2 mmol) of 1-(9H-fluoren-9-yl)-3-oxo-2,7,10-trioxa-4-azadodecan-12-oic acid and 0.84 (2.00 mmol) g 8-(3-tert-butoxy-2-(tert-butoxycarbonylamino)-3-oxopropylthio)octanoic acid. The protected modifier was then cleaved from the resin following the standard procedure. Yield: 0.65 g (86.67%).

Example 98: 6,36-bis(tert-butoxycarbonyl)-2,2-dimethyl-4,16,25,34-tetraoxo-3,20,23,29,32-pentaoxa-8-thia-5,17,26,35-tetraazanonatriacontan-39-oic acid. Formula Nr. 2'-31

Molecular Weight: 895.1

Formula 2'-31

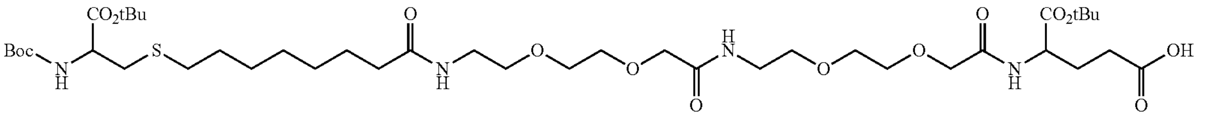

1.60 g (1 mmol) H-Glu(OCTC-resin)-OtBu was coupled sequentially with 0.77 g (2 mmol) of 1-(9H-fluoren-9-yl)-3-oxo-2,7,10-trioxa-4-azadodecan-12-oic acid, with 0.77 g (2 mmol) of 1-(9H-fluoren-9-yl)-3-oxo-2,7,10-trioxa-4-azadodecan-12-oic acid and 0.84 (2.00 mmol) g 8-(3-tert-butoxy-2-(tert-butoxycarbonylamino)-3-oxopropylthio)octanoic acid. The protected modifier was then cleaved from the resin following the standard procedure. Yield: 0.86 g (96.08%).

Example 99: 6,38-bis(tert-butoxycarbonyl)-2,2-dimethyl-4,16,32,36-tetraoxo-3,21,24,27,34-pentaoxa-8-thia-5,17,31,37-tetraazahentetracontan-41-oic acid. Formula Nr. 2'-32

Molecular Weight: 923.2

Formula 2'-32

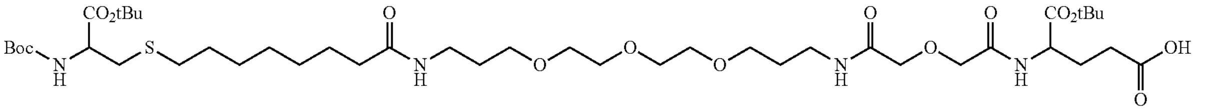

1.60 g (1 mmol) H-Glu(OCTC-resin)-OtBu was coupled sequentially with 1.12 g (2 mmol) of 1-(9H-fluoren-9-yl)-3,19-dioxo-2,8,11,14-tetraoxa-4,18-diazadocosan-22-oic acid and 0.84 g 8-(3-tert-butoxy-2-(tert-butoxycarbonylamino)-3-oxopropylthio)octanoic acid. The protected modifier was then cleaved from the resin following the standard procedure. Yield: 0.82 g (88.82%).

Example 100: 6,37-bis(tert-butoxycarbonyl)-2,2-dimethyl-4,16,32,35-tetraoxo-3,21,24,27-tetraoxa-8-thia-5,17,31,36-tetraazatetracontan-40-oic acid. Formula Nr. 2'-33

Molecular Weight: 907.2

Formula2'-33

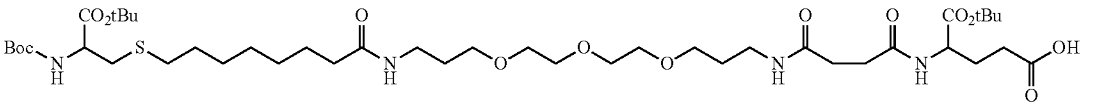

1.60 g (1 mmol) H-Glu(OCTC-resin)-OtBu was coupled sequentially with 1.08 g (2 mmol) of 1-(9H-fluoren-9-yl)-3,19-dioxo-2,8,11,14-tetraoxa-4,18-diazadocosan-22-oic acid and 0.84 g 8-(3-tert-butoxy-2-(tert-butoxycarbonylamino)-3-oxopropylthio)octanoic acid. The protected modifier was then cleaved from the resin following the standard procedure. Yield: 0.88 g (97.00%).

Example 101: 2-(((9H-fluoren-9-yl)methoxy)carbonylamino)-6-(5-tert-butoxy-5-oxo-4-palmitamidopentanamido)hexanoic acid, Formula 1-3

Molecular Weight: 792.1

Formula 1-3

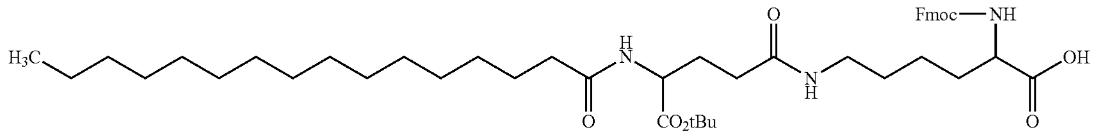

To 3.68 g Fmoc-Lys-OH (10.0 mmol, CBL-Patras) were reacted as described in Example 2 with 4.41 g (10.0 mmol) of 5-tert-butoxy-5-oxo-4-palmitamidopentanoic acid [Compound 2'-3 (Pal-Glu-OtBu), described in Example 12]. Precipitates with the addition of DEE. Yield: 6.12 g (77.3%).

Example 102: 2-(((9H-fluoren-9-yl)methoxy)carbonylamino)-6-(5-tert-butoxy-4-(16-tert-butoxy-16-oxohexadecanamido)-5-oxopentanamido)hexanoic acid. Formula 1-4

Molecular Weight: 878.1

Formula 1-4

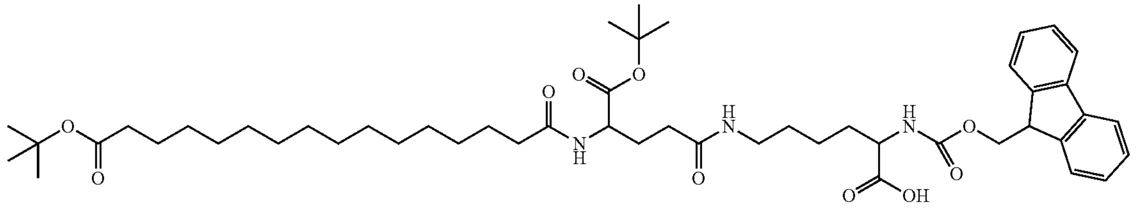

To 368 mg Fmoc-Lys-OH (1.0 mmol, CBL-Patras) were reacted as described in Example 2 with 527 mg (1.0 mmol) of 5-tert-butoxy-4-(16-tert-butoxy-16-oxohexadecanamido)-5-oxopentanoic acid [Compound 2'-16 described in Example 45].

Precipitates with the addition of DEE/Hex. Yield: 677 mg (77.1%).

Example 103: 28-(((9H-fluoren-9-yl)methoxy)carbonylamino)-1-(9H-fluoren-9-yl)-3,19,22-trioxo-2,8,11,14-tetraoxa-4,18,23-triazanonacosan-29-oic acid. Formula 1-5

Molecular Weight: 893.0

Formula 1-5

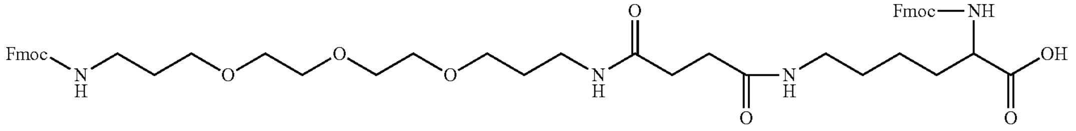

To 368 mg Fmoc-Lys-OH (1.0 mmol, CBL-Patras) were reacted as described in Example 2 with 542 mg (1.0 mmol) of 1-(9H-fluoren-9-yl)-3,19-dioxo-2,8,11,14-tetraoxa-4,18-diazadocosan-22-oic acid. Precipitates with the addition of Hex. Yield: 785 mg (87.9%).

Example 104: 32-(((9H-fluoren-9-yl)methoxy)carbonylamino)-5-(tert-butoxycarbonyl)-1-(9H-fluoren-9-yl)-3,8,17,26-tetraoxo-2,12,15,21,24-pentaoxa-4,9,18,27-tetraazatritriacontan-33-oic acid. Formula 1-6

Molecular Weight: 1066.2

Formula 1-6

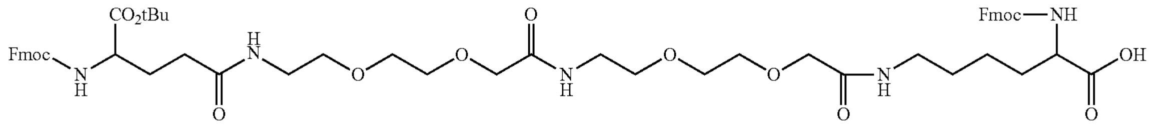

To 368 mg Fmoc-Lys-OH (1.0 mmol, CBL-Patras) were reacted as described in Example 2 with 715 mg (1.0 mmol) of 5-(tert-butoxycarbonyl)-1-(9H-fluoren-9-yl)-3,8,17-trioxo-2,12,15,21,24-pentaoxa-4,9,18-triazahexacosan-26-oic acid. Precipitates with the addition of DEE. Yield: 818 mg (76.7%).

Example 105: 2-(((9H-fluoren-9-yl)methoxy)carbonylamino)-6-(5-tert-butoxy-4-(8-(octylthio)octanamido)-5-oxopentanamido)hexanoic acid. Formula 1-7

Molecular Weight: 824.1

Formula 1-7

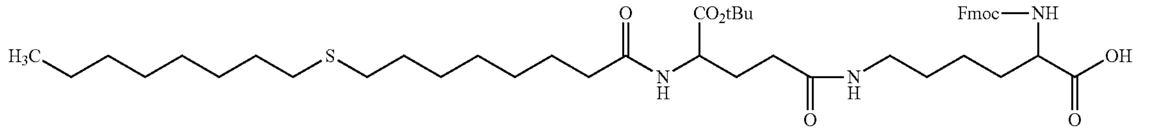

To 368 mg Fmoc-Lys-OH (1.0 mmol, CBL-Patras) were reacted as described in Example 2 with 474 mg (1.0 mmol) of 5-tert-butoxy-4-(8-(octylthio)octanamido)-5-oxopentanoic acid. Precipitates with the addition of DEE. Yield: 713 mg (86.5%).

Example 106: 32-(((9H-fluoren-9-yl)methoxy)carbonylamino)-23-(tert-butoxycarbonyl)-2,2-dimethyl-4,5,21,26-tetraoxo-3-oxa-13-thia-22,27-diazatritriacontan-33-oic acid. Formula 1-8

Molecular Weight: 938.2

Formula 1-8

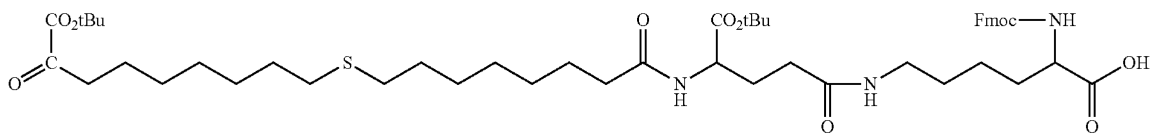

To 3.68 g Fmoc-Lys-OH (10.0 mmol, CBL-Patras) were reacted as described in Example 1 with 6.85 g (10 mmol) of 1-tert-butyl 5-(2,5-dioxopyrrolidin-1-yl) 2-(8-(9-tert-butoxy-8,9-dioxononylthio)octanamido)pentanedioate [succinimidylester of 2'-21 described in Example 58]. Precipitates with the addition of DEE. Yield: 8.42 g (89.8%).

Example 107: Solid-Phase Synthesis of Peptides and of their Protected Segments

General Procedure

A1. Preparation of Loaded 2-Chlorotrityl Resins, General Procedure

2-Chlorotrityl chloride resin (CTC-Cl) (100 g; loading 1.6 mmol/g) of CBL-Patras, was placed in a 2 L peptide synthesis reactor and swelled with 700 mL dichloromethane (DCM) for 30 min at 25° C. The resin was filtered and a solution of 100 mmol Fmoc-amino acid and 300 mmol diisopropylethylamine (DIEA) in 500 mL DCM was added. The mixture was stirred under nitrogen for 2 hours at 25° C. Then, the remaining active sites of 2-CTC resin were neutralised by adding 10 mL of methanol (MeOH) and reacting for 1 hour. The resin was filtered and washed twice with 400 mL DMF. The resin was filtered and treated twice with 500 mL 25% by volume of piperidine in DMF for 30 min. The resin was then washed four times with 500 mL DMF. The resin was unswelled with 3 washes with 500 mL of isopropanol (IPA). The resin was dried to constant weight. 70-95% of the mmol of the used amino acid was bound on the resin.

A2. Preparation of Loaded MBH-Resins, a General Method

MBH-Br resin (100 g; 190 mmol) was placed in a 2 L peptide synthesizer and swollen with 700 mL DCM for 30 min at 25° C. The resin was filtered and then a solution of Fmoc-amino acid and DIEA in 500 mL DCM was added. The mixture was stirred under nitrogen for 6 h at 25° C. Then the remaining active sites of the MBH resin were bound by adding 10 mL MeOH and stirring for 24 h. The resin was then filtered and washed twice with 400 mL DMF. The resin was filtered and reacted twice with 500 mL of a solution of 25% by volume of piperidine in DMF for 30 min. The resin was then washed four times with 500 mL DMF. The resin was diswelled with three washes with 500 mL IPA. The resin was then dried to constant weight under vacuum (15 torr, 25° C.). 60-90% of the mmol of the used amino acid were bound onto the resin.

B. Solid-Phase Synthesis, a General Protocol

The solid-phase synthesis was performed at 24° C., with 1.0 g amino acid esterified to the CTC or MBH resin as described in Part A of Example 1. During the whole synthesis the following protocol was used.

B1. Swelling of the Resin

The resin was placed in a 15 ml reactor and treated twice with 7 mL NMP, followed by filtration.

B2. Activation of the Amino Acid

The amino acid (3.0 equiv.) and 1-hydroxybenzotriazol (4.0 equiv.) was weighted and dissolved in a reactor with 2.5 their volume in NMP and cooled to 0° C. DIC was then added (3.0 equiv.) and the mixture was stirred for 15 min.

B3. Coupling

The solution which was prepared in B2 was then added to the B1 reactor. The reactor was washed once with one volume of DCM and was added to the reactor which was stirred for 1-3 h at 25°-30° C. In a sample the Kaiser Test was performed to determine the completion of the reaction. If the coupling reaction was not completed after 3 h (positive Kaiser Test), the reaction mixture was filtered and recoupled with a fresh solution of activated amino acid. After completion of the coupling the reaction mixture was filtered and washed 4 times with NMP (5 volumes per wash).

B4. Removal of the Fmoc-Group

The resulting resin in B3 was filtered and then treated for 30 min with 5 mL of a solution which contained 25% by volume of piperidine. The resin is then washed three times with 5 mL NMP.

B5. Elongation of the Peptide Chain

After the incorporation of each amino acid the steps B1-B5 were repeated until the completion of the peptide chain.

For the introduction of each individual amino acid the following Fmoc-amino acids were used: Fmoc-Gly-OH, Fmoc-Ala-OH, Fmoc-Val-OH, Fmoc-Ile-OH, Fmoc-Leu-OH, Fmoc-Met-OH, Fmoc-Phe-OH, Fmoc-Pro-OH, Fmoc-Asp(tBu)-OH, Fmoc-Glu(tBu)-OH, Fmoc-Lys(Boc)-OH, Fmoc-Lys(Mmt)-OH, Fmoc-Lys(Mtt)-OH, Fmoc-Ser(tBu)-OH, Fmoc-Ser(Trt)-OH, Fmoc-Thr(tBu)-OH, Fmoc-Thr(Trt)-OH, Fmoc-Tyr(tBu)-OH, Fmoc-Tyr(Clt)-OH, Fmoc-Asn-OH, Fmoc-Asn(Trt)-OH, Fmoc-Gln-OH, Fmoc-Gln(Trt)-OH, Fmoc-Arg(Pbf)-OH, Fmoc-His(Trt)-OH, Fmoc-Cys(Trt)-OH, Fmoc-Cys(Mmt)-OH and Fmoc-Cys(Acm)-OH and the following Boc-amino acids: Boc-Phe-OH, and Boc-Gly-OH.

C. General Method for the Cleavage from the CTC-Resin of the Partially Protected Peptides and of their Protected Segments which Contain Fmoc- or Boc-Groups on their N-Terminus and are Selectively Deprotected at an Individual Lysine, Ornithine or any Other Diamino Acid Side Chain or at the $N^{\alpha}$-Function of Glutamic Acid, Aspartic Acid or any Other Amino Diacid which is Bound on the Side Chain of a Diamino Acid Through its Side Chain Carboxyl Group The resin-bound peptide or peptide segment which was produced as described above in B1-B5 and was protected at a specific Lys, Orn, or any other diamino acid side chain with Mmt or Mtt or was substituted at a specific Lys, Orn, or any other diamino acid side chain with Trt-Glu-OR, Trt-Asp-OR or any other Trt-Aaa-OH was washed 4 times with 5 mL NMP, 3 times with 5 ml IPA and finally 5 times with 7 ml DCM to remove completely any residual NMP or other basic components. The resin was then cooled to 0° C., filtered from DCM and was treated six times with a solution of 10 mL 1.0-1.5% TFA in DCM/TES (95:5) at 5° C. The mixture was then stirred 20 min at 0° C. and filtered. The resin is then washed three times with 10 mL DCM. Pyridine is then added to the filtrates (1.3 equiv. relative to TFA) to neutralize the TFA. The cleavage solution in DCM was then mixed with an equal volume of water. The resulting mixture was distilled at reduced pressure to remove DCM (350 torr at 28° C.). The peptide or peptide segment precipitated after the removal of DCM. The resulting peptide was washed with water and ether and dried at 30-35° C. under 15 Torr vacuum. Alternatively DCM was removed in vacuum and the partially protected peptide was precipitate by the addition of ether.

Example 108

Synthesis of peptides selectively acylated at the Lysine side chain. General procedure. 1 mmol of a selectively at the Lys side chain deprotected peptide, was dissolved in 15 ml DMF. Then, 1.2 mmol DIPEA were added and 1 equivalent of an active ester of the modifier and the mixture was stirred for 1-12 h at RT. The reaction was then terminated by the addition of 1 mmol ethanolamine and stirring for additional 20 min at RT. The mixture was then poured into ice cold water and the resulting precipitate was washed with water and ether, deprotected as described under Example 107 and purified by HPLC.

Example 109: Peptide Deprotection—General Method

The partially protected peptide obtained as described above (0.01-0,005 mmol) was treated with 10 mL TFA/TES/thioanisol/water (85:5:5:5) or TFA/DTT/water (90:5:5 for 3 h at 5° C. and for 1 h at 15° C. The resulting solution was concentrated in vacuum and then the deprotected peptide was precipitated by the addition of DEE or diisopropylether and washed three times with 10 mL DEE or diisopropylether. The resulting solid was dried in vacuum (25° C., 1-10 Torr) until constant weight.

Example 110: Synthesis of Partially Protected $N^{\varepsilon B29}$—(H-Glu-OtBu) Des B30 Human Insulin B-Chain 1.0 g (0.45 mmol) of Fmoc-Lys(Trt-Glu-OtBu)-O-CTC-resin produced as described in Example 8 was applied and the synthesis and cleavage from the resin was performed as described in Example 107 according to general methods and the scheme below.

Fmoc-Lys(Trt-Glu-OtBu)-OH + CTC-chloride resin + DIPEA

Fmoc-Lys(Trt-Glu-OtBu)-O-CTC-resin

Solid-phase-synthesis (SEQ ID NO: 14)

Boc-Phe-Val-Asn(Trt)-Gln(Trt)-His(Trt)-Leu-Cys(Trt)-Gly-Ser(tBu)-His(Trt)-Leu-Val-Glu(tBu)-Ala-Leu-Tyr(tBu)-Leu-Val-Cys(Trt)-Gly-Glu(tBu)-Arg(Pbf)-Gly-Phe-Phe-Tyr(tBu)-Thr(tBu)-Pro-Lys(Trt-Glu-OtBu)-O-CTC-resin 1% TFA in DCM (SEQ ID NO: 15)

Boc-Phe-Val-Asn(Trt)-Gln(Trt)-His(Trt)-Leu-Cys(Trt)-Gly-Ser(tBu)-His(Trt)-Leu-Val-Glu(tBu)-Ala-Leu-Tyr(tBu)-Leu-Val-Cys(Trt)-Gly-Glu(tBu)-Arg(Pbf)-Gly-Phe-Phe-Tyr(tBu)-Thr(tBu)-Pro-Lys(Trt-Glu-OtBu)-OH

CTC = 2-chlorotrityl; DIPEA = diisopropylethylamine 1.0 g (0.24 mmol) of Fmoc-Lys(Trt-Glu-OtBu)-O-CTC-resin produced similarly to the Example 8 were applied and the synthesis and cleavage from the resin was performed as described in Example 107 according to general methods and the scheme above. Yield 1.24 g, 83.2%.

Example 111: Synthesis of GLP-1 (7-37) Modified at the Side Chain of $Lys^{26}$ with 2-(6-(8-(1-carboxy-2-methylpropylamino)-8-oxooctylthio)hexanamido) pentanedioic Acid (SEQ ID NOS 16-21 Disclosed Below, Respectively, in Order of Appearance)

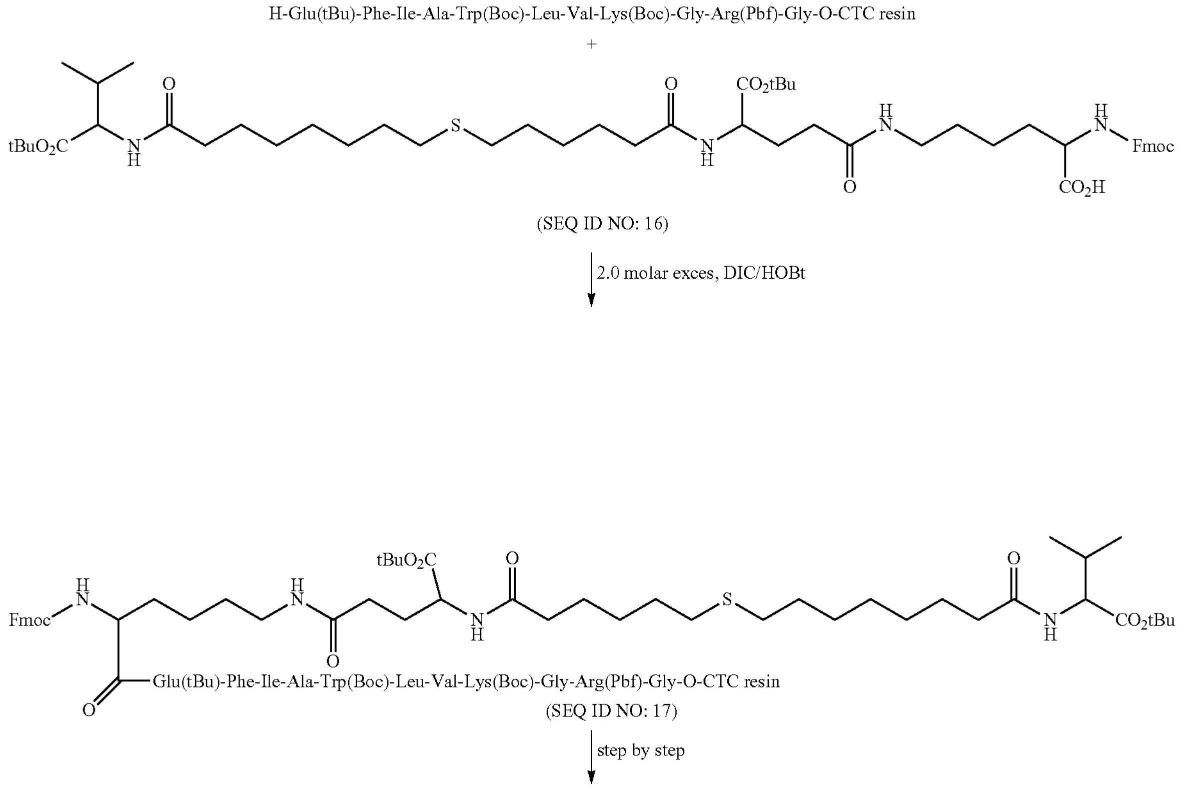

-continued

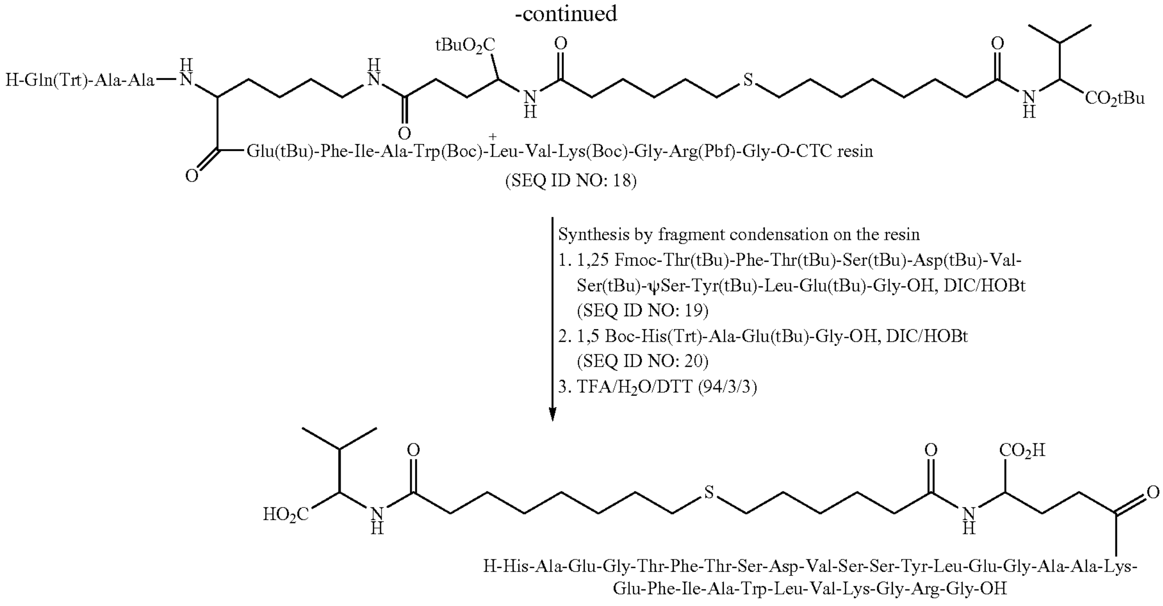

(SEQ ID NO: 21)

4.0 g of H-Gly-OCTC resin (1.0 mmol) were coupled sequentially with a two fold molar excess of DIC/HOBt and the amino acids Fmoc-Arg(Pbf)-OH, Fmoc-Gly-OH, Fmoc-Lys(Boc)-OH, Fmoc-Val-OH, Fmoc-Leu-OH, Fmoc-Trp (Boc)-OH, Fmoc-Ala-OH, Fmoc-Ile-OH, Fmoc-Phe-OH and Fmoc-Glu(tBu)-OH. After every coupling the Fmoc-group war removed by treatment with 15% piperidine in NMP. Then 1.96 g (2.0 mmol) of 32-(((9H-fluoren-9-yl) methoxy)carbonylamino)-23-(tert-butoxycarbonyl)-5-iso-propyl-2,2-dimethyl-4,7,21,26-tetraoxo-3-oxa-15-thia-6,22, 27-triazatritriacontan-33-oic acid in 20 ml DMF preactivated with equimolar amounts of DIC/HOBt in 20 ml NMP were added and the coupling was left to proceed for 24 h at RT. Then Fmoc-Ala-OH, Fmoc-Ala-OH and Fmoc-Gln (Trt)-OH were coupled sequentially using a five fold molar excess on amino acid, DIC and HOBt. After removal of the Fmoc-group the resin-bound peptide was coupled sequentially with 1.25 and 1.5 molar excess of 1. Fmoc-Thr(tBu)-Phe-Thr(tBu)-Ser(tBu)-Asp(tBu)-Val-Ser(tBu)-ψSer-Tyr (tBu)-Leu-Glu(tBu)-Gly-OH (SEQ ID NO: 22) and 2. Boc-His(Trt)-Ala-Glu(tBu)-Gly-OH (SEQ ID NO: 23), DIC/ HOBt. The resin was then treated with TFA/H2O/DTT (94/3/3) to cleave the peptide from the resin and deprotect it simultaneously. The crude peptide obtained was of 77% purity and was farther purified by RP-HPLC, lyophilized and dried. Yield 2.51 g (63%) with an HPLC-purity of 99.6%.

Example 112: Synthesis of Erythropoietin 1-28 Thioester Modified with 2-oxo-5-(17-oxooctade-canamido)hexanedioyl Ile-Ile (SEQ ID NOS 24-26 Disclosed Below, Respectively, in Order of Appearance)

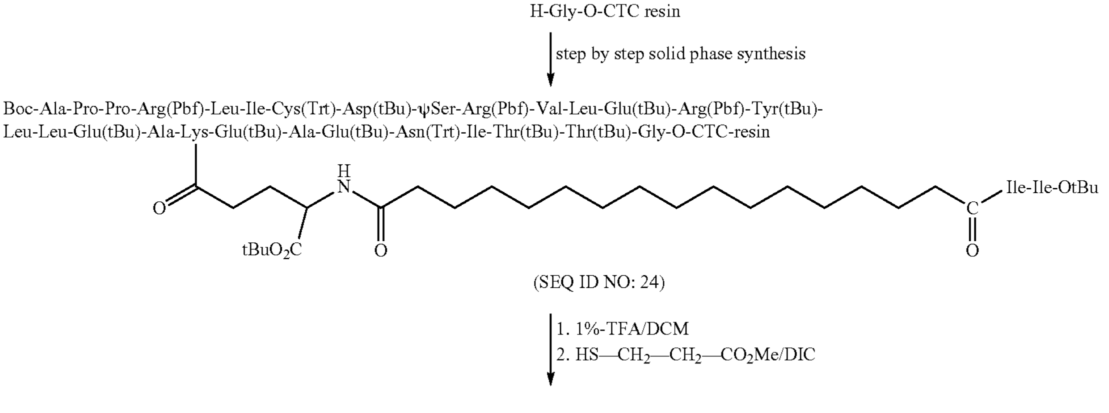

-continued

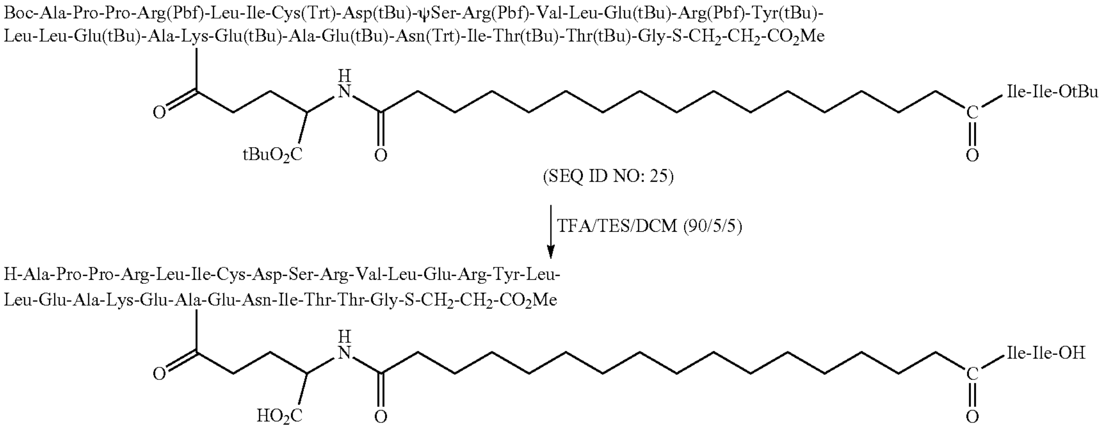

(SEQ ID NO: 26)

3 g (1.0 mmol) of Gly-O-CTC resin was coupled sequentially with Fmoc-amino acids and Boc-Ala-OH. The side chains of the applied amino acids were protected with Pbf (Arg), Trt (Cys, Asn), tBu (Asp, Glu, Tyr and Thr). The obtained resin-bound protected erythropoietin 1-27 was then removed from the resin by a 6×6 min treatments with 1% TFA in DCM. The combined filtrates were then extracted with water and concentrated to 25 ml. To this solution 1, 25 mmol of methyl 3-mercaptopropanoate and DIC were added and the mixture was stirred for 4 h at RT. The obtained mixture was concentrated in vacuum and the thioester was then perecipitated by the addition of DEE and washed 4× with DEE and dried in vacuum to constant weight. The crude protected thioester obtained was then deprotected by treatment with 50 ml of TFA/TES/DCM (90/5/5) for 4 h at RT. The deprotection solution was then concentrated in vacuum and the deprotected thioester was precipitated by the addition of DEE, washed with DEE and dried in vacuum. Yield: 3.13 g (96.4%) crude thioester of 82% purity determined by HPLC.

Example 113: Synthesis of Lys(Palm-Glu-OH)$^{26}$, Arg$^{34}$-GLP-1 (7-37) by Palmitoylation in Solution The synthesis was performed in the 1.0 mmol scale according to the general procedures.

The Lys$^{20}$ residue already modified with a Glu residue was introduced using 1.6 g (2.0 mmol) 14-(tert-butoxycarbonyl)-1-(9H-fluoren-9-yl)-3,11-dioxo-16,16,16-triphenyl-2-oxa-4,10,15-triazahexadecane-5-carboxylic acid according to the scheme below. Palmitic acid was activated with EDAC/HOSu. Yield: 1.51 g (44.9%).

H-Gly-O-CTC-resin

Solid-phase synthesis (SEQ ID NO: 27)
Boc-His(Trt)-Ala-Glu(tBu)-Gly-Thr(tBu)-Phe-Thr(tBu)-Ser(tBu)-Asp(tBu)-Val-Ser(tBu)-Ser(tBu)-Tyr(tBu)-Leu-Glu(tBu)-Gly-Gln-Ala-Ala-Lys(Trt-Glu-OtBu)-Glu(tBu)-Phe-Ile-Ala-Trp(Boc)-Leu-Val-Arg(Pbf)-Gly-Arg(Pbf)-Gly-O-CTC-resin 1% TFA in DCM (SEQ ID NO: 28)
Boc-His(Trt)-Ala-Glu(tBu)-Gly-Thr(tBu)-Phe-Thr(tBu)-Ser(tBu)-Asp(tBu)-Val-Ser(tBu)-Ser(tBu)-Tyr(tBu)-Leu-Glu(tBu)-Gly-Gln-Ala-Ala-Lys(Trt-Glu-OtBu)-Glu(tBu)-Phe-Ile-Ala-Trp(Boc)-Leu-Val-Arg(Pbf)-Gly-Arg(Pbf)-Gly-OH Palm-OSu (SEQ ID NO: 29)
Boc-His(Trt)-Ala-Glu(tBu)-Gly-Thr(tBu)-Phe-Thr(tBu)-Ser(tBu)-Asp(tBu)-Val-Ser(tBu)-Ser(tBu)-Tyr(tBu)-Leu-Glu(tBu)-Gly-Gln-Ala-Ala-Lys(Palm-Glu-OtBu)-Glu(tBu)-Phe-Ile-Ala-Trp(Boc)-Leu-Val-Arg(Pbf)-Gly-Arg(Pbf)-Gly-OH (SEQ ID NO: 30)
H-His-Ala-Glu-Gly-Thr-Phe-Thr-Ser-Asp-Val-Ser-Ser-Tyr-Leu-Glu-Gly-Gln-Ala-Ala-Lys(Palm-Glu-OH)-Glu-Phe-Ile-Ala-Trp-Leu-Val-Arg-Gly-Arg-Gly-OH

Example 114: Synthesis of Lys$^{20}$ modified partially protected erythropoietin 1-28. Modifier: 4-(tert-butoxycarbonyl)-6,15,24-trioxo-8,11,17,20-tetraoxa-32-thia-5,14,23-triaza-tetracontan-1-oic acid The synthesis performed as shown below was started with 1.00 g (0.25 mmol) of H-Gly-O-CTC-resin. The Lys residue was introduced with 2 equivalents Fmoc-Lys(Trt-Glu-OtBu)-OH. The partially protected peptide was modified in solution using 190 mg modifier activated with EDAC/HOSu. Yield 1.34 g (88.5%).

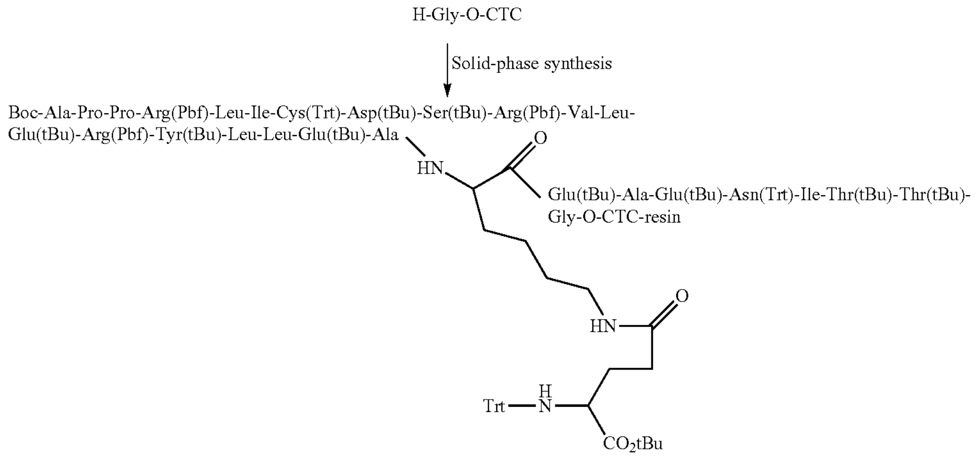
(SEQ ID NO: 31)
1% TFA
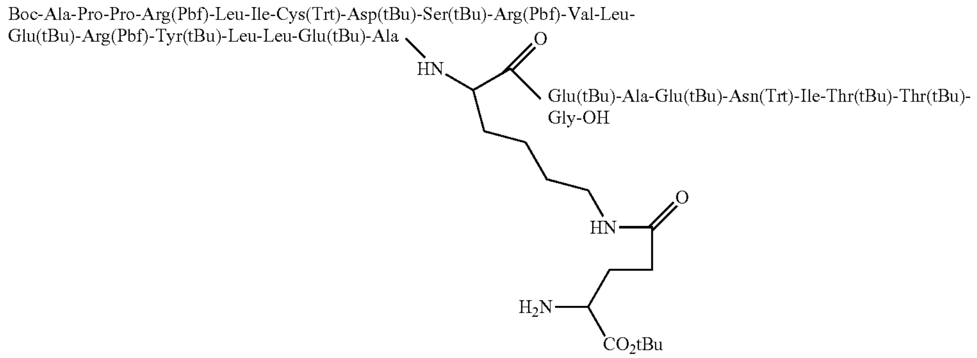
(SEQ ID NO: 32)
Lys-modification
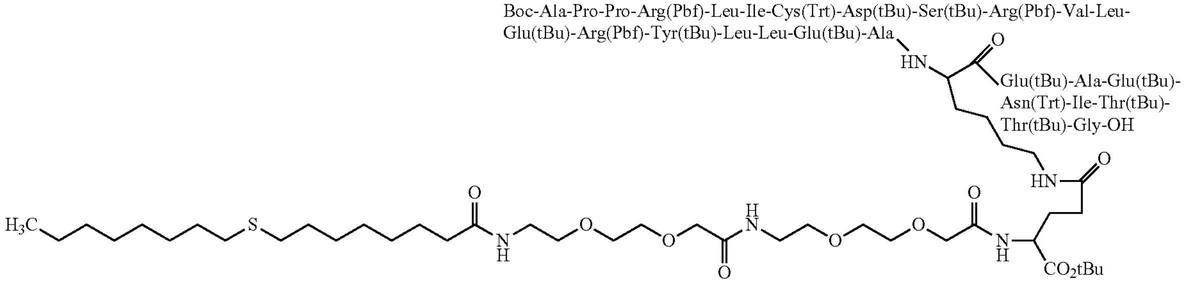
(SEQ ID NO: 33)

Example 115: Synthesis of Lys[154] Modified Erythropoietin 114-166. Modifier was Introduced Using: 2-(((9H-fluoren-9-yl)methoxy)carbonylamino)-6-(5-tert-butoxy-5-oxo-4-palmitamidopentanamido) hexanoic acid Molecular Weight: 792.1

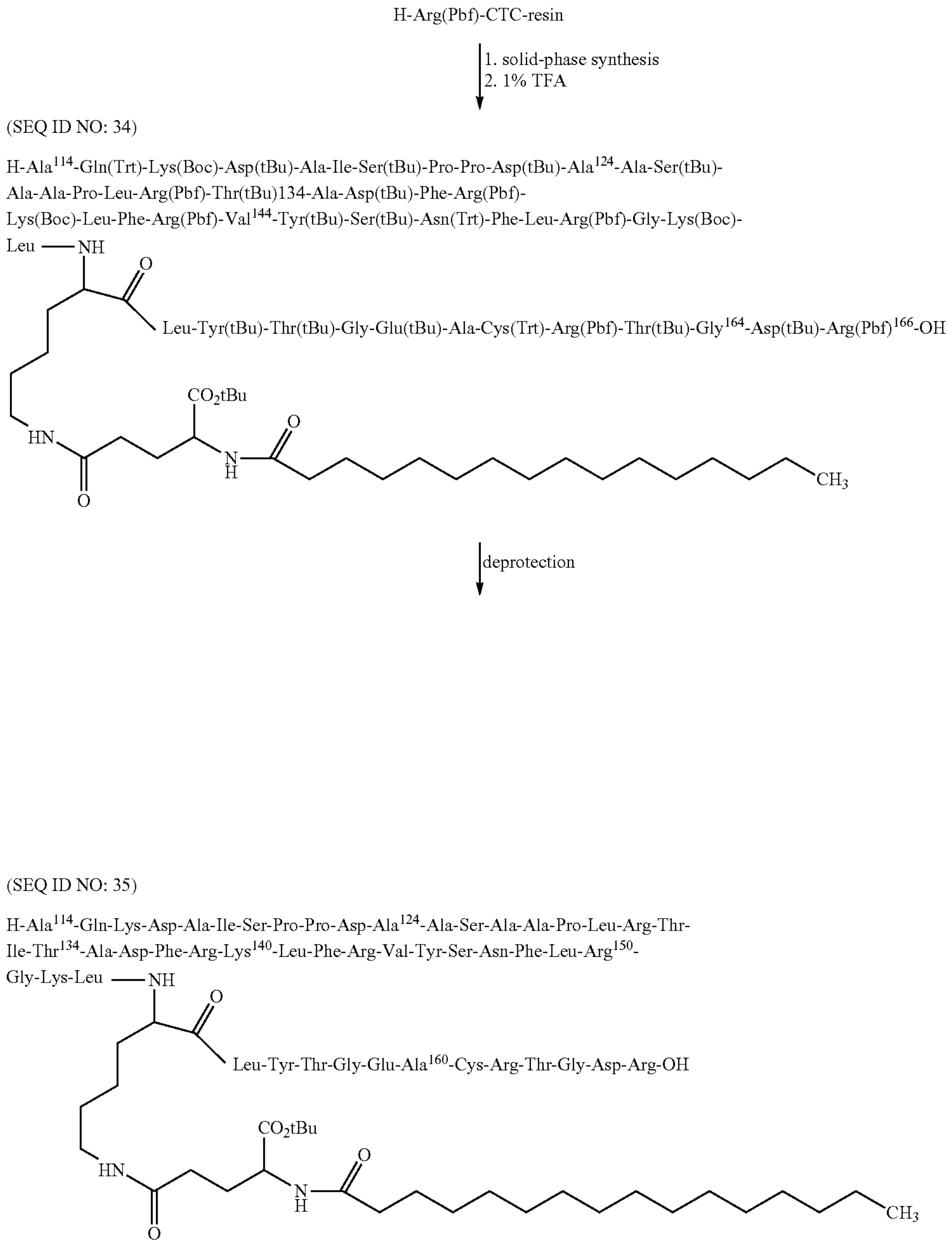

Example 116: Synthesis of ACTH Modified at Lys[21]

The synthesis was performed in the 1.00 mmol scale. The modifier was introduced with 2.6 g (2.0 mmol) tert-butyl 5-acetyl-34-(tert-butoxycarbonyl)-1-(9H-fluoren-9-yl)-52-isopropyl-3,11,15,31,36,50-hexaoxo-2,13,20,23,26-pentaoxa-42-thia-4,10,16,30,35,51-hexaazatripentacontan-53-oate. Yield: 1.65 g (33.3%).

(SEQ ID NO: 36)

H-Ser-Tyr-Ser-Met-Glu-His-Phe-Arg-Trp-Gly-Lys-Pro-Val-Gly-Lys-Lys-Arg-Arg-Pro-

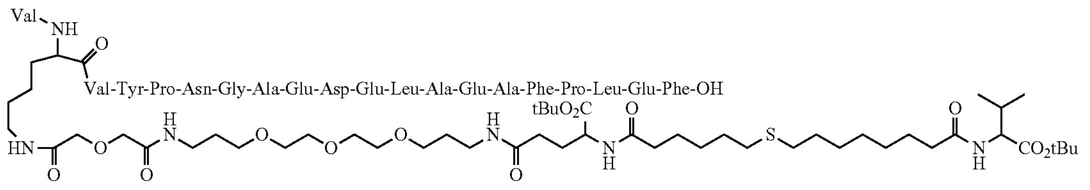

Example 117: Synthesis of Human PTH 1-34 Modified at Lys[13]

The synthesis was performed on the 1.0 mmol scale. The modifier was introduced using 2.4 g (2.0 mmol) 50-(((9H-fluoren-9-yl)methoxy)carbonylamino)-41-(tert-butoxycarbonyl)-2,2-dimethyl-4,21,30,39,44-pentaoxo-3,25,28,34,37-pentaoxa-22,31,40,45-tetraazahenpentacontan-51-oic acid. Yield: 1.06 g (22.3%).

(SEQ ID NO: 37)

H-Ser-Val-Ser-Glu-Ile-Gln-Leu-Met-His-Asn-Leu-

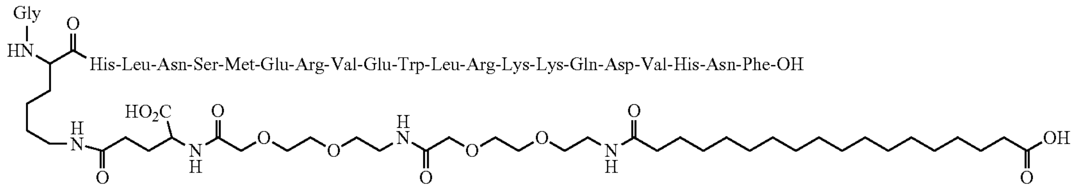

Example 118: Synthesis of Exenatide Acetate Modified at Lys[12]

The synthesis was performed in the 10 mmol scale on the Fmoc-Ser(CTC-resin)-$NH_2$. The modifier was introduced using 16.0 g (20.0 mmol) tert-butyl 5-acetyl-1-(9H-fluoren-9-yl)-28-isobutyl-3,11,26-trioxo-2-oxa-4,10,27-triazanonacosan-29-oate. The Leu[10]-Ser[11] residues were introduced with the corresponding pseudoproline. Yield: 29.7 g (31.4%).

(SEQ ID NO: 38)

His-Gly-Glu-Gly-Thr-Phe-Thr-Ser-Asp-Leu-

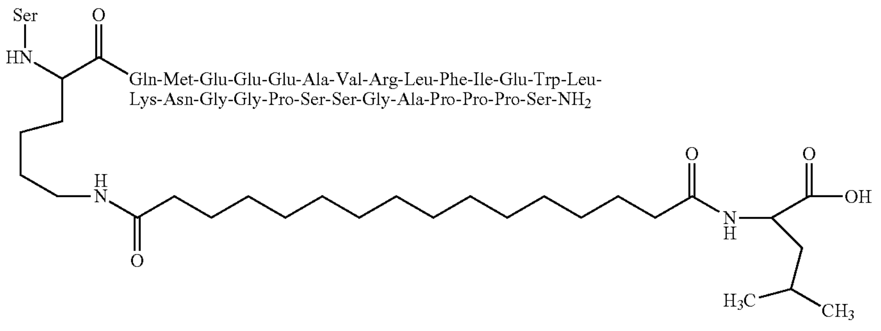

Example 119: Synthesis of MOG (35-55) Modified at Lys[21]

The synthesis was performed in the 1.0 mmol scale. The modifier was introduced using two equivalents of 51-(((9H-fluoren-9-yl)methoxy)carbonylamino)-42-carboxy-5-isopropyl-2,2-dimethyl-4,7,21,37,41,45-hexaoxo-3,26,29,32,39-pentaoxa-15-thia-6,22,36,46-tetraazadopentacontan-52-oic acid (2.46 g) activated with EDAC and pentafluorophenol. Yield 1.56 g (42%).

Exact Mass: 1075.67

Molecular Weight: 1076.43 m/z: 1075.67 (100.0%), 1076.67 (60.5%), 1077.68 (17.1%), 1077.67 (9.2%), 1078.68 (5.2%), 1078.67 (3.1%), 1076.68 (1.1%), 1079.68 (1.1%)

(SEQ ID NO: 39)

H-Met-Glu-Val-Gly-Trp-Tyr-Arg-Ser-Pro-Phe-Ser-Arg-Val-Val-His-Leu-Tyr-Arg-Asn-Gly-Lys-OH (SEQ ID NO: 39)

H-Met-Glu-Val-Gly-Trp-Tyr-Arg-Ser-Pro-Phe-Ser-Arg-Val-His-Leu-Tyr-Arg-Asn-

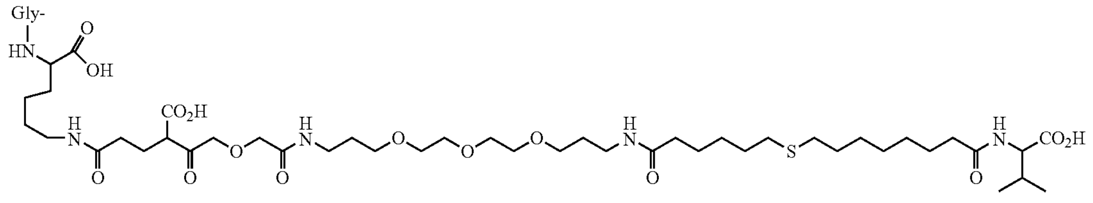

Example 120: Synthesis of Human CRF Modified at Lys[36]

(SEQ ID NO: 40)

H-Ser-Glu-Glu-Pro-Pro-Ile-Ser-Leu-Asp-Leu-Thr-Phe-His-Leu-Leu-Arg-Glu-Val-Glu-
Met-Ala-Arg-Ala-Glu-Gln-Leu-Ala-Gln-Gln-Ala-His-Ser-

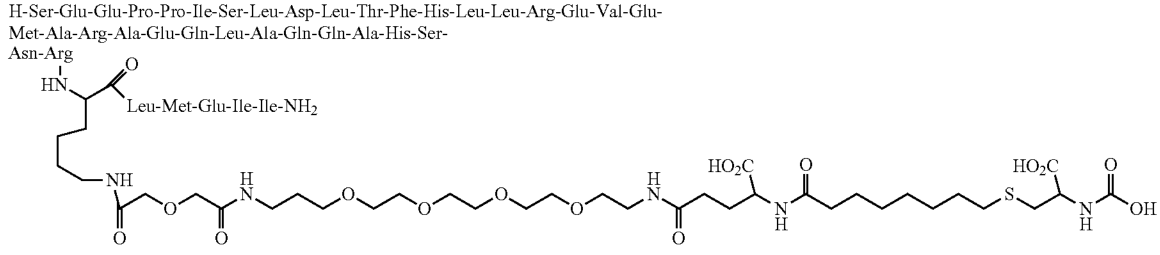

The synthesis was performed in a 1.0 mmol scale. The modifier was introduced using 23,35-di-tert-butyl 1-perfluorophenyl 39,39-dimethyl-4,20,25,37-tetraoxo-2,9,12,15,38-pentaoxa-33-thia-5,19,24,36-tetraazatetracontane-1,23,35-tricarboxylate produced in situ using pentafluorophenol and EDAC as the activating agents. Yield: 2.01 g (36.5%).

Example 121: Synthesis of PYY Modified at Lys[4]. Modifier Group: 1-amino-24-carboxy-1,5,21,26-tetraoxo-3,10,13,16-tetraoxa-6,20,25-triazatritetracontan-43-oyl (SEQ ID NO: 41)

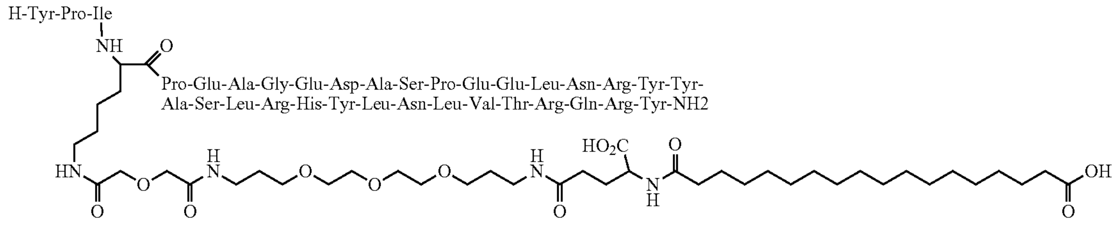

The synthesis was performed by the SPPS method as described in the general procedures in a 1.0 mmol scale using the Lys-derivative 52-(((9H-fluoren-9-yl)methoxy)carbonylamino)-23-(tert-butoxycarbonyl)-2,2-dimethyl-4,21,26,42,46-pentaoxo-3,31,34,37,44-pentaoxa-22,27,41,47-tetraazatripentacontan-53-oic acid for the introduction of Lys at position 4. Yield: 2.22 g (44%).

Example 122: Synthesis of Fuzeon Modified at Lys[18]

N-acetyl-Tyr-Thr-Ser-Leu-Ile-His-Ser-Leu-Ie-Glu-Glu-Ser-Gln-Asn-Gln-Gln-Glu-Lys(X)-Asn-Glu-Gln-Glu-Leu-Leu-Glu-Leu-Asp-Lys-Trp-Ala-Ser-Leu-Trp-Asn-Trp-Phe-$NH_2$ (SEQ ID NO: 42). the modified Lys at position 18 was introduced using 34-(tert-butoxycarbonyl)-1-(9H-fluoren-9-yl)-55,55-dimethyl-3,11,15,31,36,53-hexaoxo-2,13,20,23,26,54-hexaoxa-44-thia-4,10,16,30,35-pentaazahexapentacontane-5-carboxylic acid The synthesis was performed in 0.1 mmol scale by the condensation of three protected fragments in solution according to EP 1 071 442 89. The fragments used were as shown below:

Fragment 1: N-acetyl-Tyr(tBu)-Thr(tBu)-Ser(tBu)-Leu-Ile-His(Trt)-Ser(tBu)-Leu-Ie-Glu (tBu)-Glu(tBu)-Ser(tBu)-Gln(Trt)-Asn(Trt)-Gln(Trt)-Gln-OH (SEQ ID NO: 43)

Fragment 2: Fmoc-Glu(tBu)-Lys(X)-Asn(Trt)-Glu(tBu)-Gln(Trt)-Glu(tBu)-Leu-Leu-Glu(tBu)-Leu-OH (SEQ ID NO: 44); X=34-(tert-butoxycarbonyl)-1-(9H-fluoren-9-yl)-55,55-dimethyl-3,11,15,31,36,53-hexaoxo-2,13,20,23,26,54-hexaoxa-44-thia-4,10,16,30,35-pentaaza-hexapentacontane-5-carbonyl).

Fragment 3: Fmoc-Asp(tBu)-Lys(Boc)-Trp(Boc)-Ala-Ser(tBu)-Leu-Trp(Boc) Asn(Trt)-Trp (Boc)-Phe-$NH_2$ (SEQ ID NO: 45).

Yield 178.4 mg (32%).

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

The invention claimed is:

1. A process for preparing a peptide of Formula 22,

Formula 22

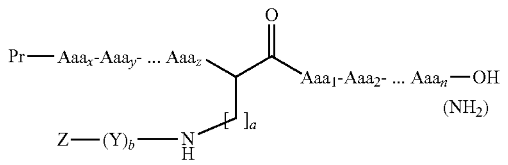

wherein:

$Aaa_xAaa_y \ldots Aaa_z$ and $Aaa_1Aaa_2 \ldots Aaa_n$ are each independently a natural or synthetic peptide comprising 1 to 100 natural or unnatural amino acid residues, each of which is optionally protected:

Pr is an amino protecting group:

a is an integer from 1 to 10;

b is an integer from 1 to 7;

each Y is independently a bivalent group selected from:

(a) a group of Formula 2'

Formula 2'

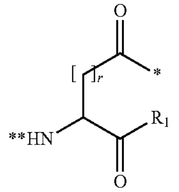

where* denotes the point of attachment;

** indicates a bond to a group Z as defined above or another group Y;

r is an integer from 1 to 12; and $R_1$ is $NH_2$ or $OR_3$, where $R_3$ is selected from H, alkyl, aryl and aralkyl; and (b) a group of Formula 11' or Formula 12', Formula 11'

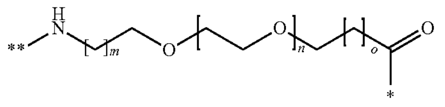

Formula 12'

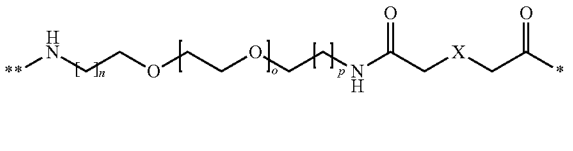

where* denotes the point of attachment;

** denotes a bond to a group Z as defined above or another group Y;

X is absent, or is selected from $CH_2$, O, S and NR, where R is H, alkyl or aralkyl; and m, n, and p are each independently an integer from 1 to 25; and is an integer from 0 to 25;

Z is a terminal group selected from:

(a) a group of Formula 6, 7, 8 or 37,

Formula 6

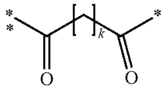

Formula 7

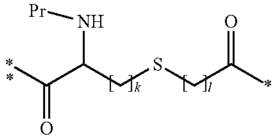

Formula 8

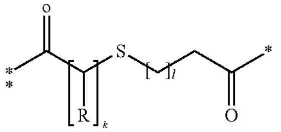

Formula 37

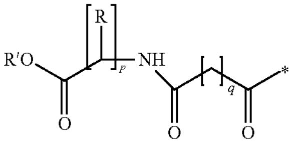

where * denotes the point of attachment to Y;

** indicates a bond to a group selected from OH, OR, and NRR' and Formula 9;

Formula 9

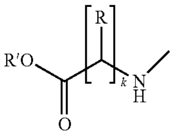

k and l are each independently an integer from 0 to 25;

p is an integer from 1 to 20;

q is an integer from 5 to 20; and

R and R' are each independently selected from H, alkyl and aralkyl; and (b) a group of Formula 5, Formula 5

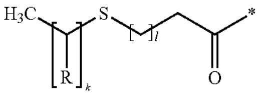

where* denotes the point of attachment to Y; and k and l are each independently an integer from 0 to 25;

said process comprising the steps of:

(i) reacting a compound of Formula 19 with a compound of Formula Z—$(Y)_b$—OH to form a compound of Formula 1:

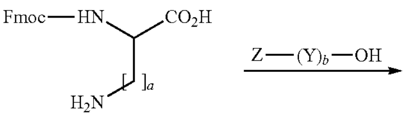

Formula 19

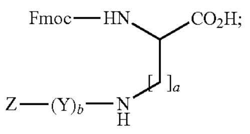

Formula 1

(ii) reacting a resin-bound peptide of formula H-$Aaa_1$-$Aaa_2$- . . . $Aaa_n$-Resin with a compound of Formula 1 to form a compound of Formula 20:

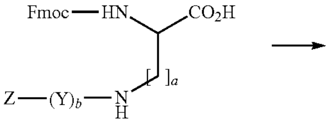

Formula 1

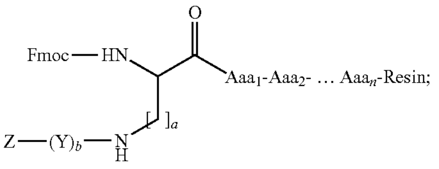

Formula 20

(iii) removing the protecting group from the compound of Formula 20 and coupling with an at least N-terminally protected amino acid or peptide having a free or activated carboxylic acid function and optionally repeating this step to give a compound of Formula 21, Formula 21

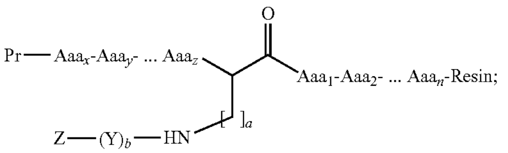

and (iv) removing said compound of Formula 21 from the resin to form a compound of Formula 22, Formula 22

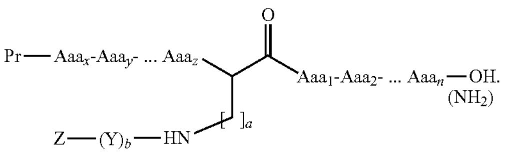

2. A process according to claim 1 wherein b is an integer from 1 to 3.

3. The process of claim 1, wherein Z is a group of Formula 6.

4. The process of claim 1, wherein Y is a group of Formula 2'.

5. The process of claim 1, wherein Y is a group of Formula 11'.

6. The process of claim 1, wherein $R_1$ is O-alkyl.

7. The process according to claim 1 wherein the compound of Formula Z—$(Y)_b$—OH is selected from the group consisting of:

Formula 11-11

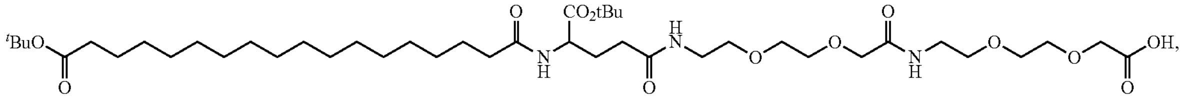

,

Formula 2'-16

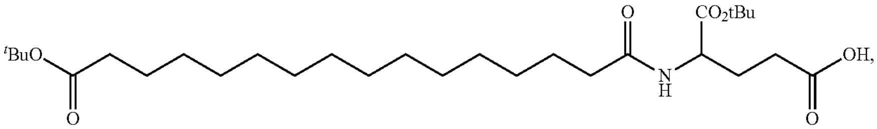

,

Formula 11-8

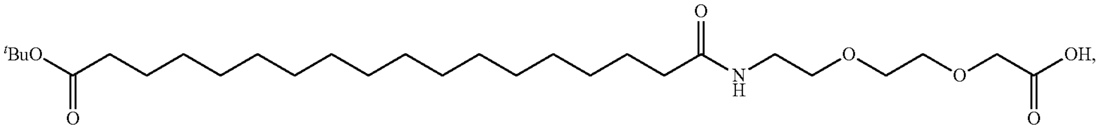

,

Formula 11-9

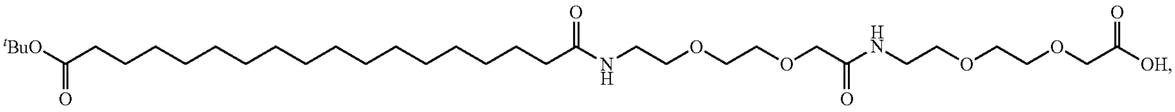

,

Formula 2'-17

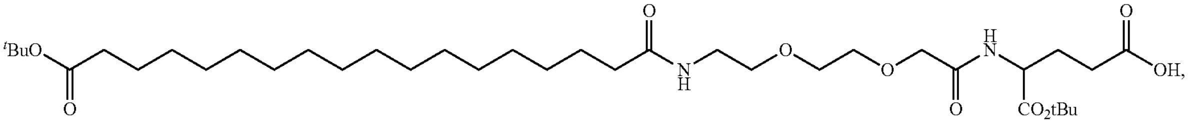

,

Formula 2'-18

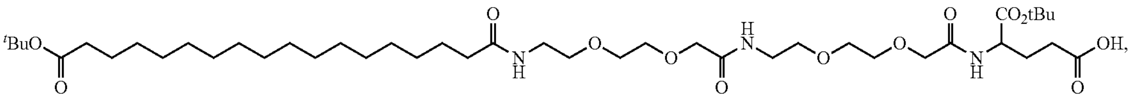

, and

-continued
Formula 11-10
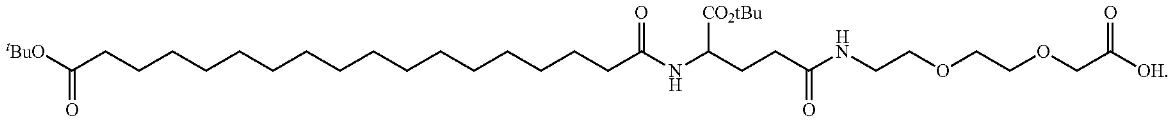
8. The process according to claim 1 wherein the compound of Formula Z—$(Y)_b$—OH is:
Formula 11-11
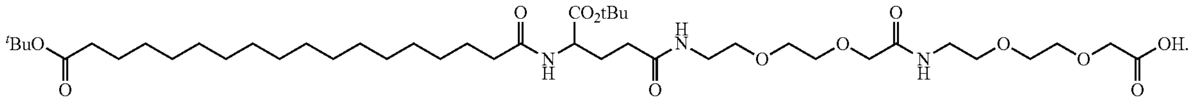
* * * * *